United States Patent
Liu et al.

(10) Patent No.: US 10,647,700 B2
(45) Date of Patent: May 12, 2020

(54) EZH2 INHIBITOR AND USE THEREOF

(71) Applicant: TARAPEUTICS SCIENCE INC., Bengbu, Anhui Province (CN)

(72) Inventors: Qingsong Liu, Anhui (CN); Jing Liu, Anhui (CN); Fengchao Lv, Anhui (CN); Chen Hu, Anhui (CN); Wen Liang Wang, Anhui (CN); Ao Li Wang, Anhui (CN); Zi Ping Qi, Anhui (CN); Xiao Fei Liang, Anhui (CN); Wen Chao Wang, Anhui (CN); Tao Ren, Anhui (CN); Bei Lei Wang, Anhui (CN); Li Wang, Anhui (CN)

(73) Assignee: TARAPEUTICS SCIENCE INC., Bengbu, Anhui Province (CN)

( * ) Notice: Subject to any disclaimer, the term of this patent is extended or adjusted under 35 U.S.C. 154(b) by 0 days.

(21) Appl. No.: 16/478,277

(22) PCT Filed: Jan. 17, 2018

(86) PCT No.: PCT/CN2018/073002
§ 371 (c)(1),
(2) Date: Jul. 16, 2019

(87) PCT Pub. No.: WO2018/133795
PCT Pub. Date: Jul. 26, 2018

(65) Prior Publication Data
US 2019/0367482 A1 Dec. 5, 2019

(30) Foreign Application Priority Data
Jan. 17, 2017 (CN) .......................... 2017 1 0045099

(51) Int. Cl.
C07D 401/14 (2006.01)
C07D 401/12 (2006.01)
C07D 413/12 (2006.01)
C07D 413/14 (2006.01)

(52) U.S. Cl.
CPC ......... *C07D 401/14* (2013.01); *C07D 401/12* (2013.01); *C07D 413/12* (2013.01); *C07D 413/14* (2013.01)

(58) Field of Classification Search
CPC .. C07D 401/14; C07D 401/12; C07D 413/12; C07D 413/14
See application file for complete search history.

(56) References Cited

U.S. PATENT DOCUMENTS

| | | |
|---|---|---|
| 5,763,263 A | 6/1998 | Dehlinger |
| 7,563,589 B2 | 7/2009 | Zhang et al. |
| 8,765,732 B2 | 7/2014 | Kuntz et al. |
| 2014/0128393 A1 | 5/2014 | Knutson et al. |
| 2015/0051163 A1 | 2/2015 | Keilhack et al. |
| 2019/0135796 A1* | 5/2019 | Bradner ............... C07D 405/14 |

FOREIGN PATENT DOCUMENTS

| | | |
|---|---|---|
| CN | 104066718 A | 9/2014 |
| CN | 104080769 A | 10/2014 |
| CN | 104768555 A | 7/2015 |
| WO | 2017139404 A1 | 8/2017 |
| WO | 2017/184999 A1 | 10/2017 |

OTHER PUBLICATIONS

Bracken A.P. et al., "EZH2 is Downstream of the pRB-E2F Pathway, Essential for Proliferation and Amplified in Cancer", The EMBO Journal 22(20):5323-5335 (2003).
Kirmizis A. et al., "Identification of the Polycomb Group Protein SU(Z)12 as a Potential Molecular Target for Human Cancer Therapy", Molecular Cancer Therapeutics 2:113-121 (Jan. 2003).
Kleer C.G. et al., "EZH2 is a Marker of Aggressive Breast Cancer and Promotes Neoplastic Transformation of Breast Epithelial Cells", PNAS 100(20):11606-11611 (Sep. 30, 2003).
Morin R.D. et al., "Somatic Mutation of EZH2 (Y641) in Follicular and Diffuse Large B-Cell Lymphomas of Germinal Center Origin", Nat Genet. 42(2):181-185 (Feb. 2010).
Otte A.P. et al., "Gene Repression by Polycomb Group Protein Complexes: a Distinct Complex for Every Occasion?", Current Opinion in Genetics & Development 13:448-454 (2003).
Varambally S. et al., "The Polycomb Group Protein EZH2 is Involved in Progression of Prostate Cancer", Nature 419:624-629 (Oct. 10, 2002).
International Search Report dated Apr. 18, 2018 received in International Application No. PCT/CN2018/073002, together with an English-language translation.

* cited by examiner

Primary Examiner — Timothy R Rozof
(74) Attorney, Agent, or Firm — Scully, Scott, Murphy & Presser, P.C.

(57) ABSTRACT

An inhibitor of a wild type and Y641F mutant of human histone methyltransferase EZH2 is provided herein. Particularly, the inhibitor is a compound represented by formula (I) or a pharmaceutically acceptable salt thereof. The inhibitor can be used to treat a cancer or precancerous condition related to EZH2 activity.

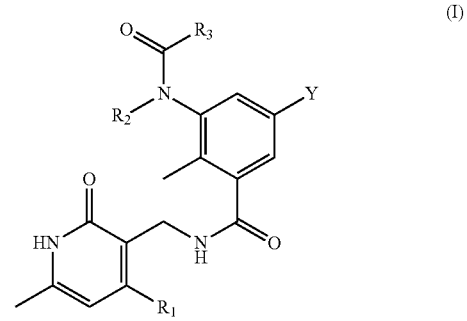

15 Claims, No Drawings
Specification includes a Sequence Listing.

SEQUENCE LISTING

<160> NUMBER OF SEQ ID NOS: 4

<210> SEQ ID NO 1
<211> LENGTH: 36
<212> TYPE: DNA
<213> ORGANISM: Artificial Sequence
<220> FEATURE:
<223> OTHER INFORMATION: synthetic oligonucleotide

```
<400> SEQUENCE: 1
ggcgagctcc tgatcattat tcccattagg agggtg                                36

<210> SEQ ID NO 2
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 2
ggcagatctg gctggccggg gacgccgagc gag                                   33

<210> SEQ ID NO 3
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 3
gcggtaccgt tgacattgat tattgactag ttattaata                             39

<210> SEQ ID NO 4
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 4
ggcctcgagg agctctgctt atatagacct ccca                                  34
```

EZH2 INHIBITOR AND USE THEREOF

TECHNICAL FIELD

The present invention relates to an inhibitor of wild-type and certain mutant forms of human histone methyltransferase EZH2, and also relates to a method of using the inhibitor for treating a cancer or a precancerous condition associated with EZH2 activity as well as use thereof.

BACKGROUND OF THE INVENTION

In eukaryotic cells DNA is packaged with histones to form chromatin. Approximately 150 base pairs of DNA are wrapped twice around an octamer of histones (two each of histones 2A, 2B, 3 and 4) to form a nucleosome, the basic unit of chromatin. Changes in the ordered structure of chromatin can lead to alterations in transcription of associated genes. This process is highly controlled because changes in gene expression patterns can profoundly affect fundamental cellular processes, such as differentiation, proliferation and apoptosis. Control of changes in chromatin structure (and hence of transcription) is mediated by covalent modifications to histones, most notably of their N-terminal tails. These modifications are often referred to as epigenetic because they can lead to heritable changes in gene expression, but they do not affect the sequence of the DNA itself. Covalent modifications (for example, methylation, acetylation, phosphorylation and ubiquitination) of the side chains of amino acids are enzymatically mediated.

The selective addition of methyl groups to specific amino acid sites on histones is controlled by the action of a unique family of enzymes known as histone methyltransferases (HMTs). The level of expression of a particular gene is influenced by the presence or absence of one or more methyl groups at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species, and still other enzymes can remove these species to provide control of gene expression.

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion. Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease), and cardiovascular diseases. Therefore, selectively modulating the aberrant action of epigenetic enzymes holds great promise for the treatment of a range of diseases.

Enhancer of Zeste Homolog 2 (Drosophila) (EZH2) catalyzes trimethylation of lysine 27 on histone H3 (H3K27me3), with its prominent function being to adjust the structure of chromosome. A variety of tumors have high expression of EZH2, which is closely related to the malignant process, invasiveness and metastasis of tumors. Main functions of EZH2 comprise catalyzing methylation of histone, participating in DNA methylation and interfering with DNA repair. EZH2 is a member of the PcG (polycomb-group) gene family. Two complexes, PRC1 (polycomb repressive complex 1) and PRC2 (polycomb repressive complex 2), respectively play a role in maintaining gene suppression and initialing gene silencing. EZH2 gene, together with EED and SUZ12 constitute PRC2 complex, wherein EZH2, as the catalytic subunit of PRC2, can catalyze H3K27m3 and H3K9m3 via its highly conserved SET region in histone methyltransferase, thereby suppressing transcription and regulating gene activity at chromosome level. EZH2 in PRC2 and PRC3 is able to interact with DNA methyltransferase to enhance its activity. Studies have shown that EZH2 is required in binding between some target genes of EZH2 and DNA methyltransferase. In addition, EZH2 is also needed in assisting the methylation of promoters of EZH2-targeted genes. EZH2 plays a role in the recruitment of DNA methyltransferases.

Biochemical and genetic studies have provided evidence that Drosophila PcG proteins function in at least two distinct protein complexes, the Polycomb repressive complex 1 (PRC 1) and the ESC-E(Z) complex (also known as Polycomb repressive complex 2 (PRC2)), although the compositions of the complexes may be dynamic (Otte et al. Curr OpinGenet Dev, 2003, 13:448-54). Studies in Drosophila and mammalian cells have demonstrated that the ESC-E(Z)/EED-EZH2 (i.e., PRC2) complexes have intrinsic histone methyltransferase activity. The complexes generally contain EED, EZH2, SUZ12, and RbAp48 or Drosophila homologs thereof. However, a reconstituted complex comprising only EED, EZH2, and SUZ12 retains histone methyltransferase activity for lysine 27 of histone H3 (U.S. Pat. No. 7,563,589).

Of the various proteins making up PRC2 complexes, EZH2 (Enhancer of Zeste Homolog 2) is the catalytic subunit. The catalytic site of EZH2 in turn is present within a SET domain, a highly conserved sequence motif (named after Su(var)3-9, Enhancer of Zeste, Trithorax) that is found in several chromatin-associated proteins, including members of both the Trithorax group and Polycomb group. SET domain is characteristic of all known histone lysine methyltransferases except the H3-K79 methyltransferase DOT1.

Consistent with a role of EZH2 in maintaining the epigenetic modification patterns of pluripotent epiblast cells, Cre-mediated deletion of EZH2 results in loss of histone H3-K27 methylation in the cells. Further, studies in prostate and breast cancer cell lines and tissues have revealed a strong correlation between the levels of EZH2 and SUZ12 and the invasiveness of these cancers (Bracken et al. (2003) EMBO J 22:5323-35; Kirmizis et al. (2003) Mol Cancer Ther 2:113-21; Kleer et al. (2003) Proc Natl Acad Sci USA 100:11606-11; Varambally et al. (2002) Nature 419:624-9).

Recently, somatic mutations of EZH2 were reported to be associated with follicular lymphoma (FL) and the germinal center B cell-like (GCB) subtype of diffuse large B-cell lymphoma (DLBCL) (Morin et al. (2010) Nat Genet. 42:181-5). In all cases, occurrence of the mutant EZH2 gene was found to be heterozygous, and expression of both wild-type and mutant alleles was detected in the mutant samples profiled by transcriptome sequencing. Currently, the R-CHOP approach has been a standard therapy for most diffuse large B-cell lymphoma (DLBCL).

Small molecule inhibitors of EZH2 that has entered phase II clinical testing so far include EPZ6438 (Tazemetostat) which is used for treating non-Hodgkin B-cell lymphoma (see U.S. Pat. No. 8,765,732B2, US20140128393A1, US20151163A1). In addition, also included is GSK126 (CAS No.: 1346574-57-9) developed by GSK which has currently entered into clinical phase I and which is also a small molecule inhibitor of EZH2 for treating diffuse large B-cell lymphoma and follicular lymphoma.

SUMMARY OF THE INVENTION

The invention provides an inhibitor of wild-type or mutant EZH2. In particular, the compound of the invention includes a compound of formula (I), or a pharmaceutically acceptable salt, solvate, isomer, ester, acid, metabolite or prodrug thereof:

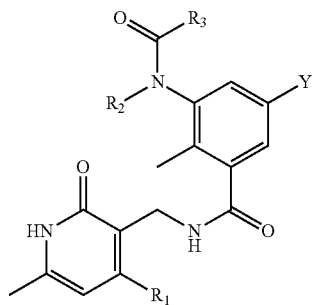

(I)

wherein,

Y is selected from a group consisting of cyano, aminoacyl, alkylamino optionally substituted with one $R_4$, aryl optionally substituted with 1-3 independent $R_4$, heteroaryl optionally substituted with 1-3 independent $R_4$, and heterocycloalkylalkylamino optionally substituted with 1-3 independent $R_4$;

$R_1$ is alkyl;

$R_2$ is selected from a group consisting of hydrogen, alkyl and cycloalkylalkyl;

$R_3$ is selected from a group consisting of alkyl, cycloalkyl, heterocycloalkyl, heteroaryl, alkylaryl, and bicyclo[2.2.1]hept-2-enyl;

$R_4$ is independently selected from a group consisting of hydrogen, halo, amino, cyano, alkyl, alkoxy, alkanoyl, alkylamino optionally substituted with one $R_5$, alkylsulfonamide optionally substituted with one $R_5$, cycloalkylsulfonamide optionally substituted with one $R_5$, heterocycloalkyl optionally substituted with 1-3 independent $R_5$, heterocycloalkylcarbonyl optionally substituted with 1-3 independent $R_5$, heterocycloalkylalkyl optionally substituted with 1-3 independent $R_5$, heterocycloalkylalkoxy optionally substituted with 1-3 independent $R_5$, heterocycloalkylcarbonylalkyl optionally substituted with 1-3 independent $R_5$, and aryloxy optionally substituted with 1-3 independent $R_5$; and $R_5$ is independently selected from a group consisting of amino, alkyl, alkanoyl, alkylamino, hydroxyalkyl, cycloalkyl, cycloalkylalkyl, heterocycloalkyl, and amino protecting group.

In a more preferred embodiment, the present invention provides an inhibitor of EZH2 kinase, comprising a compound of formula (II), or a pharmaceutically acceptable salt, solvate, ester, acid, metabolite or prodrug thereof:

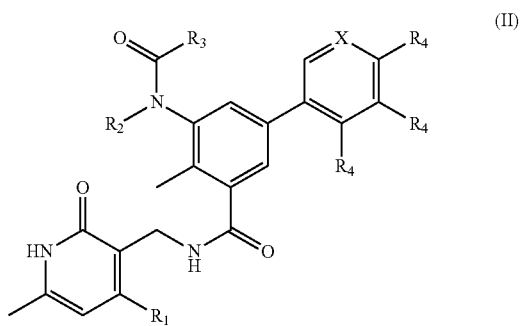

(II)

wherein, X is selected from a group consisting of CH and N, and $R_1$, $R_2$, $R_3$ and $R_4$ are as defined above.

In a particularly preferred embodiment, X is CH, and $R_1$, $R_2$, $R_3$ and $R_4$ are as defined above.

In another aspect, the present invention provides a pharmaceutical composition, which comprises a therapeutically effective of at least one of a compound of formula (I) or formula (II) as provided herein, or a pharmaceutically acceptable salt, solvate, isomer, ester, acid, metabolite or prodrug thereof, as well as pharmaceutically acceptable carrier or excipient and optional other therapeutic agents.

In another aspect, the present invention relates to a method of using or use of a compound of formula (I) or formula (II) or a pharmaceutically acceptable salt, solvate, isomer, ester, acid, metabolite or prodrug thereof in inhibiting EZH2 activity.

In an embodiment, the EZH2 inhibitor of the present invention inhibits the histone methyltransferase activity of wild-type EZH2. In an embodiment, the EZH2 inhibitor of the present invention inhibits the histone methyltransferase activity of mutant EZH2. In an embodiment, the EZH2 inhibitor inhibits both the histone methyltransferase activity of wild-type EZH2 and that of mutant EZH2. In an embodiment, the EZH2 inhibitor selectively inhibits the histone methyltransferase activity of mutant EZH2, especially the histone methyltransferase activity of Y641F-mutant EZH2.

In another aspect, the present invention provides a method for treating a cancer or a precancerous condition associated with EZH2 activity and the use thereof.

The subject of the present invention comprises any human subject who has been diagnosed with, has symptoms of, or is at risk of developing a cancer or a precancerous condition. For example, the cancer is lymphoma, leukemia or melanoma. Preferably, the lymphoma is a non-Hodgkin's lymphoma, a follicular lymphoma or a diffuse large B-cell lymphoma. Alternatively, the leukemia is chronic myelogenous leukemia (CML). The precancerous condition is myelodysplastic syndrome (MDS, previously referred to as pre-leukemia).

DETAILED DESCRIPTION OF THE INVENTION

Definitions

Unless otherwise defined, all technical and scientific terms used herein have the same meaning as commonly understood by one of ordinary skill in the art to which this invention belongs. In the specification, the singular forms also include the plural unless the context clearly dictates otherwise. All publications, patent applications, patents and other references mentioned herein are incorporated by reference. In the case of conflict, the present specification, including definitions, will control. In addition, the materials, methods and examples are illustrative only and are not intended to be limiting.

Unless otherwise indicated, conventional methods of mass spectroscopy, NMR, HPLC, protein chemistry, biochemistry, recombinant DNA techniques and pharmacology that are within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed with conventional methods well known in the art and those as described in various general and more specific references that are cited and discussed throughout the present specification.

The term "alkyl" refers to an aliphatic hydrocarbon group, which may be branched or straight alkyl. Depending on the structure, an alkyl group may be a monoradical or a diradical (i.e., an alkylene group). In the invention, the alkyl group is preferably an alkyl having 1 to 8 carbon atoms, more preferably a "lower alkyl" having 1 to 6 carbon atoms, and even more preferably an alkyl having 1 to 4 carbon atoms. Typical alkyl groups include, but are not limited to, methyl, ethyl, propyl, butyl, pentyl, hexyl, and the like. It should be understood that the "alkyl" as mentioned herein encompasses all configurations and conformations that may exist of the alkyl, e.g., the "propyl" as mentioned herein intends to encompass n-propyl and isopropyl, "butyl" as mentioned herein intends to encompass n-butyl, isobutyl, and tertiary butyl, and "pentyl" as mentioned herein intends to encompass n-pentyl, isopentyl, neopentyl, tert-pentyl, pent-3-yl, etc.

The term "cycloalkyl" refers to a monocyclic or polycyclic radical that contains only carbon and hydrogen. Cycloalkyl groups include groups having from 3 to 8 ring atoms. Depending on the structure, a cycloalkyl group can be a monoradical or a diradical (e.g., a cycloalkylene group). In the invention, the cycloalkyl group is preferably a cycloalkyl having 3 to 8 carbon atoms, and more preferably a "lower cycloalkyl" having 3 to 6 carbon atoms. Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl.

"Alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

The term "amino" refers to —NH$_2$ group. The term "aminoacyl" refers to —CO—NH$_2$. The term "amide" or "amido" refers to —NR—CO—R', wherein each of R and R' is independently hydrogen or alkyl.

The term "alkylamino" refers to an amino substituent which is further substituted with one or two alkyl groups, specifically the group —NRR', wherein R and R' are each independently selected from the group consisting of hydrogen or lower alkyl, with the proviso that —NRR' is not —NH$_2$. "Alkylamino" includes groups of compounds wherein nitrogen of —NH$_2$ is bound to at least one alkyl group. Examples of alkylamino groups include benzylamino, methylamino, ethylamino, phenethylamino, etc. "Dialkylamino" includes groups wherein the nitrogen of —NH$_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively.

"cycloalkylalkyl" refers to an alkyl group as defined herein is subsitututed with cycloalkyl as defined herein. Non-limiting examples of cycloalkylalkyl include cyclopropylmethyl, cyclopropylethyl, cyclobutylmethyl, cyclobutylethyl, cyclopentylmethyl, cyclohexylmethyl, etc.

The term "carbonyl" is an organic functional group (C=O) formed by carbon atom and oxygen atom through a double bond linkage. The term "alkanoyl" or "alkylcarbonyl" means a carbonyl further substituted with an alkyl group.

The term "alkylsulfonamide" and "cycloalkylsulfonamide" refers to —NH—S(=O)$_2$—R, wherein R are respectively alkyl and cycloalkyl.

The term "halo" or "halogen" means fluoro, chloro, bromo and iodo.

As used herein, the term "cyano" refers to a group of formula —CN.

The term "aromatic" refers to a planar ring having a delocalized 7-electron system containing 4n+2 π electrons, where n is an integer. Aromatic rings can be formed by five, six, seven, eight, nine, or more than nine atoms. Aromatics can be optionally subsitituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuryl, indazolyl, indolizinyl, phthalazinyl, pyridazinyl, isoindolyl, pteridinyl, purinyl, oxadiazolyl, thiadiazolyl, furyl, benzofuryl, benzothiophenyl, benzothiazolyl, benzoxazolyl, quinazolinyl, naphthyridinyl, furopyridinyl, and the like.

As used herein, the term "heterocycloalkyl" or "heterocyclyl" refers to a non-aromatic ring wherein one or more atoms forming the ring is a heteroatom selected from the group consisting of nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, ethylene oxide, azetidine, oxetane, thietane, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine (tetrahydropyrrole), imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane, isoindoline, indoline, 1,2,3,6-tetrahydropyridine, dihydropyran, pyran, 1,4-diazepane, 1,4-diazepane, 2-oxa-5-azabicyclo[2.2.1]heptane and 2,5-diazabicyclo[2.2.1]heptanes, etc. Depending on the structure, a heterocycloalkyl group can be a monoradical or a diradical (i.e., a heterocycloalkylene group).

"aryloxy" refers to —O-aryl, wherein aryl is as defined herein.

The term "alkylaryl" or "aryl(alkyl)" refers to an aryl group as defined herein that is substituted with an alkyl as defined herein.

The term "heterocycloalkylalkyl" or "alkyl(heterocycloalkyl)" refers to an alkyl group as defined herein that is substituted with heterocycloalkyl. The term "heterocycloalkylalkoxy" or "alkoxy(heterocycloalkyl)" refers to alkoxy as defined herein that is substituted with heterocycloalkyl as defined herein.

The term "heterocycloalkylcarbonyl" refers to carbonyl that is further substituted with a heterocycloalkyl. The term "heterocycloalkylcarbonylalkyl" refers to alkyl that is further substituted with a heterocycloalkylcarbonyl.

The term "optionally" means that the subsequently described event(s) may or may not occur, and includes both event(s), which occur, and events that do not occur. The term "optionally substituted" or "substituted" means that the referenced group may be substituted with one or more additional group(s) individually and independently selected from the group consisting of alkyl, cycloalkyl, aryl, heteroaryl, hydroxy, alkoxy, cyano, halo, amide, nitro, haloalkyl, amino, alkylcarbonyl, alkoxycarbonyl, heteroarylalkyl, heterocycloalkylalkyl, aminoacyl, amino protecting group, etc.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics*, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "prodrug" or "a precursor of a drug" refers to derivatives that may not possess pharmacological activity, but may, in certain instances, be administered orally or parenterally and thereafter metabolized in the body to form compounds of the invention which are pharmacologically active. Non-limiting examples of prodrugs include esters, carbonate esters, hemi-esters, phosphate esters, nitro esters, sulfate esters, sulfoxides, amides, carbamates, azo-compounds, phosphamides, glycosides, ethers, acetals, and ketals, etc.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "precancerous condition" refers to a disease, syndrome, or finding that, if left untreated, may lead to cancer. It is a generalized state associated with a significantly increased risk of cancer.

The term "treating" as used herein refers to alleviate of at least one symptom of the disease, disorder or condition. The term encompasses the administration and/or application of one or more compounds described herein, to a subject, for the purpose of providing management of, or remedy for a condition. "Treatment" for the purposes of this disclosure, may, but does not have to, provide a cure; rather, "treatment" may be in the form of management of the condition. When the compounds described herein are used to treat unwanted proliferating cells, including cancers, "treatment" includes partial or total destruction of the undesirable proliferating cells with minimal destructive effects on normal cells. A desired mechanism of treatment of unwanted rapidly proliferating cells, including cancer cells, at the cellular level is apoptosis.

The term "preventing" as used herein includes either preventing or slowing the onset of a clinically evident disease progression altogether or preventing or slowing the onset of a preclinically evident stage of a disease in individuals at risk. This includes prophylactic treatment of those at risk of developing a disease.

The term "subject" as used herein for purposes of treatment includes any human subject who has been diagnosed with, has symptoms of, or is at risk of developing a cancer or a precancerous condition. For methods of prevention the subject is any human subject. To illustrate, for purposes of prevention, a subject may be a human subject who is at risk of or is genetically predisposed to obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on.

As used herein, $GI_{50}$ refers to a concentration of a medicine required for inhibiting the growth of 50% cells i.e., the medicine concentration at which the growth of 50% cells (such as cancer cells) is inhibited or controlled.

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

The Novel EZH2 Inhibitor of the Present Invention

Various aspects of the present invention relate to an EZH2 kinase inhibitor, comprising a compound of formula (I) or a pharmaceutically acceptable salt, solvate, ester, acid, metabolite or prodrug thereof:

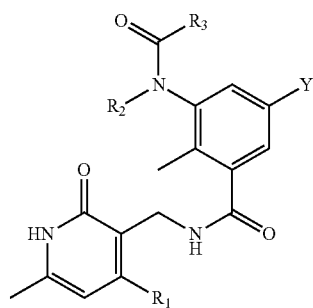

(I)

wherein,

Y is selected from a group consisting of cyano, aminoacyl, alkylamino optionally substituted with one $R_4$, aryl optionally substituted with 1-3 independent $R_4$, heteroaryl optionally substituted with 1-3 independent $R_4$, and heterocycloalkylalkylamino optionally substituted with 1-3 independent $R_4$;

$R_1$ is alkyl;

$R_2$ is selected from a group consisting of hydrogen, alkyl and cycloalkylalkyl;

$R_3$ is selected from a group consisting of alkyl, cycloalkyl, heterocycloalkyl, heteroaryl, alkylaryl, and bicyclo[2.2.1]hept-2-enyl;

$R_4$ is independently selected from a group consisting of hydrogen, halo, amino, cyano, alkyl, alkoxy, alkanoyl, alkylamino optionally substituted with one $R_5$, alkylsulfonamide optionally substituted with one $R_5$, cycloalkylsulfonamide optionally substituted with one $R_5$, heterocycloalkyl optionally substituted with 1-3 independent $R_5$, heterocycloalkylcarbonyl optionally substituted with 1-3 independent $R_5$, heterocycloalkylalkyl optionally substituted with 1-3 independent $R_5$, heterocycloalkylalkoxy optionally substituted with 1-3 independent $R_5$, heterocycloalkylcarbonylalkyl optionally substituted with 1-3 independent $R_5$, and aryloxy optionally substituted with 1-3 independent $R_5$;

$R_5$ is independently selected from a group consisting of amino, alkyl, alkanoyl, alkylamino, hydroxyalkyl, cycloalkyl, cycloalkylalkyl, heterocycloalkyl, and amino protecting group.

In an embodiment of the invention, alkyl is preferably $C_{1-8}$alkyl, more preferably $C_{1-5}$alkyl; cycloalkyl is preferably $C_{3-8}$cycloalkyl, more preferably $C_{3-6}$cycloalkyl; heterocycloalky is preferably 3-9 membered heterocycloalky, more preferably 6-membered heterocycloalkyl, particularly preferably selected from a group consisting of piperidyl, piperazinyl, morpholinyl, and tetrahydropyranyl, etc; aryl is preferably phenyl; heteroaryl is preferably selected from a group consisting of pyridyl, thienyl, and furanyl, etc; amino protecting group is preferably selected from a group consisting of pivaloyl, tert-buyoxycarbonyl, benzyloxycarbonyl, 9-fluorenylmethoxycarbonyl, benzyl, p-methyoxybenzyl, allyloxycarbonyl, and trifluoroacetyl, etc.

In a preferred embodiment of the invention, Y is selected from a group consisting of cyano, aminoacyl, (2-(dimethylamino)ethyl)(methyl)amino, phenyl, pyridyl, thienyl, (2-morpholinoethyl)amino, and (3-morpholinopropyl)amino, wherein phenyl, pyridyl, thienyl, (2-morpholinoethyl)amino, and (3-morpholinopropyl)amino are optionally substituted with 1-3 independent $R_4$; and wherein $R_4$ is independently selected from a group consisting of fluoro, chloro, cyano, methyl, methoxy, acetyl, (2-(dimethylamino)ethyl)amino, (2-(dimethylamino)ethyl)(methyl)amino, isopropylsulfonamide, cyclopropylsulfonamide, piperidyl, piperazinyl, morpholinyl, homopiperazinyl, morpholin-4-carbonyl, morpholinomethyl, piperidylmethyl, piperazinylmethyl, morpholinoethoxyl, morpholinopropoxy, morpholin-4-carbonylmethyl, and phenoxy, wherein piperidyl, piperazinyl, morpholinyl, homopiperazinyl, morpholin-4-carbonyl, morpholinomethyl, piperidylmethyl, piperazinylmethyl, morpholinoethoxyl, morpholinopropoxy, morpholin-4-carbonylmethyl, and phenoxy are optionally substituted with 1-3 independent $R_5$; and wherein $R_5$ is independently selected from a group consisting of amino, methyl, ethyl, isopropyl, acetyl, dimethylamino, hydroxymethyl, cyclopropyl, cyclopropylmethyl, pyrrolyl, and tert-butoxycarbonyl.

In another preferred embodiment, $R_1$ is selected from a group consisting of methyl, ethyl, and propyl; $R_2$ is selected from a group consisting of methyl, ethyl, propyl, and cyclopropylmethyl; $R_3$ is selected from a group consisting of isopropyl, neopentyl, tert-pentyl, pent-3-yl, cyclopropyl, cyclobutyl, cyclopentyl, cyclohexyl, tetrahydropyranyl, furyl, methylphenyl, and bicyclo[2.2.1]hept-2-enyl.

In another preferred embodiment of the present invention, Y is aryl or heteroaryl substituted with $R_4$, especially phenyl, pyridin-3-yl, or pyridin-4-yl substituted with $R_4$; and wherein $R_4$ is selected from a group consisting of halo, alkyl, heterocycloalkylalkyl optionally substituted with $R_5$, heterocycloalkylalkoxy optionally substituted with $R_5$, and heterocycloalkylalkyl optionally substituted with $R_5$, especially fluoro, methyl, 4-(cyclopropylmethyl)piperazin-1-yl, morpholinoethoxyl, morpholinopropoxy, morpholinomethyl, or piperazinylmethyl with its N atom optionally substituted with an amino protecting group.

In another preferred embodiment, $R_1$ is methyl.

In another preferred embodiment, $R_2$ is ethyl.

In a further preferred embodiment, $R_3$ is cyclopropyl or cyclopentyl.

In a more preferred embodiment, the present invention provides an EZH2 kinase inhibitor comprising a compound of formula (II) or a pharmaceutically acceptable salt, solvate, ester, acid, metabolite or prodrug thereof:

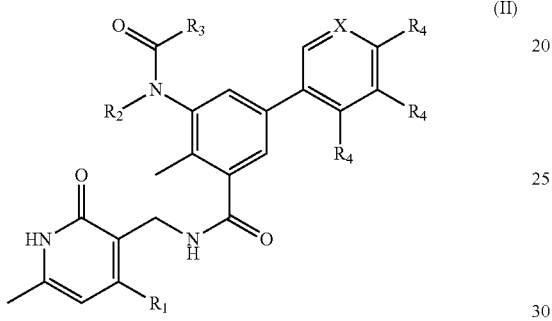

(II)

wherein X is selected from a group consisting of CH and N, and $R_1$, $R_2$, $R_3$ and $R_4$ are as defined above.

In a particularly preferred embodiment, X is CH, and $R_1$, $R_2$, $R_3$ and $R_4$ are as defined above. In a further preferred embodiment, $R_1$ is alkyl (such as methyl); $R_2$ is alkyl (such as ethyl); $R_3$ is selected from a group consisting of alkyl (such as isopropyl, neopentyl, tert-pentyl, and pent-3-yl), cycloalkyl (such as cyclopropyl, cyclobutyl, cyclopentyl, and cyclohexyl), heterocycloalkyl (such as tetrahydropyran-4-yl), heteroaryl (such as furan-2-yl), alkylaryl (such as p-methylphenyl), and bicyclo[2.2.1]hept-2-enyl; each of $R_4$ is independently selected from a group consisting of hydrogen, halo (such as fluoro), alkyl (such as methyl), alkylsulfonamide optionally substituted with one $R_5$ (such as isopropylsulfonamide), cycloalkylsulfonamide optionally substituted with one $R_5$ (such as cyclopropylsulfonamide), heterocycloalkyl optionally substituted with 1-3 independent $R_5$ (such as piperidyl, piperazinyl, morpholinyl), heterocycloalkylcarbonyl optionally substituted with 1-3 independent $R_5$ (such as morpholin-4-carbonyl), heterocycloalkylalkyl optionally substituted with 1-3 independent $R_5$ (such as morpholinomethyl, piperidylmethyl, piperazinylmethyl), heterocycloalkylalkoxy optionally substituted with 1-3 independent $R_5$ (such as morpholinoethoxyl, morpholinopropoxy), heterocycloalkylcarbonylalkyl optionally substituted with 1-3 independent $R_5$ (such as morpholin-4-carbonylmethyl), and aryloxy optionally substituted with 1-3 independent $R_5$ (such as phenoxy); $R_5$ is independently selected from a group consisting of alkyl (such as ethyl), cycloalkylalkyl (such as cyclopropylmethyl), alkylamino (such as dimethylamino), hydroxyalkyl (hydroxymethyl), and amino protecting group (such as t-butyloxycarbonyl).

In the present invention, preferred EZH2 inhibitors comprise compounds listed in the following table as well as their pharmaceutically acceptable salts, solvates, isomers, esters, acids, metabolite or prodrugs:

Compound 1

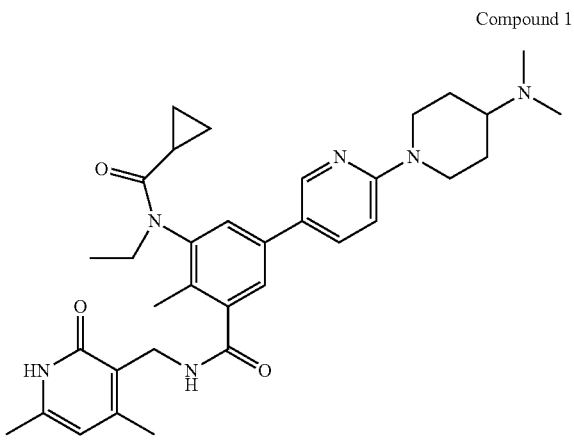

Compound 2

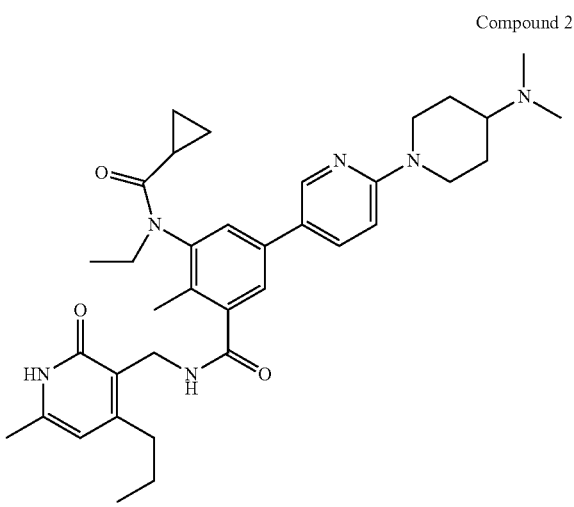

Compound 3

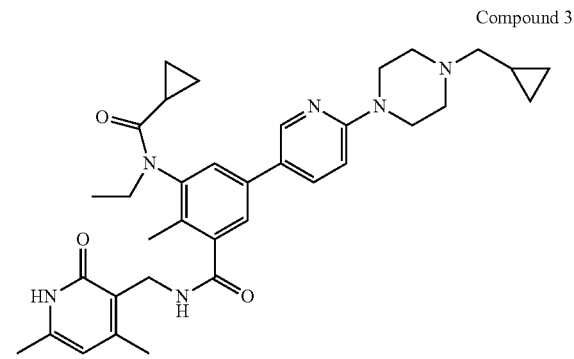

Compound 4
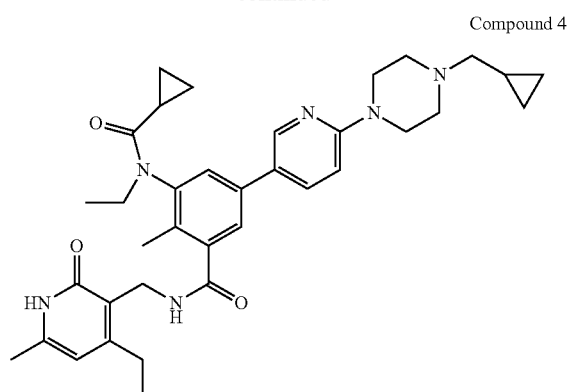
Compound 5
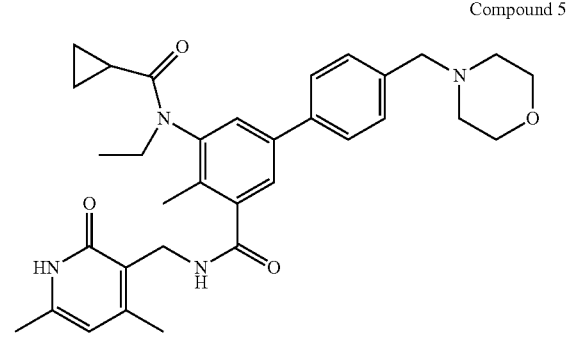
Compound 6
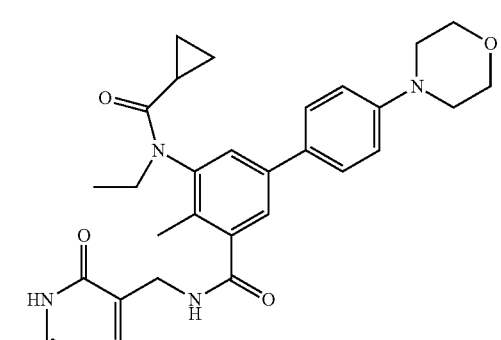
Compound 7
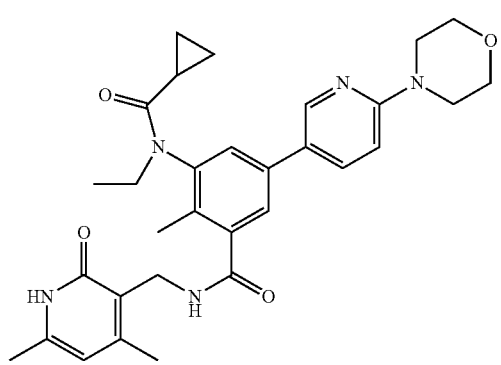
Compound 8
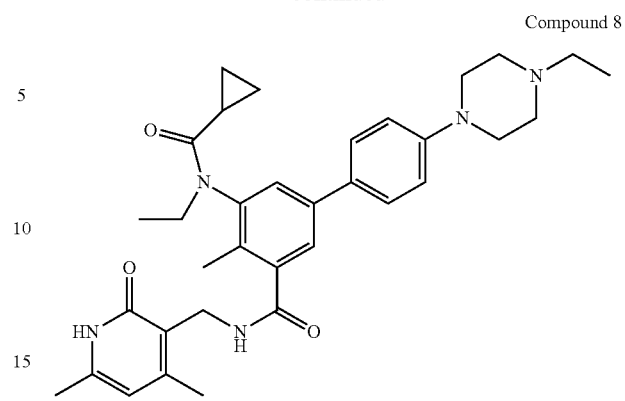
Compound 9
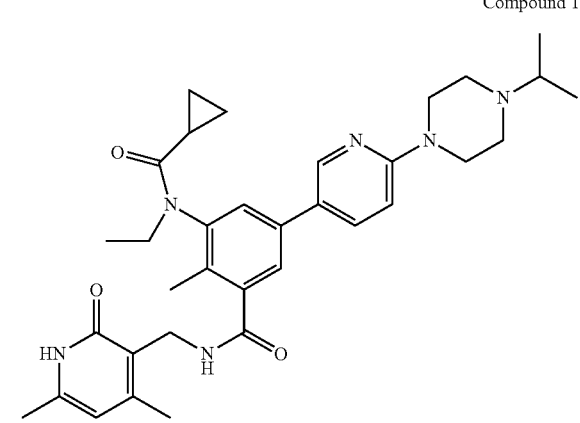
Compound 10
Compound 11
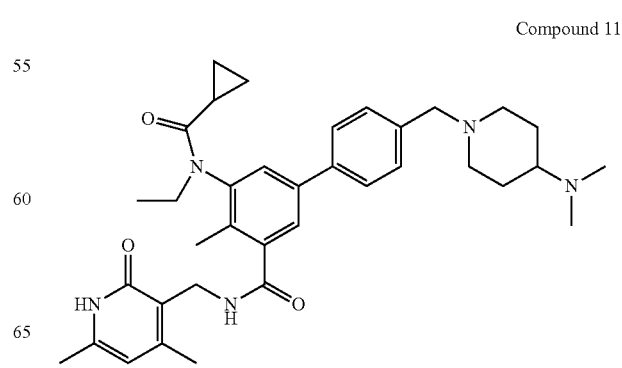

Compound 12
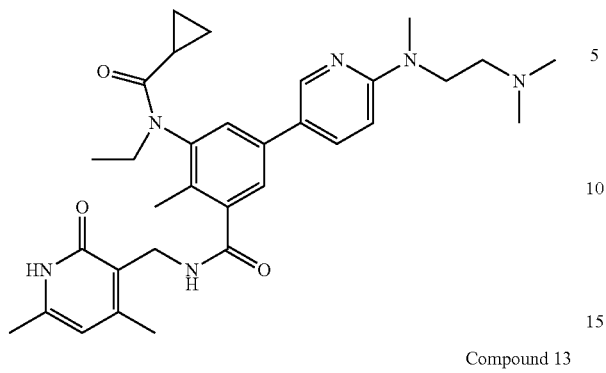
Compound 13
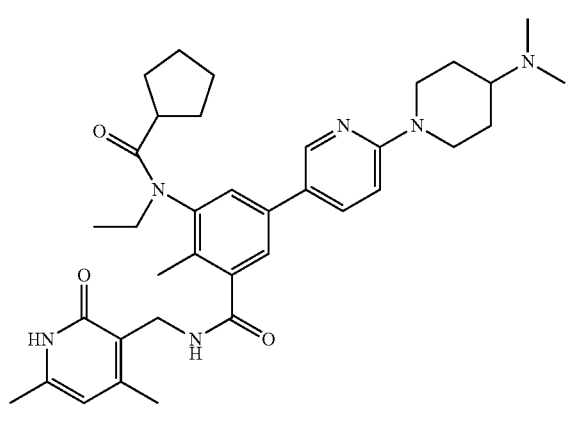
Compound 14
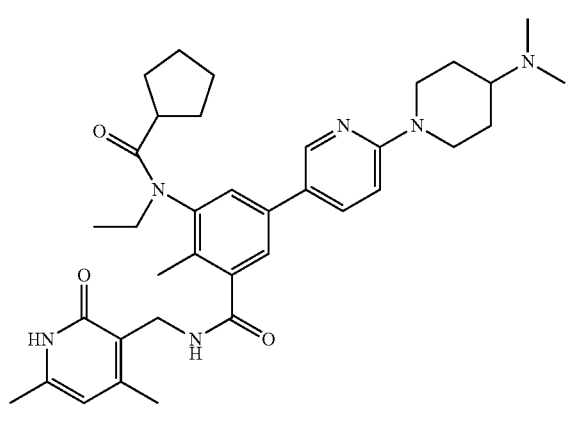
Compound 15
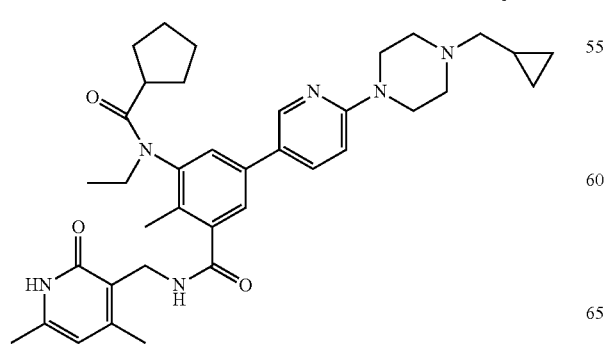
Compound 16
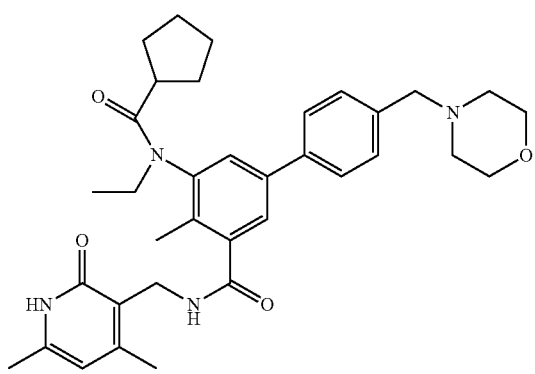
Compound 17
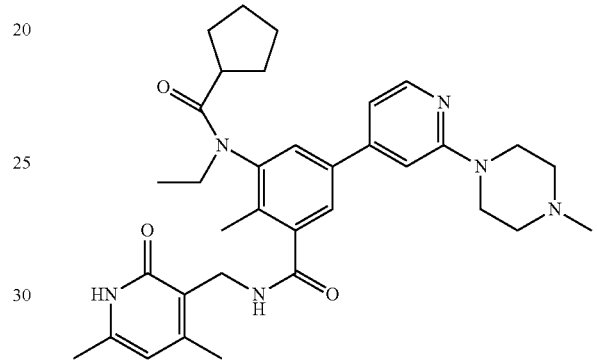
Compound 18
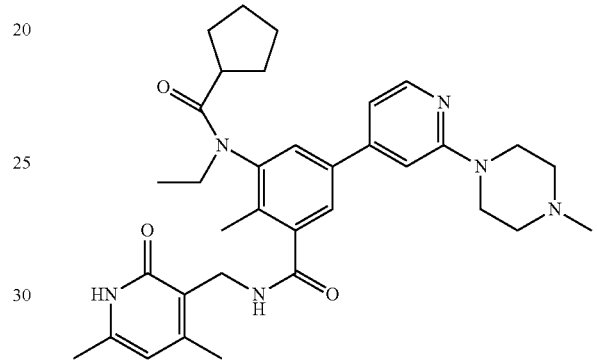
Compound 19
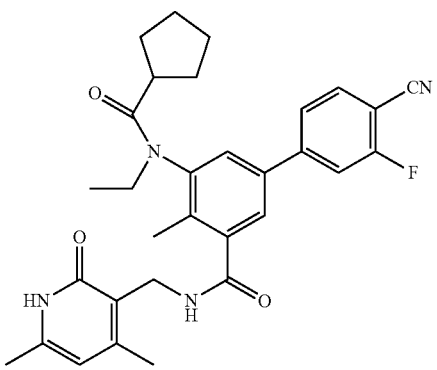

Compound 20
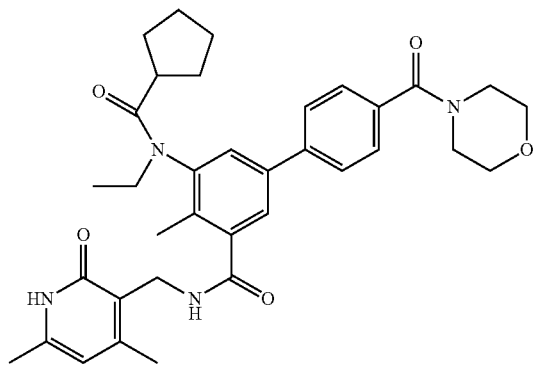
Compound 21
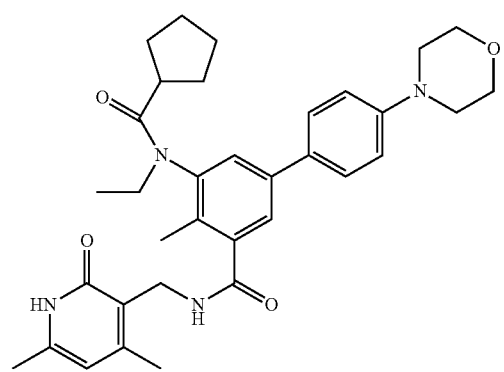
Compound 22
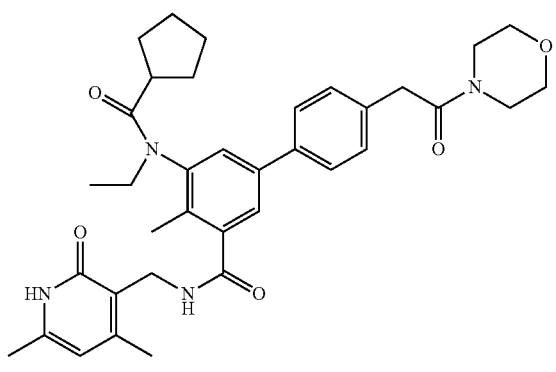
Compound 23
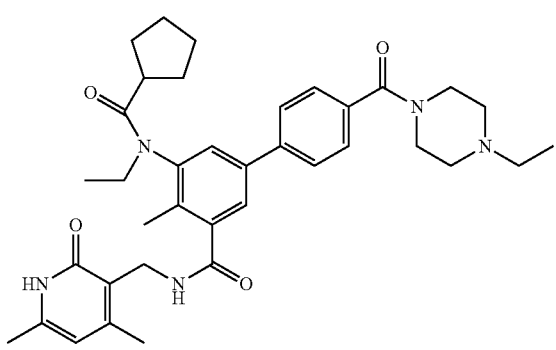
Compound 24
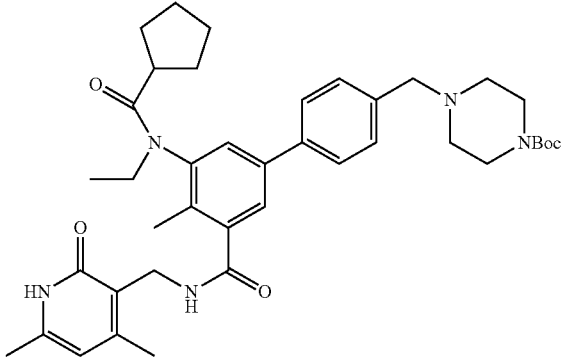
Compound 25
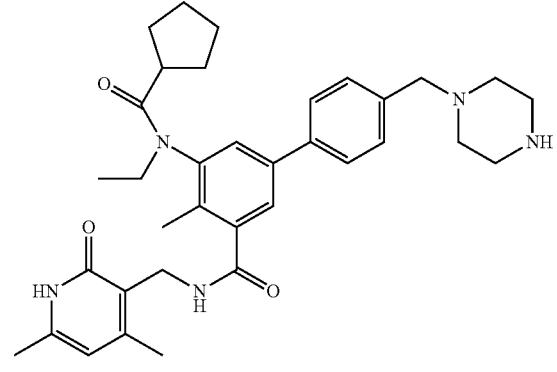
Compound 26
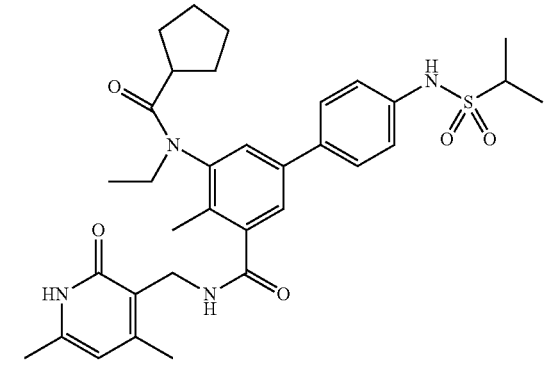
Compound 27
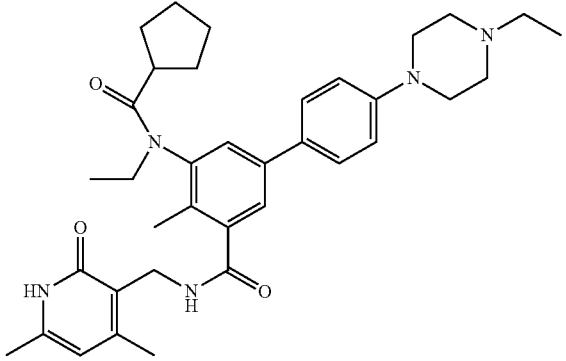

Compound 28
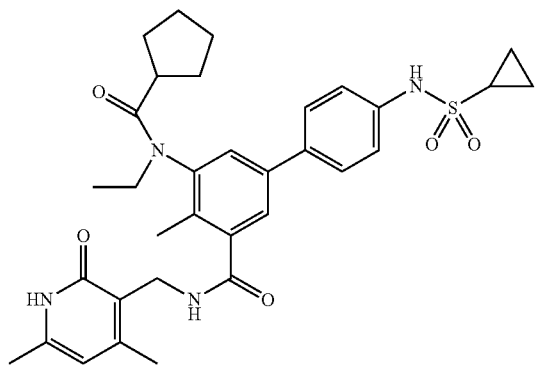
Compound 29
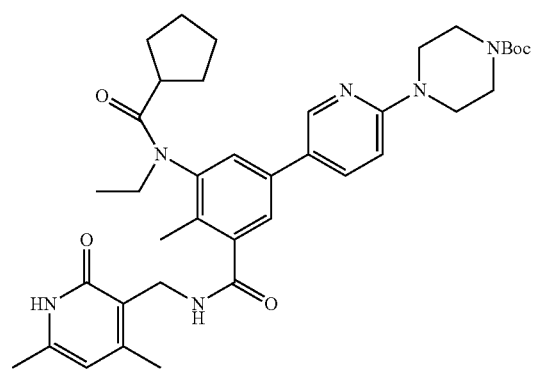
Compound 30
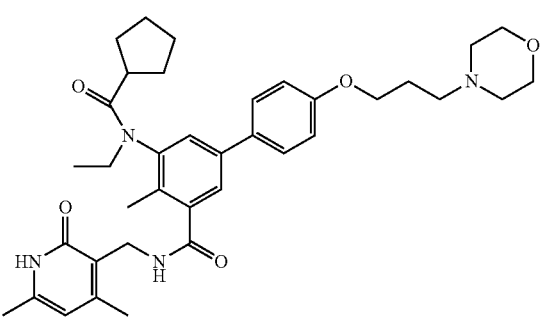
Compound 31
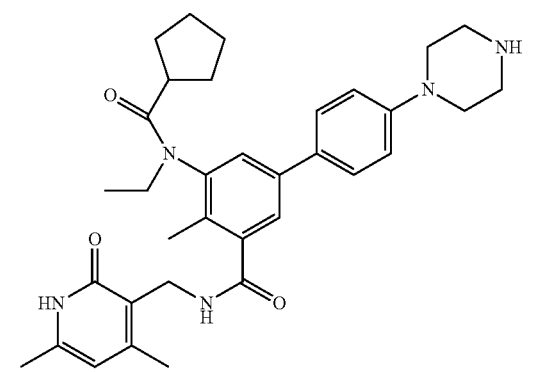
Compound 32
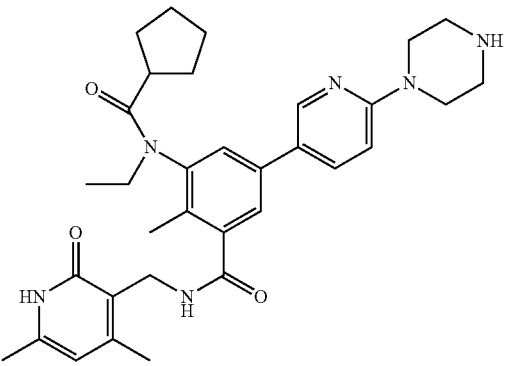
Compound 33
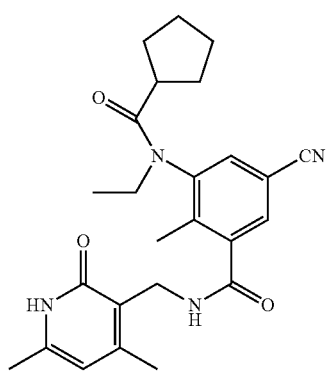
Compound 34
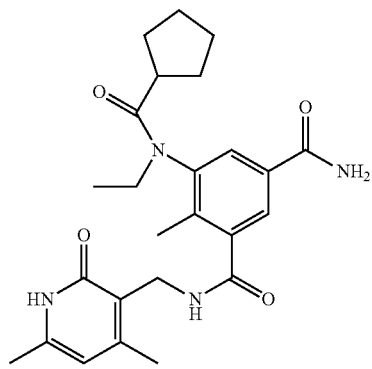
Compound 35
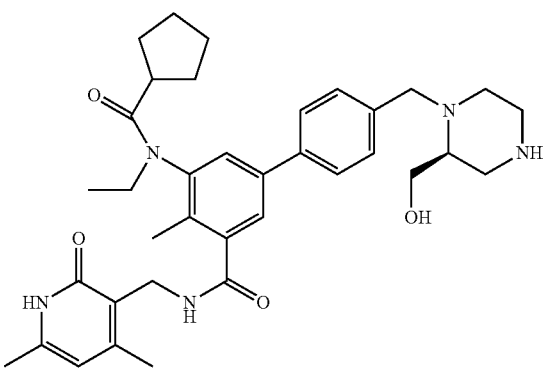

Compound 36
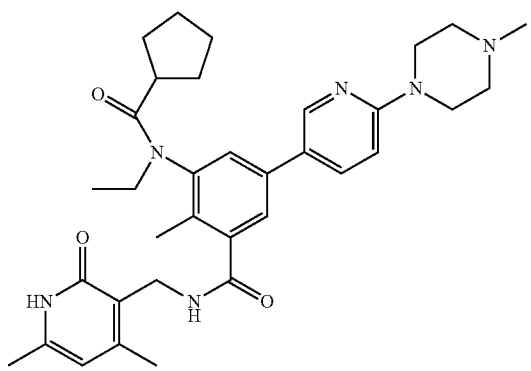
Compound 37
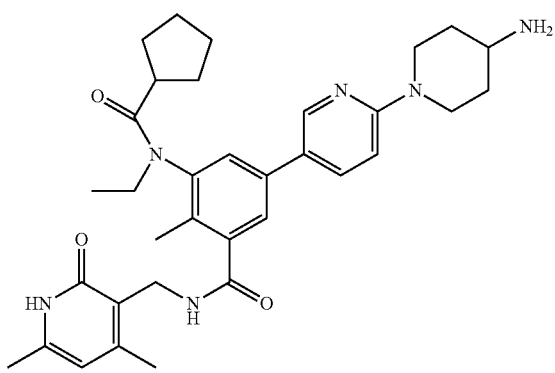
Compound 38
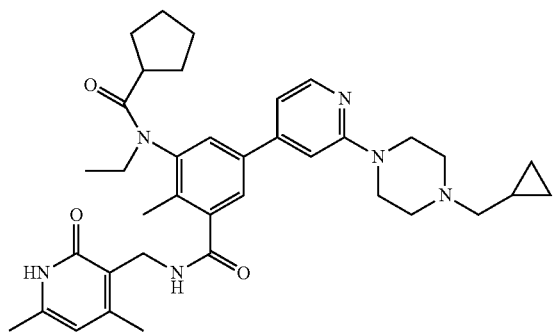
Compound 39
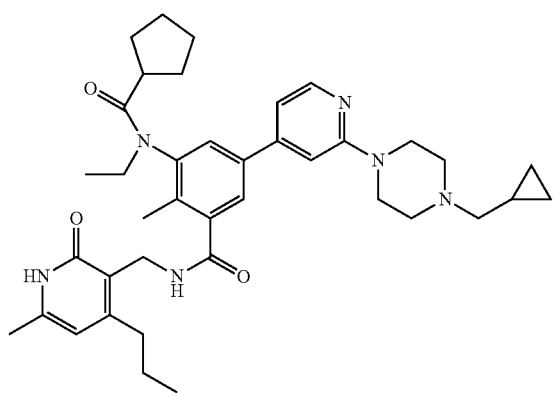
Compound 40
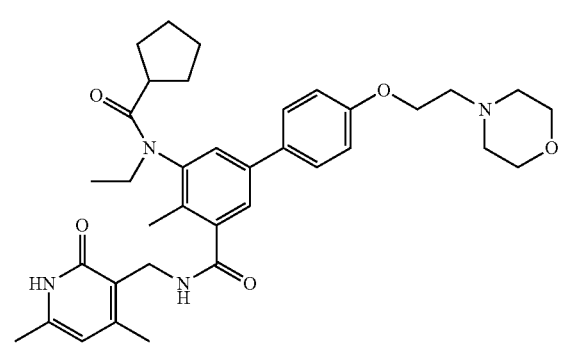
Compound 41
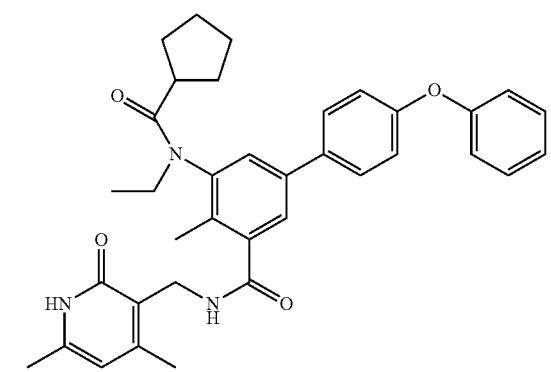
Compound 42
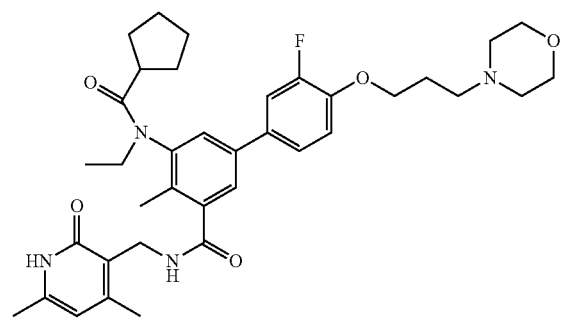
Compound 43
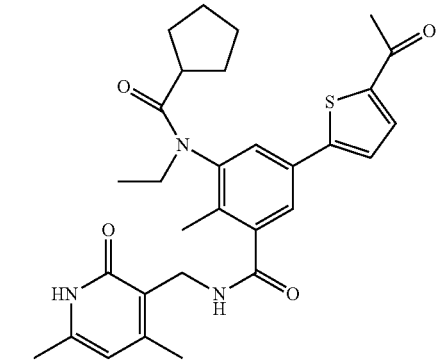

Compound 44
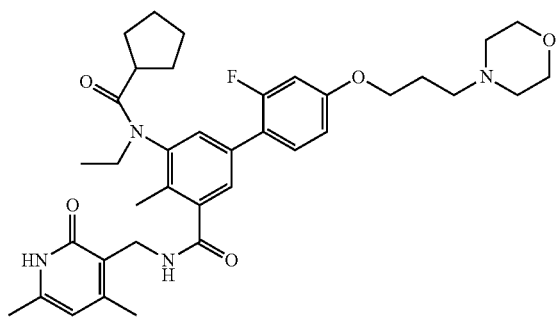
Compound 48
Compound 45
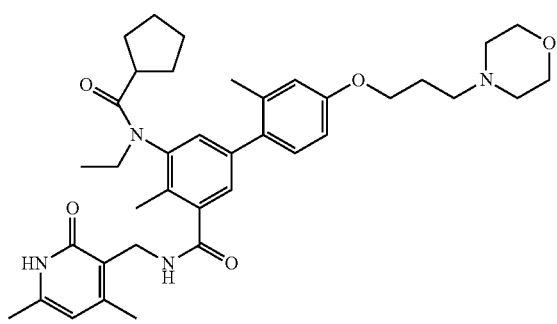
Compound 49
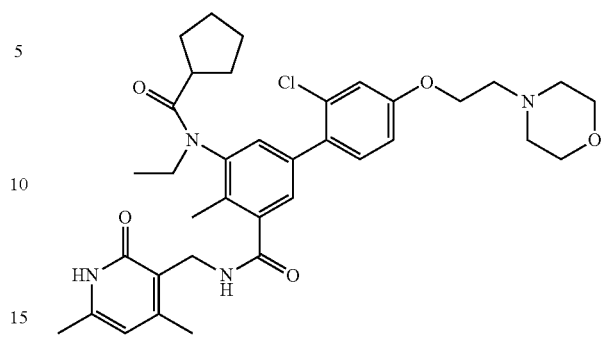
Compound 46
Compound 50
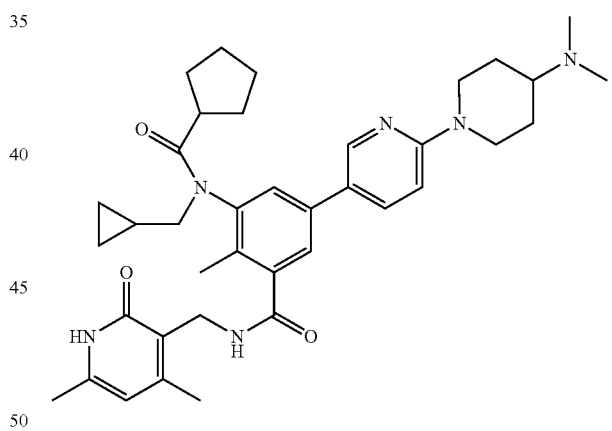
Compound 47
Compound 51
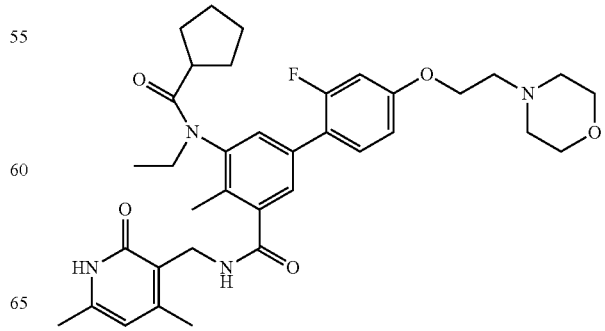

Compound 52
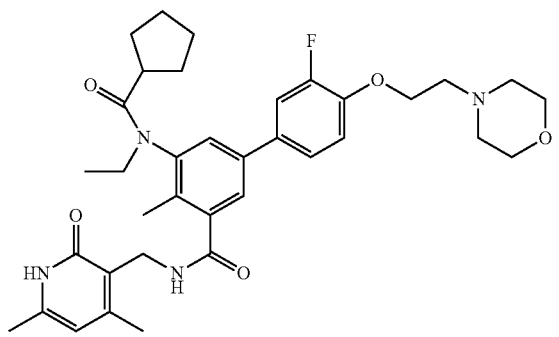
Compound 53
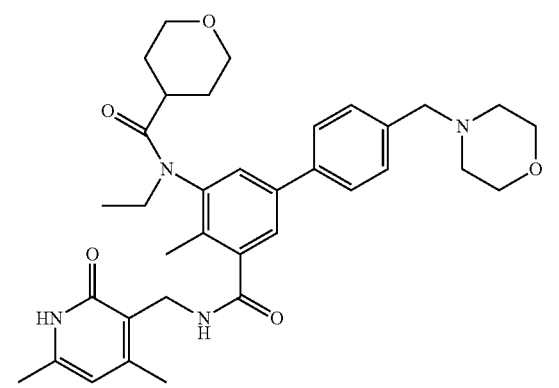
Compound 54
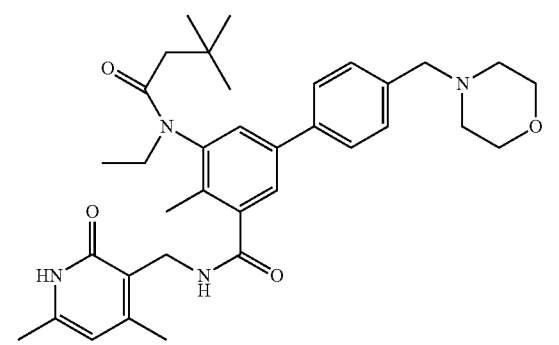
Compound 55
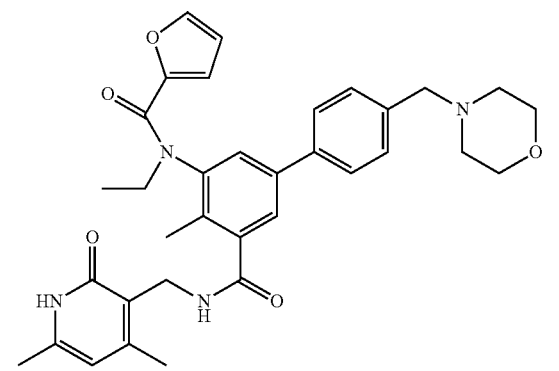
Compound 56
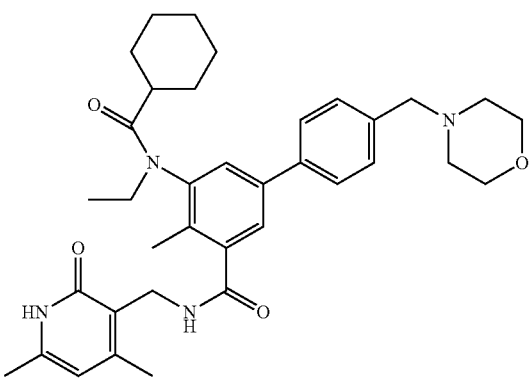
Compound 57
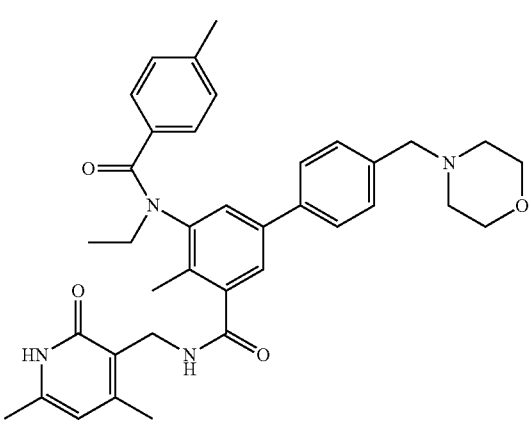
Compound 58
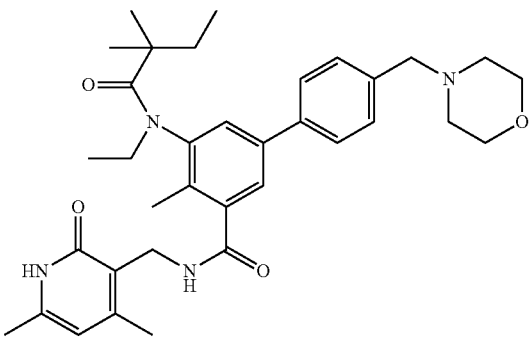
Compound 59
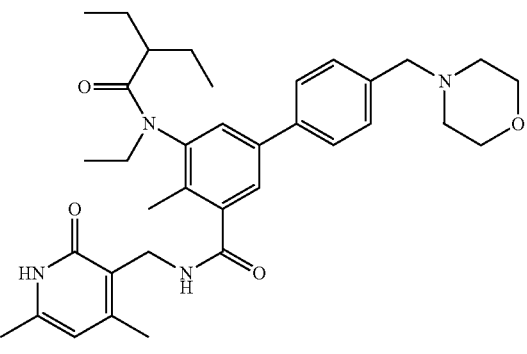

Compound 60
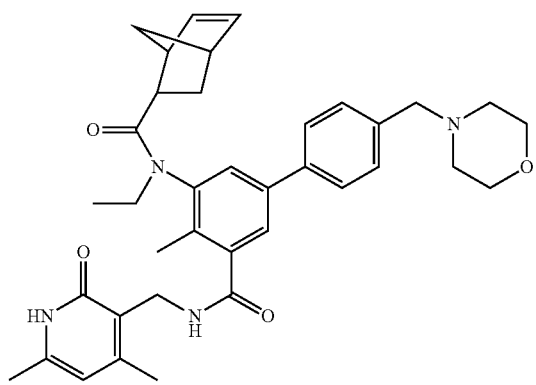
Compound 61
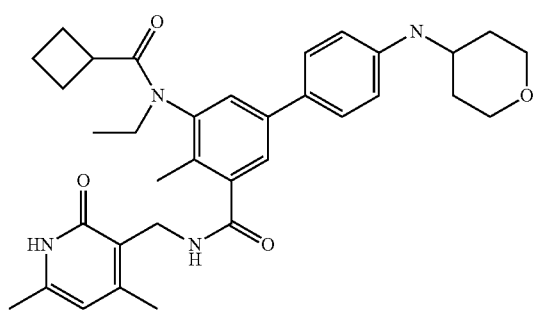
Compound 62
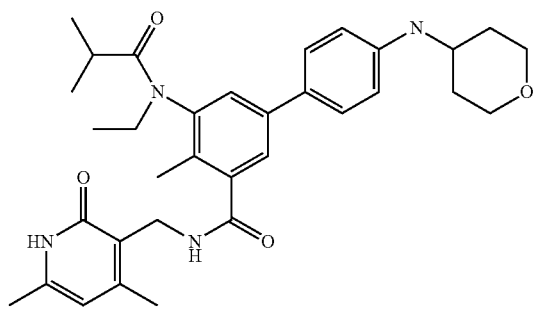
Compound 63
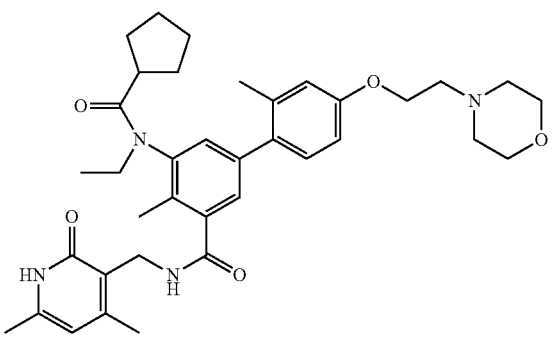
Compound 64
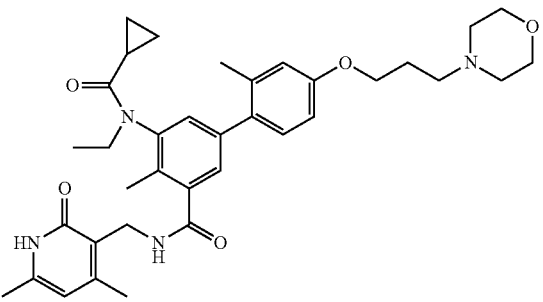
Compound 65
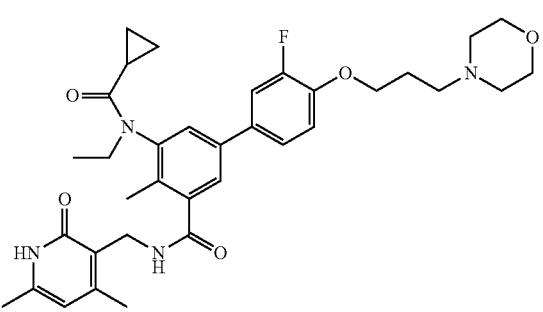
Compound 66
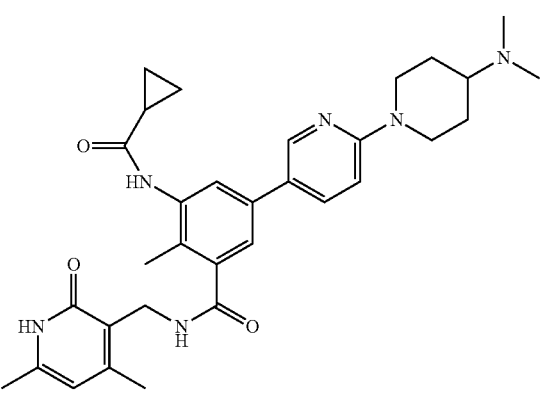
Compound 67
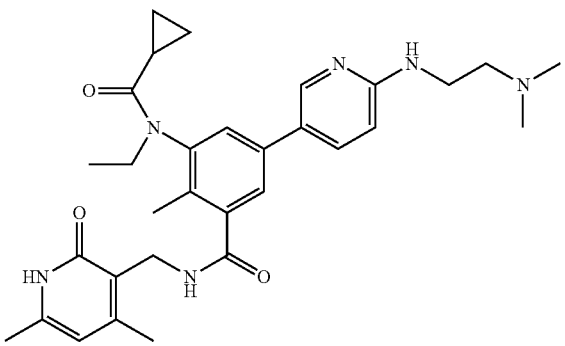

-continued
Compound 68
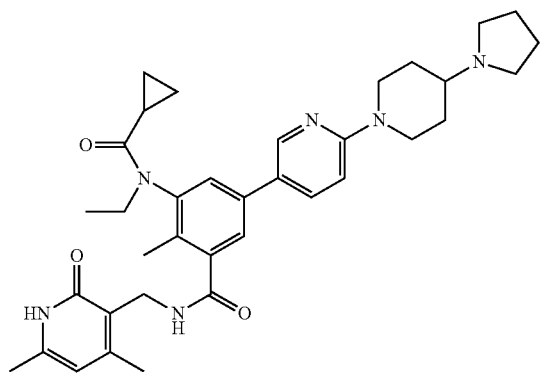
Compound 69
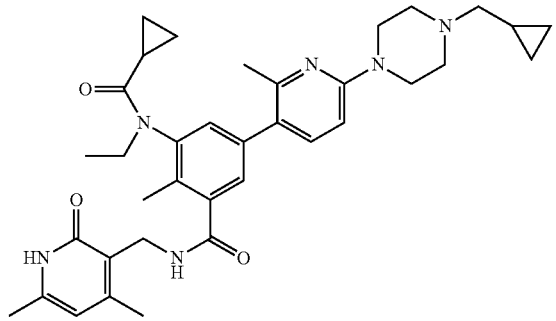
Compound 70
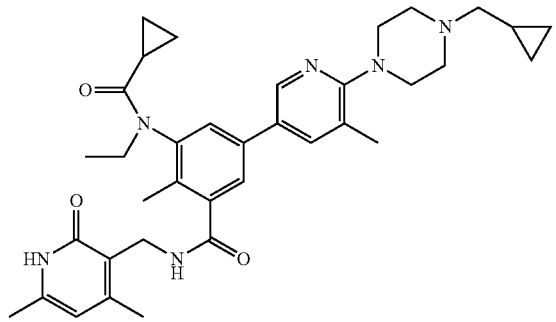
Compound 71
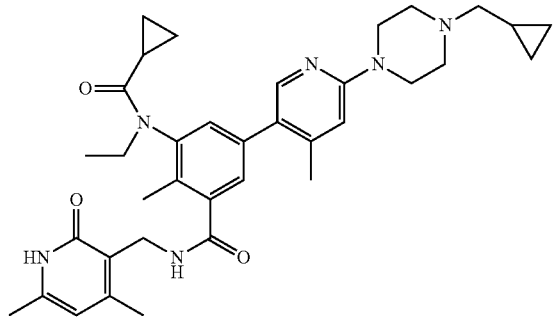
-continued
Compound 72
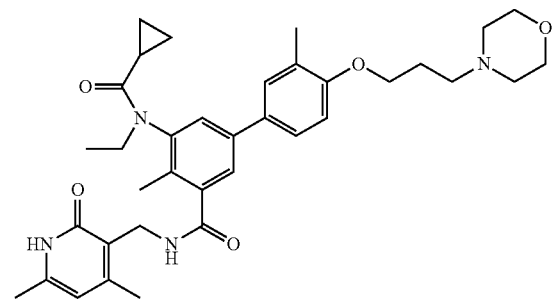
Compound 73
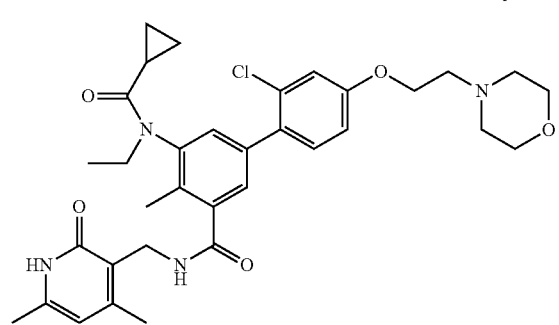
Compound 74
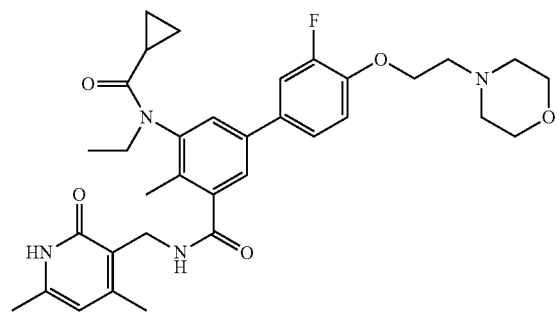
Compound 75
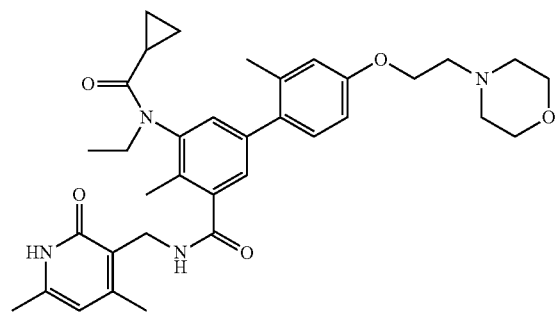

Compound 76
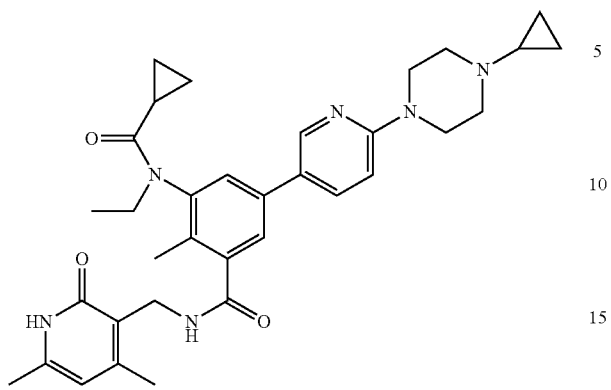
Compound 77
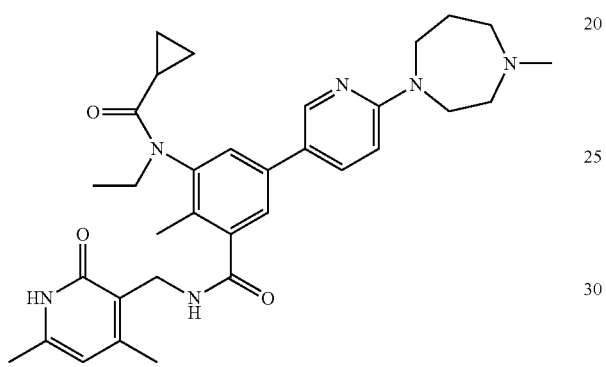
Compound 78
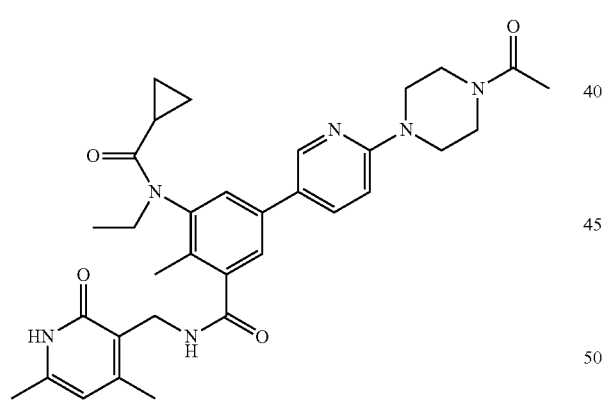
Compound 79
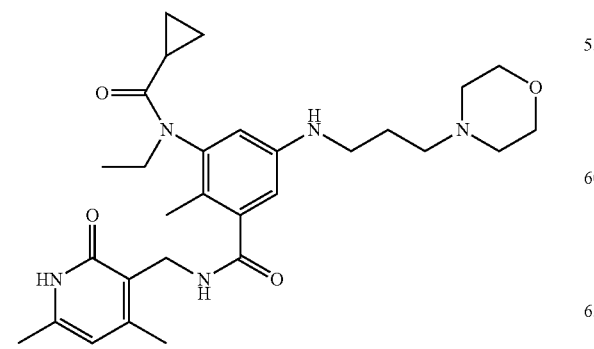
Compound 80
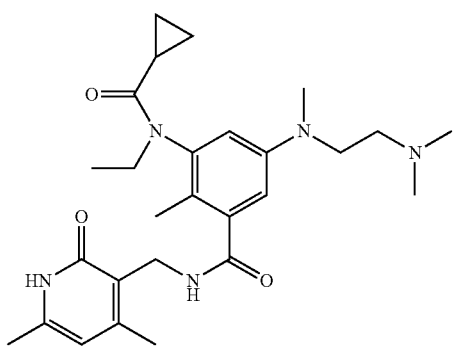
Compound 81
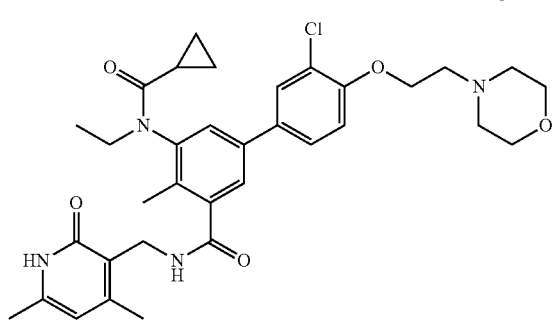
Compound 82
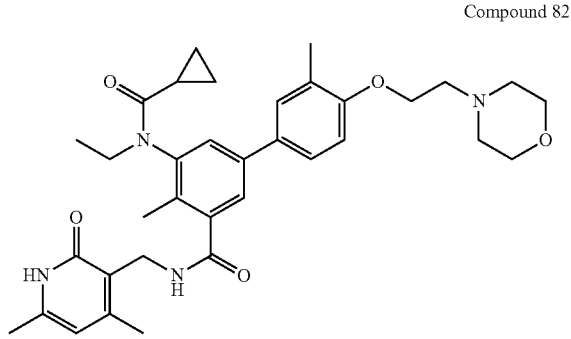
Compound 83
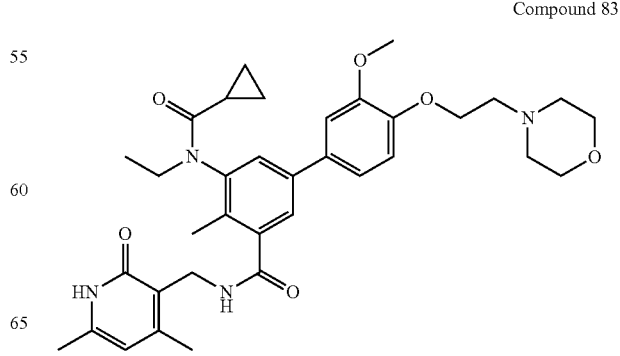

Compound 84
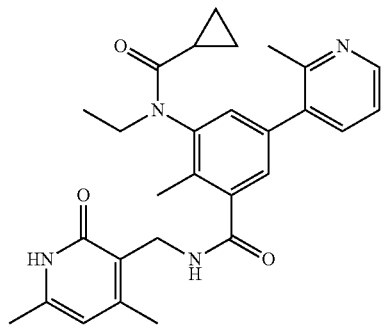
Compound 85
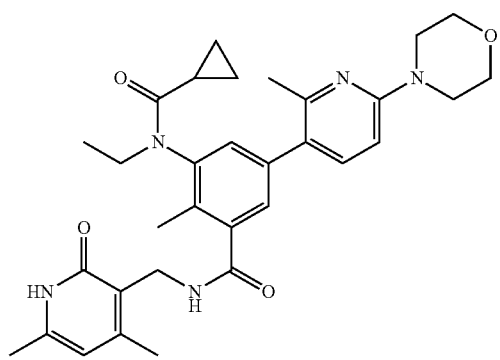
Compound 86
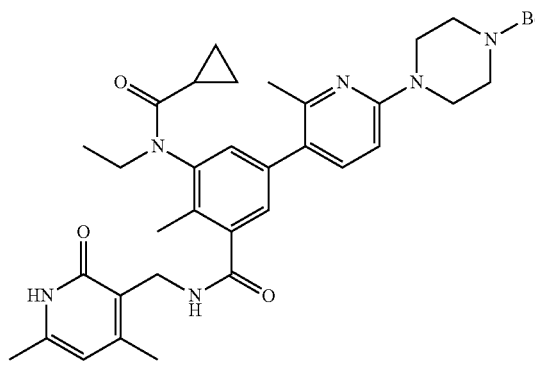
Compound 87
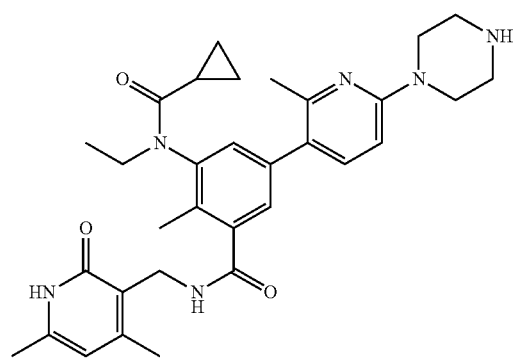
Compound 88
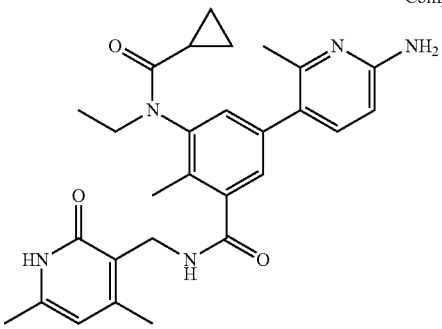
Compound 89
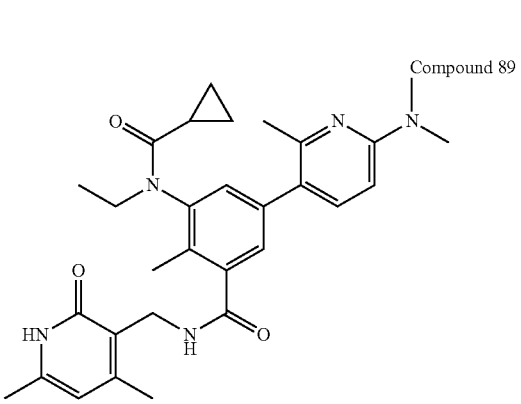
Compound 90
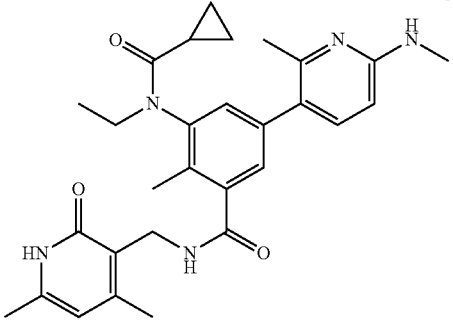
Compound 91
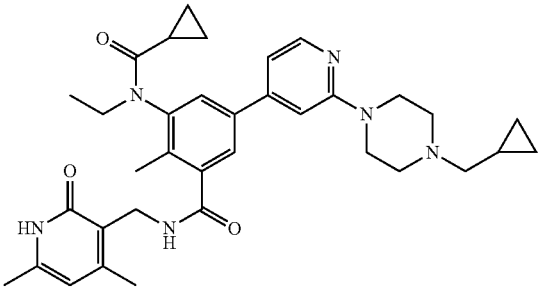

Compound 92

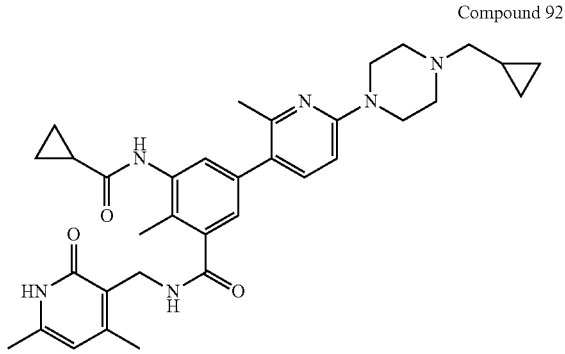 [SMILES: Cc1cc(C)c(CNC(=O)c2cc(-c3ccc(N4CCN(CC5CC5)CC4)nc3C)cc(NC(=O)C3CC3)c2C)c(=O)[nH]1]

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein Described herein are novel EZH2 (wild-type and/or Y641F mutant) inhibitors. The pharmaceutically acceptable salts, solvates, esters, acids, pharmaceutically active metabolites and prodrugs of these compounds are also described herein.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid-addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2]oct-2-ene-1-carboxylic acid, 2-naphthalenesulfonic acid, tert-butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base-addition salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

The chiral compounds involved in the present invention may be of any configuration or mixed racemates. When a compound useful in accordance with the invention contains more than one chiral center, it may exist in diastereoisomeric forms. The diastereoisomeric compounds may be separated by methods known to those skilled in the art (for example, chromatography or crystallization) and the individual enantiomers may be separated as described above. The present invention includes the use of various diastereoisomers of compounds useful in accordance with the invention, and mixtures thereof. Compounds useful in accordance with the invention may exist in different tautomeric forms or as different geometric isomers, and the present invention includes the use of each tautomer and/or geometric isomer of compounds useful in accordance with the invention, and mixtures thereof. Compounds useful in accordance with the invention may exist in zwitterionic form. The present invention includes the use of each zwitterionic form of compounds useful in accordance with the invention, and mixtures thereof.

It will be appreciated by those skilled in the art that certain protected derivatives of compounds of Formulae (I)-(II), which may be made prior to a final deprotection stage, may not possess pharmacological activity as such, but may, in certain instances, be administered orally or parenterally and thereafter metabolized in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. It will further be appreciated by those skilled in the art, that certain moieties, known to those skilled in the art as "pro-moieties" may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals, and ketals.

Additionally, the compounds of the present invention, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

The screening and characterization of the pharmaceutically acceptable salts, polymorphs and/or solvates may be accomplished using a variety of techniques including, but not limited to, thermal analysis, x-ray diffraction, spectroscopy, microscopy, and elemental analysis. The various spectroscopic techniques used include, but are not limited to, Raman, FTIR, UVIS, and NMR (liquid and solid state). The various microscopy techniques include, but are not limited to, IR microscopy and Raman microscopy.

Pharmaceutical Composition

One or more EXH2 inhibitors of the present invention may be administered to a human patient individually or in a form of a pharmaceutical composition, wherein the EXH2 inhibitors are mixed, in a dosage to treat or ameliorate the diseases or conditions described herein, with a suitable carrier or one or more excipients. These mixtures of EZH2 inhibitors can also be administered as a simple mixture or in a suitable formulated pharmaceutical composition to a patient. For example, one aspect of the present invention relates to a pharmaceutical composition which comprises a therapeutically effective dosage of a EZH2 inhibitor or a pharmaceutically acceptable salt, solvate, isomer, ester, acid, metabolite or prodrug thereof, and pharmaceutically acceptable carrier or excipient, as well as other therapeutic agents.

In the course of treatment, it may be used alone or in combination with one or more other therapeutic agents. Other therapeutic agents may be selected from the following: immunosuppressants (e.g., tacrolimus, cyclosporin, rapamycin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, fluoxyprednisolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), allergy vaccines, antihistamines, antileukotrienes, β-agonists, theophylline, anticholinergics, or other selective kinase inhibitors (e.g., mTOR inhibitors, c-Met inhibitors) or her2 antibodies. In addition, the other therapeutic agents may also be Rapamycin, Crizotinib, Tamoxifen, Raloxifene, Anastrozole, Exemestane, Letrozole, Herceptin™ (Trastuzumab), Gleevec™ (Imatinib), Taxol™ (Paclitaxel), Cyclophosphamide, Lovastatin, Minosine, Cytarabine, 5-Fluorouracil (5-FU), Methotrexate (MTX), Taxotere (Docetaxel), Zoladex™ (Goserelin), Vincristine, Vinblastine, Nocodazole, Teniposide, Etoposide, Gemzar™ (Gemcitabine), Epothilone, Navelbine, Camptothecin, Daunonibicin, Dactinomycin, Mitoxantrone, Amsacrine, Doxorubicin (Adriamycin), Epirubicin or Idarubicin. Alternatively, other therapeutic agents may be cytokines such as G-CSF (Granulocyte-Colony Stimulating Factor). Alternatively, other therapeutic agents may be used in combination for the same treatment regimen, including but not limited to, CMF (Cyclophosphamide, Methotrexate and 5-Fluorouracil), CAF (Cyclophosphamide, Adriamycin and 5-Fluorouracil), AC (Adriamycin and Cyclophosphamide), FEC (5-Fluorouracil, Epirubicin and Cyclophosphamide), ACT or ATC (Adriamycin, Cyclophosphamide and Paclitaxel) or CMFP (Cyclophosphamide, Methotrexate, 5-Fluorouracil and Prednisone).

Techniques for formulation and administration of EZH2 inhibitors may be found in references well known to one of ordinary skill in the art, such as Remington's "The Science and Practice of Pharmacy," 21st ed., Lippincott Williams & Wilkins 2005.

Suitable routes of administration may, for example, include oral, rectal, or intestinal administration; parenteral delivery, including intravenous, intramuscular, intraperitoneal, subcutaneous, or intramedullary injections, as well as intrathecal, direct intraventricular, or intraocular injections; topical delivery, including eyedrop and transdermal; and intranasal and other transmucosal delivery.

Alternatively, one may administer an EZH2 inhibitor in a local rather than a systemic manner, for example, via injection of the EZH2 inhibitor directly into an edematous site, often in a depot or sustained release formulation.

In one embodiment, an EZH2 inhibitor is administered by direct injection into a tumor or lymph node.

Furthermore, one may administer an EZH2 inhibitor in a targeted drug delivery system, for example, in a liposome coated with cancer cell-specific antibody.

The pharmaceutical compositions of the present invention may be manufactured, e.g., by conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active EZH2 inhibitors into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants are used in the formulation appropriate to the barrier to be permeated. Such penetrants are generally known in the art.

For oral administration, the EZH2 inhibitors can be formulated readily by combining the active EZH2 inhibitors with pharmaceutically acceptable carriers well known in the art. Such carriers enable the EZH2 inhibitors of the invention to be formulated as tablets, pills, dragees, capsules, liquids, gels, syrups, slurries, suspensions and the like, for oral ingestion by a patient to be treated. Pharmaceutical preparations for oral use can be obtained by combining the active EZH2 inhibitor with a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active EZH2 inhibitor doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active EZH2 inhibitors may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

For administration by inhalation, the EZH2 inhibitors for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the EZH2 inhibitor and a suitable powder base such as lactose or starch.

The EZH2 inhibitors can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active EZH2 inhibitors in water-soluble form. Additionally, suspensions of the active EZH2 inhibitors may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the EZH2 inhibitors to allow for the preparation of highly concentrated solutions.

Alternatively, the active ingredient may be in powder form for reconstitution before use with a suitable vehicle, e.g., sterile pyro gen-free water.

The EZH2 inhibitors may also be formulated in rectal compositions such as suppositories or retention enemas, e.g., containing conventional suppository bases, such as cocoa butter or other glycerides.

In addition to the formulations described previously, the EZH2 inhibitors may also be formulated as a depot preparation. Such long acting formulations may be administered by implantation (for example, subcutaneously or intramuscularly or by intramuscular injection). Thus, for example, the EZH2 inhibitors may be formulated with suitable polymeric or hydrophobic materials (for example as an emulsion in an acceptable oil) or ion exchange resins, or as sparingly soluble derivatives (for example, as a sparingly soluble salt).

Alternatively, other delivery systems for hydrophobic pharmaceutical EZH2 inhibitors may be employed. Liposomes and emulsions are examples of delivery vehicles or carriers for hydrophobic drugs. Certain organic solvents such as dimethysulf oxide also may be employed. Additionally, the EZH2 inhibitors may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the EZH2 inhibitors for a few weeks up to over 100 days. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include but are not limited to calcium carbonate, calcium phosphate, various sugars, starches, cellulose derivatives, gelatin, and polymers, such as polyethylene glycols.

Methods of Treatment and Use

Provided herein are methods of treating, preventing or alleviating a condition and disease, such as cancer and precancerous condition, the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation.

For example, one aspect of the invention relates to a method for treating or alleviating a symptom of cancer or precancerous condition, which comprises the step of administering to a subject having a cancer or a precancerous condition and expressing a wild-type and/or mutant EZH2 a therapeutically effective amount of an inhibitor of EZH2. Preferably, the inhibitor of EZH2 of the present invention is capable of treating a subject having a cancer or a precancerous condition and expressing a wild-type and/or Y641F mutant EZH2.

In an embodiment, the inhibitor inhibits histone methyltransferase activity of Y641F mutant EZH2. In an embodiment, the inhibitor selectively inhibits histone methyltransferase activity of Y641F mutant EZH2. Preferably, the cancer is selected from a group consisting of lymphoma of non-Hodgkin lymphoma, follicular lymphoma or diffuse large B-cell lymphoma (DLBCL). Alternatively, the cancer is leukemia (such as CML) or melanoma. The precancerous condition comprises but is not limited to myelodysplastic syndromes.

Diseases such as cancers can be treated by administration of modulators of protein (e.g., histone) methylation, e.g., modulators of histone methyltransferase, or histone demethylase enzyme activity. Histone methylation has been reported to be involved in aberrant expression of certain genes in cancers, and in silencing of neuronal genes in non-neuronal cells. Modulators described herein can be used to treat such diseases, i.e., to inhibit methylation of histones in affected cells.

Based at least on the fact that abnormal histone methylation has been found to be associated with certain cancers and precancerous conditions, a method for treating cancer or a precancerous condition with a wild-type and/or mutant EZH2 in a subject comprises administering to the subject in need thereof a therapeutically effective amount of a compound that inhibits methylation or restores methylation to roughly its level in counterpart normal cells. In one embodiment a method for treating cancer or a precancerous condition in a subject comprises administering to the subject in need thereof a therapeutically effective amount of a compound that inhibits conversion of unmethylated H3-K27 to monomethylated H3-K27 (H3-K27meI). In one embodiment a method for treating cancer or a precancerous condition in a subject comprises administering to the subject in need thereof a therapeutically effective amount of a compound that inhibits conversion of monomethylated H3-K27 (H3-K27meI) to dimethylated H3-K27 (H3-K27me2). In one embodiment a method for treating cancer or a precancerous condition in a subject comprises administering to the subject in need thereof a therapeutically effective amount of a compound that inhibits conversion of H3-K27me2 to trimethylated H3-K27 (H3-K27me3). In one embodiment a method for treating cancer or a precancerous condition in a subject comprises administering to the subject in need thereof a therapeutically effective amount of a compound that inhibits both conversion of H3-K27meI to H3-K27me2 and conversion of H3-K27me2 to H3-K27me3. It is important to note that disease-specific increase in methylation can occur at chromatin in key genomic loci in the absence of a global increase in cellular levels of histone or protein methylation. For example, it is possible for aberrant hypermethylation at key disease-relevant genes to occur against a backdrop of global histone or protein hypomethylation.

Modulators of methylation can be used for modulating cell proliferation, generally. For example, in some cases excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growth (cancer).

Exemplary cancers that may be treated include lymphomas, including but not limited to non-Hodgkin lymphoma, follicular lymphoma (FL) and diffuse large B-cell lymphoma (DLBCL); melanoma; and leukemia, including but not limited to CML. Exemplary precancerous condition includes myelodisplastic syndrome (MDS; formerly known as preleukemia).

Other cancers include Acute Lymphoblastic Leukemia; Acute Myeloid Leukemia; Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma, see Skin Cancer (non-Melanoma); Bile Duct Cancer, Extrahepatic; Bladder Cancer; Bone Cancer, osteosarcoma/Malignant Fibrous Histiocytoma; Brain Stem Glioma; Brain Tumor; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Burkitt's Lymphoma; Carcinoid Tumor; Carcinoid Tumor, Gastrointestinal; Carcinoma of Unknown Primary; Central Nervous System Lymphoma, Primary; Cerebellar Astrocytoma; Cervical Cancer; Childhood Cancers; Chronic Lymphocytic Leukemia; Chronic Myelogenous Leukemia; Chronic Myelogenous Leukemia, Hairy Cell; Chronic Myeloproliferative Disorders; Colon Cancer; Colorectal Cancer; Cutaneous T-Cell Lymphoma, see Mycosis Fungoides and Sezary Syndrome; Endometrial Cancer; Esophageal Cancer; Ewing's Family of Tumors; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Leukemia; Lip and Oral Cavity Cancer; Liver Cancer, Adult (Primary); Liver Cancer, Childhood (Primary); Lung Cancer, Non-Small Cell; Lung Cancer, Small Cell; Lymphoma, Primary Central Nervous System; Macroglobulinemia, Waldenstrom's; Malignant Fibrous Histiocytoma of Bone/Osteosarcoma; Medulloblastoma; Melanoma; Merkel Cell Carcinoma; Mesothelioma; Mesothelioma, Adult Malignant; Metastatic Squamous Neck Cancer with Occult Primary; Multiple Endocrine Neoplasia Syndrome; Multiple Myeloma; Multiple Myeloma/Plasma Cell Neoplasm Mycosis Fungoides; Myelodysplasia Syndromes; Myelodysplastic/Myeloproliferative Diseases; Myeloid Leukemia, Adult Acute; Myeloid Leukemia, Childhood Acute; Myeloproliferative Disorders, Chronic; Nasal Cavity and Paranasal Sinus Cancer; Nasopharyngeal Cancer; Neuroblastoma; Non-Hodgkin's Lymphoma; Non-Hodgkin's Lymphoma During Pregnancy; Oral Cancer; Oral Cavity Cancer, Lip and Oropharyngeal Cancer; Osteosarcoma/Malignant Fibrous Histiocytoma of Bone; Ovarian Cancer; Ovarian Epithelial Cancer; Ovarian Low Malignant Potential Tumor; Pancreatic Cancer; Pancreatic Cancer, Islet Cell; Paranasal Sinus and Nasal Cavity Cancer; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Prostate Cancer; Rectal Cancer; Retinoblastoma; Rhabdomyosarcoma; Salivary Gland Cancer; Sarcoma, Ewing's Family of Tumors; Sarcoma, Soft Tissue; Sarcoma, Uterine; Sezary Syndrome; Skin Cancer; Skin Cancer (non-Melanoma); Small Intestine Cancer; Soft Tissue Sarcoma; Squamous Cell Carcinoma, see Skin Cancer (non-Melanoma); Squamous Neck Cancer with Occult Primary, Metastatic; Testicular Cancer; Thymoma; Thymoma and Thymic Carcinoma; Thyroid Cancer; Transitional Cell Cancer of the Renal Pelvis and Ureter; Trophoblastic Tumor, Gestational; Unknown Primary Site, Cancer of; Unusual Cancers of Childhood; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; Wilms' Tumor; and Women's Cancers.

Combination Therapy

In one aspect of the invention, an EZH2 inhibitor, or a pharmaceutically acceptable salt thereof, can be used in combination with another therapeutic agent to treat diseases such as cancer. For example, the additional agent can be a therapeutic agent that is art-recognized as being useful to treat the disease or condition being treated by the compound of the present invention.

The combination therapy contemplated by the invention includes, for example, administration of a compound of the invention, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

The agents set forth below are for illustrative purposes and not intended to be limiting. The combinations, which are part of this invention, can be the compounds of the present invention and at least one additional agent selected from the lists below. The combination can also include more than one additional agent, e.g., two or three additional agents if the combination is such that the formed composition can perform its intended function.

For example, one aspect of the invention relates to the use of an EZH2 inhibitor in combination with another agent for the treatment of cancer. In one embodiment, an additional agent is an anticancer agent that is a compound that affects histone modifications, such as an HDAC inhibitor. In certain embodiments, an additional anticancer agent is selected from the group consisting of chemotherapetics (such as 2CdA, 5-FU, 6-Mercaptopurine, 6-TG, Abraxane™, Actinomycin-D, all-trans retinoic acid, amethopterin, Ara-C, Azacitadine, BCNU, Clofarabine, Clolar™, daunorubicin hydrochloride, DIC, etoposide phosphate, hexamethylmelamine, ixabepilone, L-asparaginase, liposomal Ara-C, L-PAM, Lysodren, mithracin, Mitomycin-C, nilotinib, Nitrogen Mustard, prolifeprospan 20 with carmustine implant, TESPA, Vidaza™, vincristine sulfate, VM 26); biologies (such as Alpha Interferon, *Bacillus* Calmette-Guerin, Erlotinib, Interleukin-2, lenalidomide, Tarceva™, and Zevalin™); corticosteroids (such as dexamethasone sodium phosphate); hormonal therapies (such as Plenaxis™); and radiopharmaceuticals (such as Samarium SM-153); as well as other therapeutic agents listed in the above section of "Pharmaceutical composition".

Dosage

As used herein, a "therapeutically effective amount" or "therapeutically effective dose" is an amount of an EZH2 inhibitor or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. In one embodiment, a therapeutically effective dose refers to that amount of the EZH2 inhibitors that result in amelioration of symptoms in a patient. For a given patient, a therapeutically effective amount may be determined by methods known to those of skill in the art.

Toxicity and therapeutic efficacy of EZH2 inhibitors can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. Dosage may also be guided by monitoring the EZH2 inhibitor's effect on pharmacodynamic markers of enzyme inhibition (e.g., histone methylation or target gene expression) in diseased or surrogate tissue. Cell culture or animal experiments can be used to determine the relationship between doses required for changes in pharmacodynamic markers and doses required for therapeutic efficacy can be determined in cell culture or animal experiments or early stage clinical trials. The dosage of such EZH2 inhibitors lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. In the treatment of crises, the administration of an acute bolus or an infusion approaching the MTD may be required to obtain a rapid response.

Dosage amount and interval may be adjusted individually to provide plasma levels of the active moiety which are sufficient to maintain the methyltransferase modulating effects, or minimal effective concentration (MEC) for the required period of time to achieve therapeutic efficacy. The MEC will vary for each EZH2 inhibitor but can be estimated from in vitro data and animal experiments. Dosages necessary to achieve the MEC will depend on individual characteristics and route of administration. However, high pressure liquid chromatography (HPLC) assays or bioassays can be used to determine plasma concentrations.

Dosage intervals can also be determined using the MEC value. In certain embodiments, EZH2 inhibitors should be administered using a regimen which maintains plasma levels above the MEC for 10-90% of the time, preferably between 30-90% and most preferably between 50-90% until the desired amelioration of symptoms is achieved. In other embodiments, different MEC plasma levels will be maintained for differing amounts of time. In cases of local administration or selective uptake, the effective local concentration of the drug may not be related to plasma concentration.

One of skill in the art can select from a variety of administration regimens and the amount of EZH2 inhibitor administered will, of course, be dependent on the subject being treated, on the subject's weight, the severity of the affliction, the manner of administration and the judgment of the prescribing physician. But the administration amount can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Kits

An EZH2 inhibitor may, if desired, be presented in a kit (e.g., a pack or dispenser device) which may contain one or more unit dosage forms containing the EZH2 inhibitor. The pack may for example comprise metal or plastic foil, such as a blister pack. The pack or dispenser device may be accompanied by instructions for administration. Compositions comprising an EZH2 inhibitor of the invention formulated in a compatible pharmaceutical carrier may also be prepared, placed in an appropriate container, and labeled for treatment of an indicated condition. Instructions for use may also be provided.

Also provided herein are kits comprising a plurality of methylation detection reagents that detect the methylated H3-K27. For example, the kit includes mono-methylated H3-K27, di-methylated H3-K27 and tri-methylated H3-K27 detection reagents. The detection reagent is for example antibodies or fragments thereof, polypeptide or aptamers.

The kit may contain in separate containers an aptamer or an antibody, control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Western Blot analysis, Immunohistochemistry (IHC), immunofluorescence (IF), sequencing and Mass spectrometry (MS) as known in the art.

Preparation of Compounds

Compounds of the invention may be synthesized using standard synthetic techniques known to those of skill in the art or using methods known in the art in combination with methods described herein. In addition, solvents, temperatures and other reaction conditions presented herein may vary according to those of skill in the art. As a further guide the following synthetic methods may also be utilized.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5$^{th}$ edition, John Wiley & Sons: New York, 2001; and Greene, T. W., Wuts, P. G. M., Protective Groups in Organic Synthesis, 3 edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention. Compounds of the present invention can be conveniently prepared by a variety of methods familiar to those skilled in the art. The compounds of this invention with each of the formulae described herein may be prepared according to the following procedures from commercially available starting materials or starting materials which can be prepared using literature procedures. These procedures show the preparation of representative compounds of this invention.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

EXAMPLES

The invention now being generally described, will be more readily understood by reference to the following examples, which are included merely for purposes of illustrating embodiments of certain aspects of the present invention, and are not intended to limit the scope of the invention in any way.

Example 1

N-((4,6-dimethyl-2-oxo-1,2-dihydropyridin-3-yl)methyl)-5-(6-(4-(dimethylamino)piperidin-1-yl)pyridin-3-yl)-3-(N-ethylcyclopropanecarboxamido)-2-methylbenzamide 1

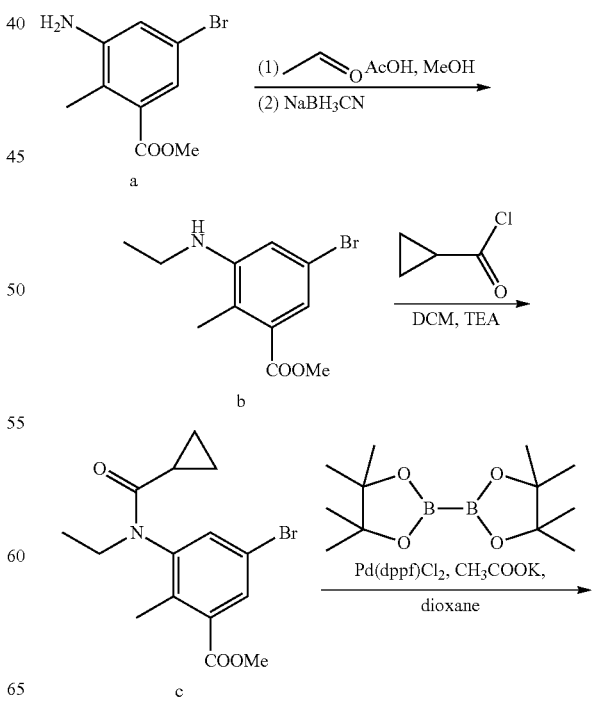

-continued

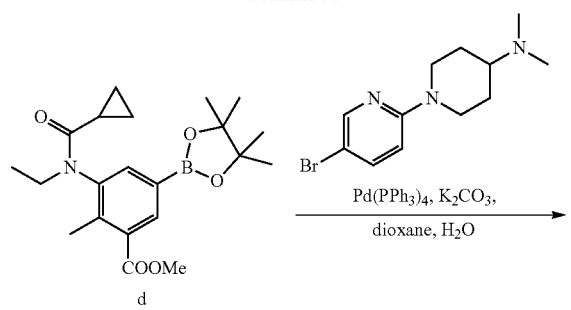

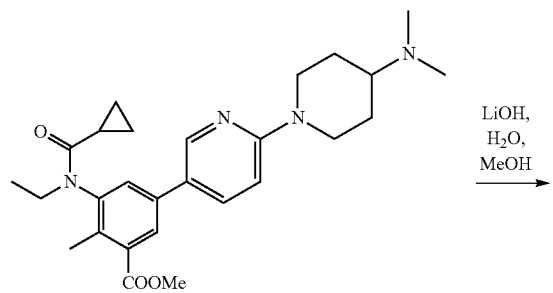

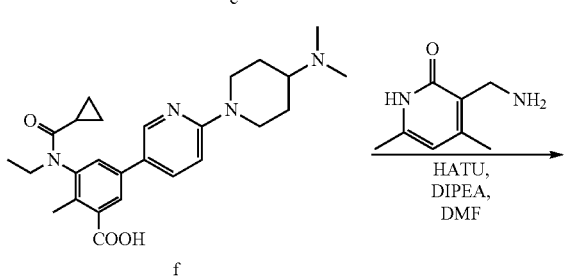

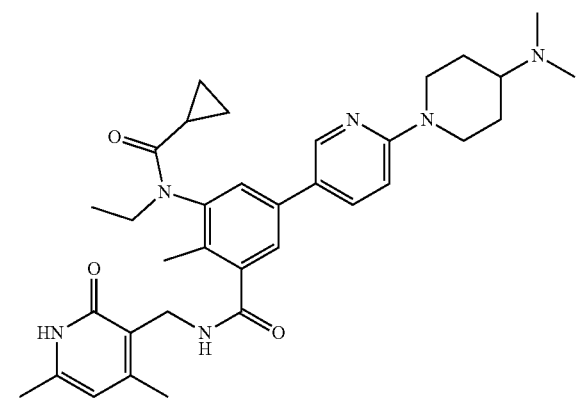

-continued

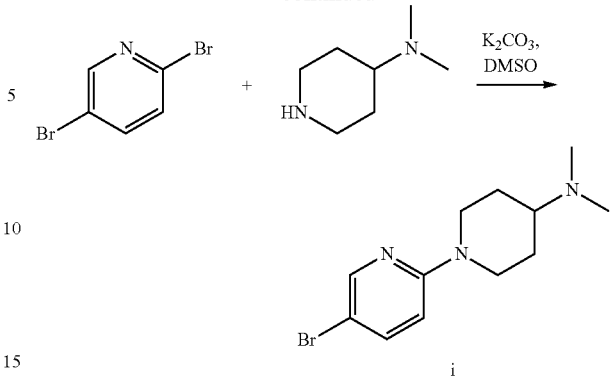

Synthesis of Compound b:

Compound a: 3-amino-5-bromo-2-methylmethylbenzoate (5 g, 1.0 eq), and acetic acid (3.51 ml, 3.0 eq) were added into methanol (30 ml), and acetaldehyde (1.26 ml, 1.1 eq) was added under ice bath. After stirring for 2 hours at room temperature, sodium cyanoborohydride (2.57 g, 2.0 eq) was added under ice bath. After 1-hour stirring, saturated sodium bicarbonate was add until no generation of bubbles. The resultant was subjected to concentration and dilution with ethyl acetate and water. The organic layer was subjected successively to washing with water (3×30 ml) and with saturated saline (30 ml), then was dried with anhydrous sodium sulfate, subjected to concentration and column chromatography, yielding solid b (3.8 g).

Synthesis of Compound c:

Compound b: 5-bromo-3-(ethylamino)-2-methylmethylbenzoate, (3 g, 1.0 eq) and triethylamine (12 ml, 8.0 eq) was added into dichloromethane (30 ml). Cyclopropanecarbonyl chloride (4 ml, 4.0 eq) was added under ice bath and the mixture was stirred at room temperature for 10 minutes. Quenching was performed by adding saturated sodium bicarbonate, and the resultant was subjected to direct extraction with the organic layer being subjected to washing with saturated sodium bicarbonate (3×30 ml), and saturated saline (30 ml), then was dried with anhydrous sodium sulfate, subjected to concentration and column chromatography, yielding solid c (3.1 g).

Synthesis of Compound d:

Compound c: 5-bromo-3-(N-ethylcyclopropanecarboxamido)-2-methylmethylbenzoate (3 g, 1.0 eq), bis(pinacolato)diboron (4.5 g, 2.0), potassium acetate (2.4 g, 2.5 eq), and Pd(dppf)Cl$_2$ (0.36 g, 0.05 eq) was mixed and added into 1,4-dioxane (20 ml), and the mixture was stirred overnight under the protection of nitrogen at 100° C., and then subjected to concentration and column chromatography, yielding solid d (2.7 g).

Synthesis of Compound i:

Compound 2,5-dibromopyridine (200 mg, 1.0 eq), N,N-dimethylpiperidin-4-amine (160 mg, 1.1 eq) and potassium carbonate (470 mg, 3.0 eq) was mixed and added into DMSO (10 ml), and the mixture was stirred overnight under the protection of nitrogen at 100° C., and then diluted with water and extracted with ethyl acetate. The resultant organic phase was subjected to washing with water three times and with saturated saline, and to drying with anhydrous sodium sulfate, yielding solid i (300 mg), for which no further purification is required.

Synthesis of Compound e:

Compound d: 3-(N-ethylcyclopropanecarboxamido)-2-methyl-5-(4,4,5,5-tetramethyl-1,3,2-dioxaborolane-2-yl)

methylbenzoate (100 mg, 1 eq), Compound i 1-(5-bromopyridin-2-yl)-N,N-dimethylpiperidin-4-amine (73 mg, 1.0 eq), Pd(PPh$_3$)$_4$ (15 mg, 0.05 eq) and potassium carbonate (53 mg, 1.5 eq) was mixed and added into 1,4-dioxane/water (5 ml/0.5 ml), and the mixture was stirred overnight under the protection of nitrogen at 110° C., and then subjected to concentration and column chromatography to yield solid e (85 mg).

Synthesis of Compound f:

Compound e 5-(6-(4-(dimethylamino)piperidin-1-yl)pyridin-3-yl)-3-(N-ethylcyclopropanecarboxamido)-2-methyl-methylbenzoate (80 mg, 1.0 eq) and lithium hydrate (39 mg, 10 eq) was mixed and dissolved in methanol/water (10 ml/3 ml), and the mixture was stirred at room temperature for 2 hours with pH adjusted to 6 with 1M HCl, concentrated and then diluted with addition of water, extracted twice with n-butanol, and dried and concentrated to yield product f (60 mg), for which no further purification is required.

Synthesis of Compound g:

3-oxo-butyronitrile (5.04, 1.05 eq) and potassium tert-butoxide (7 g, 1.05 eq) was mixed and added into DMSO (80 ml), and after stirring of the mixture at room temperature for 10 minutes, (E)-3-penten-2-one (5 g, 1 eq) was added. The mixture was stirred at room temperature for half an hour, added again with potassium tert-butoxide (7 g, 1.05 eq), and after 1 hour stirred overnight with aeration of air. The reaction liquid was cooled to 0° C., diluted with addition of 20 ml of water, added dropwise with 4N HCl (15 ml), stirred for 15 minutes and then filtered to obtain solids, which were subjected to washing with 100 ml of water to obtain product g (3.8 g), for which no further purification is required.

Synthesis of Compound h:

Compound g: 4,6-dimethyl-2-oxo-1,2-dihydropyridin-3-nitril (3 g, 1.0 eq) and a suitable amount of raney nickel was added into methanol (50 ml), and then added with saturated ammonia (25 ml). The mixture was allowed for reaction for 24 hours under an atmosphere containing hydrogen, and then filtered, concentrated, and crystallized to obtain 2.0 g of product h.

Synthesis of Compound 1:

Compound f: 5-(6-(4-(dimethylamino)piperidin-1-yl)pyridin-3-yl)-3-(N-ethylcyclopropanecarboxamido)-2-methylbenzoic acid (25 mg, 1.0 eq) was dissolved in DMF (3 ml), and the mixture was added successively with DIPEA (0.029 ml, 3 eq), HATU (32 mg, 1.5 eq), Compound h 3-(aminomethyl)-4,6-dimethylpyridin-2(1H)-one (9.3 mg, 1.1 eq), and the mixture was stirred for 1 hour at room temperature, diluted by addition of water, and extracted with ethyl acetate. The extracted organic phase was subjected to washing with water three times and with saturated saline, then to drying with anhydrous sodium sulfate, and further to concentration and column chromatography to yield solid products 1 (15 mg).

Mass spectrometric data: LC-MS (ESI, m/z): 585.3542 [M+H]$^+$.

Example 2

5-(6-(4-(dimethylamino)piperidin-1-yl)pyridin-3-yl)-3-(N-ethylcyclopropane carboxamido)-2-methyl-N-((6-methyl-2-oxo-4-propyl-1,2-dihydropyridin-3-yl)methyl)benzamide 2

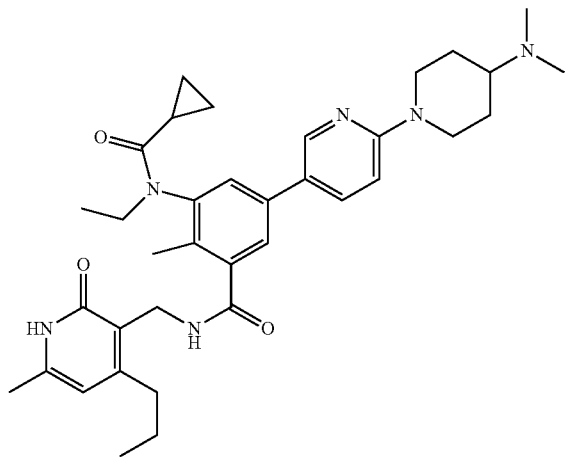

Synthesis of compound 2 was accomplished by using procedures similar to those described in Example 1.

Mass spectrometric data: LC-MS (ESI, m/z): 613.3854 [M+H]$^+$.

Example 3

5-(6-(4-(cyclopropylmethyl)piperazin-1-yl)pyridin-3-yl)-N-((4,6-dimethyl-2-oxo-1,2-dihydropyridin-3-yl)methyl)-3-(N-ethylcyclopropanecarboxamido)-2-methylbenzamide 3

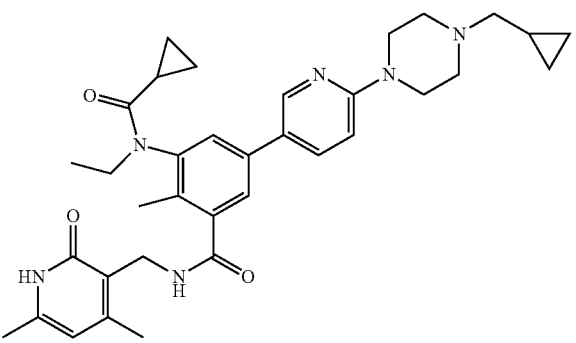 [SMILES: CCN(C(=O)C1CC1)c1cc(-c2ccc(N3CCN(CC4CC4)CC3)nc2)cc(C(=O)NCc2c(C)cc(C)[nH]c2=O)c1C]

Synthesis of compound 3 was accomplished by using procedures similar to those described in Example 1.

Mass spectrometric data: LC-MS (ESI, m/z): 597.3545 [M+H]$^+$.

Example 4

5-(6-(4-(cyclopropylmethyl)piperazin-1-yl)pyridin-3-yl)-3-(N-ethylcyclopropanecarboxamido)-2-methyl-N-((6-methyl-2-oxo-4-propyl-1,2-dihydropyridin-3-yl)methyl)benzamide 4

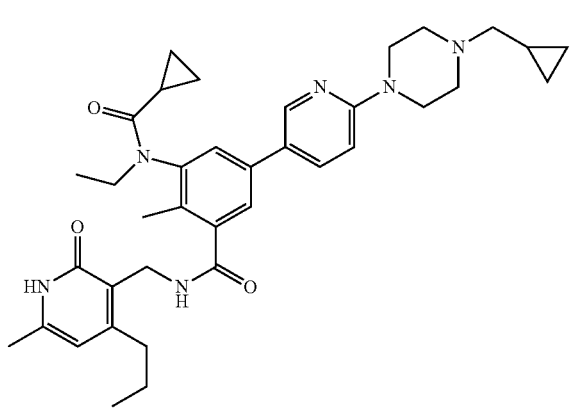 [SMILES: CCCc1cc(C)[nH]c(=O)c1CNC(=O)c1cc(-c2ccc(N3CCN(CC4CC4)CC3)nc2)cc(N(CC)C(=O)C2CC2)c1C]

Synthesis of compound 4 was accomplished by using procedures similar to those described in Example 1.

Mass spectrometric data: LC-MS (ESI, m/z): 625.3849 [M+H]$^+$.

Example 5

N-((4,6-dimethyl-2-oxo-1,2-dihydropyridin-3-yl)methyl)-5-(N-ethylcyclopropanecarboxamido)-4-methyl-4'-(morpholinomethyl)-[1,1'-diphenyl]-3-carboxamide

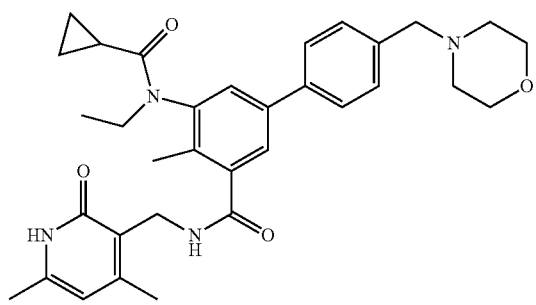 [SMILES: CCN(C(=O)C1CC1)c1cc(-c2ccc(CN3CCOCC3)cc2)cc(C(=O)NCc2c(C)cc(C)[nH]c2=O)c1C]

Synthesis of compound 5 was accomplished by using procedures similar to those described in Example 1.

Mass spectrometric data: LC-MS (ESI, m/z): 557.3132 [M+H]$^+$.

Example 6

N-((4,6-dimethyl-2-oxo-1,2-dihydropyridin-3-yl)methyl)-5-(N-ethylcyclopropanecarboxamido)-4-methyl-4'-morpholinyl-[1,1'-diphenyl]-3-carboxamide 6

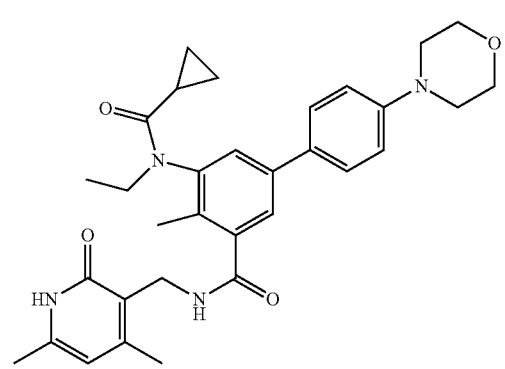 [SMILES: CCN(C(=O)C1CC1)c1cc(-c2ccc(N3CCOCC3)cc2)cc(C(=O)NCc2c(C)cc(C)[nH]c2=O)c1C]

Synthesis of compound 6 was accomplished by using procedures similar to those described in Example 1.

Mass spectrometric data: LC-MS (ESI, m/z): 543.2960 [M+H]$^+$.

Example 7

N-((4,6-dimethyl-2-oxo-1,2-dihydropyridin-3-yl)methyl)-3-(N-ethylcyclopropanecarboxamido)-2-methyl-5-(6-morpholinopyridin-3-yl)benzamide 7

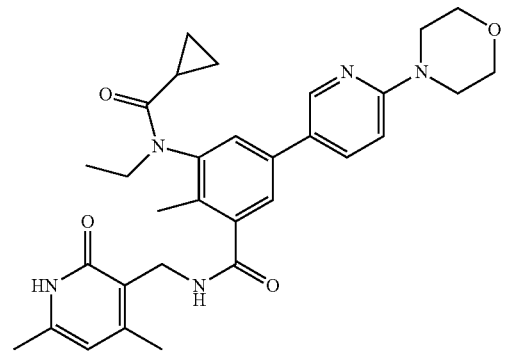 [SMILES: CCN(C(=O)C1CC1)c1cc(-c2ccc(N3CCOCC3)nc2)cc(C(=O)NCc2c(C)cc(C)[nH]c2=O)c1C]

Synthesis of compound 7 was accomplished by using procedures similar to those described in Example 1.

Mass spectrometric data: LC-MS (ESI, m/z): 544.2910 [M+H]$^+$.

Example 8

N-((4,6-dimethyl-2-oxo-1,2-dihydropyridin-3-yl)methyl)-5-(N-ethylcyclopropanecarboxamido)-4'-(4-ethylpiperazin-1-yl)-4-methyl-[1,1'-diphenyl]-3-carboxamide 8

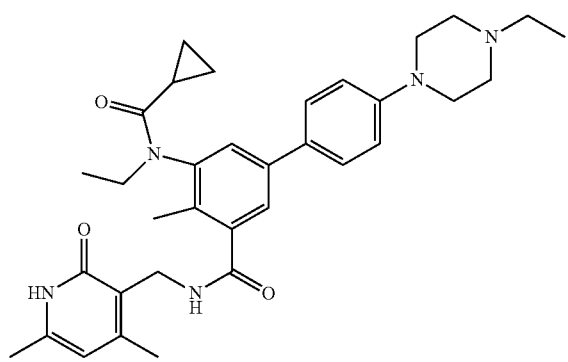 [SMILES: CCN1CCN(c2ccc(-c3cc(C(=O)NCc4c(C)cc(C)[nH]c4=O)c(C)c(N(CC)C(=O)C4CC4)c3)cc2)CC1]

Synthesis of compound 8 was accomplished by using procedures similar to those described in Example 1.

Mass spectrometric data: LC-MS (ESI, m/z): 570.3422 [M+H]$^+$.

Example 9

N-((4,6-dimethyl-2-oxo-1,2-dihydropyridin-3-yl)methyl)-3-(N-ethylcyclopropanecarboxamido)-2-methyl-5-(6-(4-methylpiperazin-1-yl)pyridin-3-yl)benzamide 9

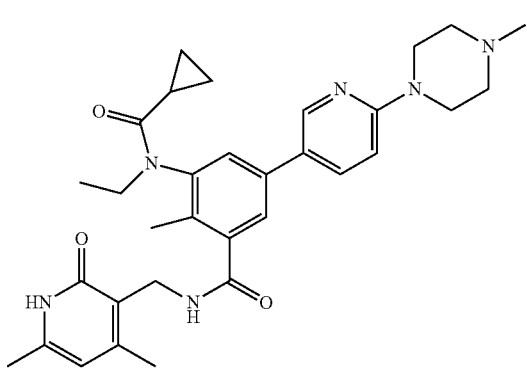

Synthesis of compound 9 was accomplished by using procedures similar to those described in Example 1.

Mass spectrometric data: LC-MS (ESI, m/z): 557.3251 [M+H]$^+$.

Example 10

N-((4,6-dimethyl-2-oxo-1,2-dihydropyridin-3-yl)methyl)-3-(N-ethylcyclopropanecarboxamido)-5-(6-(4-isopropylpiperazin-1-yl)pyridin-3-yl)-2-methylbenzamide 10

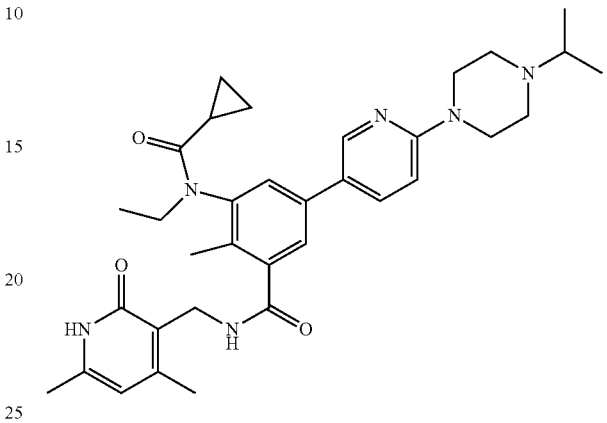

Synthesis of compound 10 was accomplished by using procedures similar to those described in Example 1.

Mass spectrometric data: LC-MS (ESI, m/z): 585.3542 [M+H]$^+$.

Example 11

N-((4,6-dimethyl-2-oxo-1,2-dihydropyridin-3-yl)methyl)-4'-((4-(dimethylamino)piperidin-1-yl)methyl)-5-(N-ethylcyclopropanecarboxamido)-4-methyl-[1,1'-diphenyl]-3-carboxamide 11

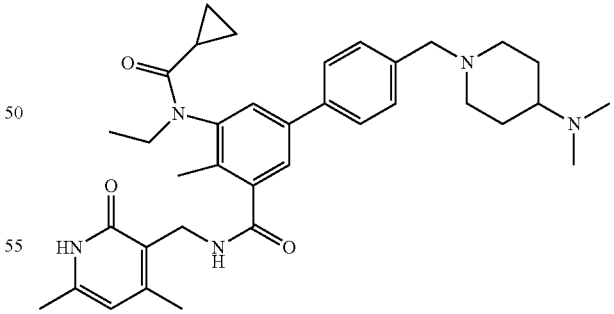

Synthesis of compound 11 was accomplished by using procedures similar to those described in Example 1.

Mass spectrometric data: LC-MS (ESI, m/z): 598.3772 [M+H]$^+$.

Example 12

N-((4,6-dimethyl-2-oxo-1,2-dihydropyridin-3-yl)methyl)-5-(6-((2-(dimethylamino)ethyl)(methyl)amino)pyridin-3-yl)-3-(N-ethylcyclopropanecarboxamido)-2-methylbenzamide 12

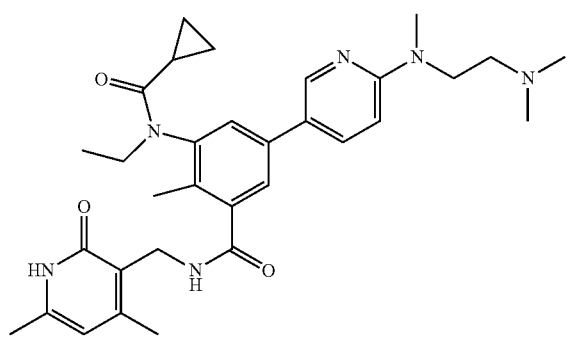

Synthesis of compound 12 was accomplished by using procedures similar to those described in Example 1.

Mass spectrometric data: LC-MS (ESI, m/z): 559.3390 [M+H]$^+$.

Example 13

N-((4,6-dimethyl-2-oxo-1,2-dihydropyridin-3-yl)methyl)-3-(N-ethylcyclopropanecarboxamido)-2-methyl-5-((2-morpholinoethyl)amino)-benzamide 13

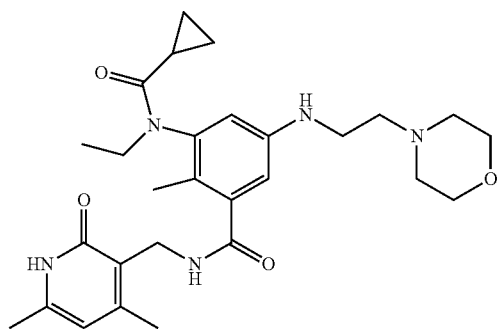 [SMILES: CCN(C(=O)C1CC1)c1cc(NCCN2CCOCC2)cc(C(=O)NCc2c(C)cc(C)[nH]c2=O)c1C]

Synthesis of compound 13 was accomplished by using procedures similar to those described in Example 1.

Mass spectrometric data: LC-MS (ESI, m/z): 510.3058 [M+H]$^+$.

Example 14

N-((4,6-dimethyl-2-oxo-1,2-dihydropyridin-3-yl)methyl)-5-(6-(4-(dimethylamino)piperidin-1-yl)pyridin-3-yl)-3-(N-ethylcyclopentanecarboxamido)-2-methylbenzamide 14

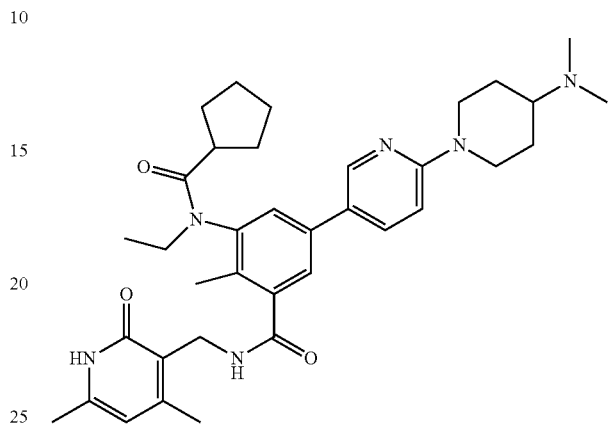

Synthesis of compound 14 was accomplished by using procedures similar to those described in Example 1.

Mass spectrometric data: LC-MS (ESI, m/z): 613.3864 [M+H]$^+$.

Example 15

5-(6-(4-(cyclopropylmethyl)piperazin-1-yl)pyridin-3-yl)-N-((4,6-dimethyl-2-oxo-1,2-dihydropyridin-3-yl)methyl)-3-(N-ethylcyclopentanecarboxamido)-2-methylbenzamide 15

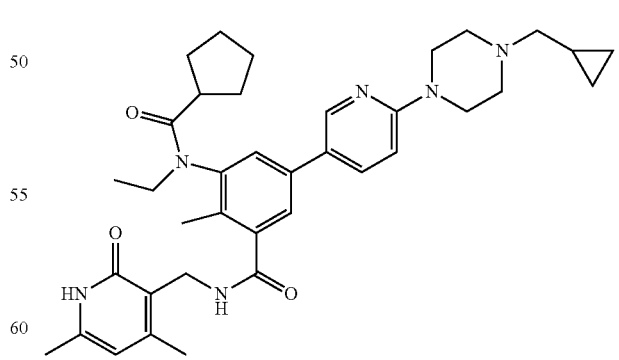

Synthesis of compound 15 was accomplished by using procedures similar to those described in Example 1.

Mass spectrometric data: LC-MS (ESI, m/z): 625.3862 [M+H]$^+$.

Example 16

N-((4,6-dimethyl-2-oxo-1,2-dihydropyridin-3-yl)methyl)-5-(N-ethylcyclopentanecarboxamido)-4-methyl-4'-(morpholinomethyl)-[1,1'-diphenyl]-3-carboxamide 16

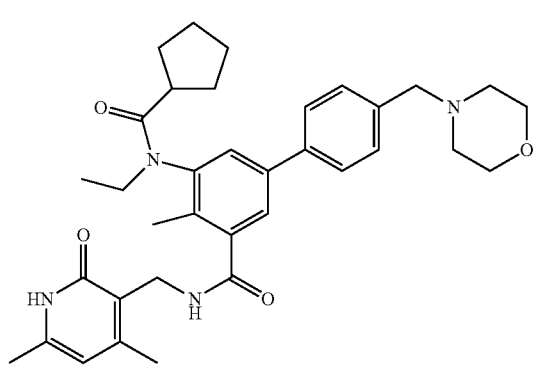 [SMILES: CCN(C(=O)C1CCCC1)c1cc(-c2ccc(CN3CCOCC3)cc2)cc(C(=O)NCc2c(C)cc(C)[nH]c2=O)c1C]

Synthesis of compound 16 was accomplished by using procedures similar to those described in Example 1.

Mass spectrometric data: LC-MS (ESI, m/z): 585.3430 [M+H]$^+$.

Example 17

N-((4,6-dimethyl-2-oxo-1,2-dihydropyridin-3-yl)methyl)-3-(N-ethylcyclopentanecarboxamido)-2-methyl-5-(2-(4-methylpiperazin-1-yl)pyridin-4-yl)benzamide 17

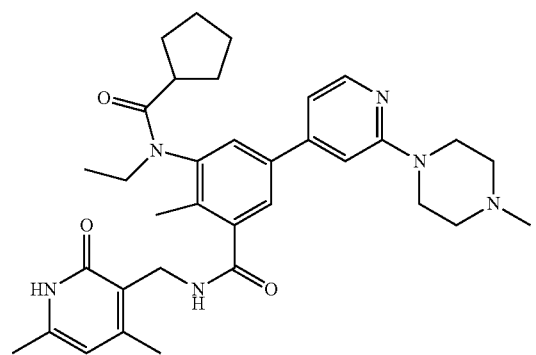

Synthesis of compound 17 was accomplished by using procedures similar to those described in Example 1.

Mass spectrometric data: LC-MS (ESI, m/z): 585.3550 [M+H]$^+$.

Example 18

N-((4,6-dimethyl-2-oxo-1,2-dihydropyridin-3-yl)methyl)-3-(N-ethylcyclopentanecarboxamido)-5-(6-(4-isopropylpiperazin-1-yl)pyridin-3-yl)-2-methylbenzamide 18

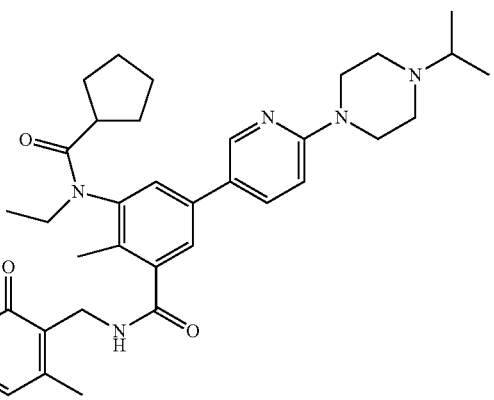

Synthesis of compound 18 was accomplished by using procedures similar to those described in Example 1.

Mass spectrometric data: LC-MS (ESI, m/z): 613.3860 [M+H]$^+$.

Example 19

4'-cyano-N-((4,6-dimethyl-2-oxo-1,2-dihydropyridin-3-yl)methyl)-5-(N-ethylcyclopentanecarboxamido)-3'-fluoro-4-methyl-[1,1'-diphenyl]-3-carboxamide 19

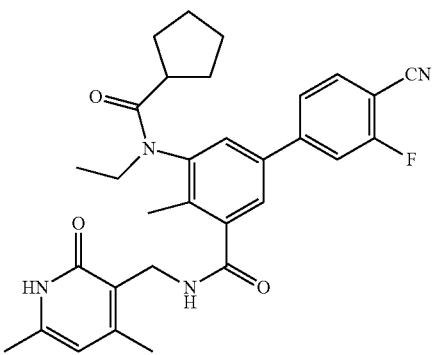 [SMILES: CCN(C(=O)C1CCCC1)c1cc(-c2ccc(C#N)c(F)c2)cc(C(=O)NCc2c(C)cc(C)[nH]c2=O)c1C]

Synthesis of compound 19 was accomplished by using procedures similar to those described in Example 1.

Mass spectrometric data: LC-MS (ESI, m/z): 529.2605 [M+H]$^+$.

Example 20

N-((4,6-dimethyl-2-oxo-1,2-dihydropyridin-3-yl)methyl)-5-(N-ethylcyclopentanecarboxamido)-4-methyl-4'-(morpholin-4-carbonyl)-[1,1'-diphenyl]-3-carboxamide 20

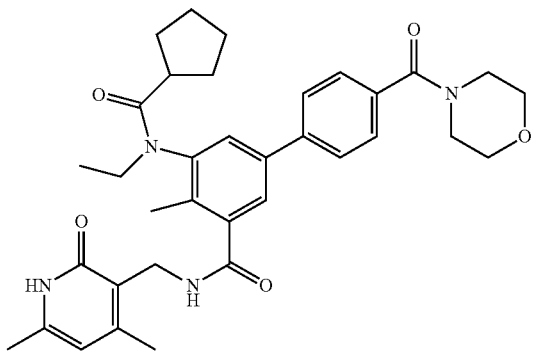 [SMILES: CCN(C(=O)C1CCCC1)c1cc(-c2ccc(C(=O)N3CCOCC3)cc2)cc(C(=O)NCc2c(C)cc(C)[nH]c2=O)c1C]

Synthesis of compound 20 was accomplished by using procedures similar to those described in Example 1.

Mass spectrometric data: LC-MS (ESI, m/z): 599.3240 [M+H]$^+$.

Example 21

N-((4,6-dimethyl-2-oxo-1,2-dihydropyridin-3-yl)methyl)-5-(N-ethylcyclopentanecarboxamido)-4-methyl-4'-morpholinyl-[1,1'-diphenyl]-3-carboxamide 21

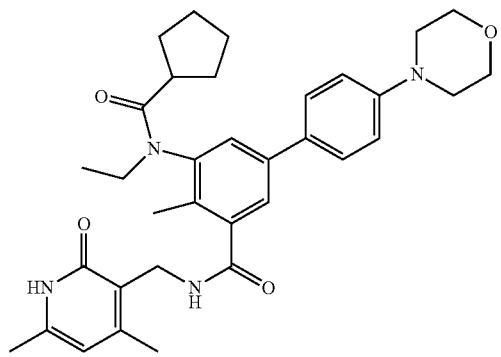 [SMILES: CCN(C(=O)C1CCCC1)c1cc(-c2ccc(N3CCOCC3)cc2)cc(C(=O)NCc2c(C)cc(C)[nH]c2=O)c1C]

Synthesis of compound 21 was accomplished by using procedures similar to those described in Example 1.

Mass spectrometric data: LC-MS (ESI, m/z): 571.3275 [M+H]$^+$.

Example 22

N-((4,6-dimethyl-2-oxo-1,2-dihydropyridin-3-yl)methyl)-5-(N-ethylcyclopentanecarboxamido)-4-methyl-4'-(2-morpholinyl-2-oxoethyl)-[1,1'-diphenyl]-3-carboxamide 22

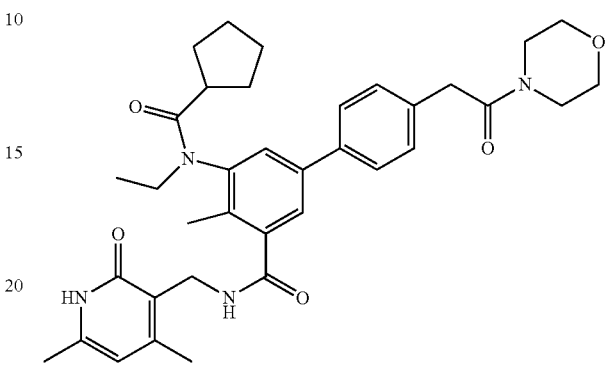

Synthesis of compound 22 was accomplished by using procedures similar to those described in Example 1.

Mass spectrometric data: LC-MS (ESI, m/z): 613.3375 [M+H]$^+$.

Example 23

N-((4,6-dimethyl-2-oxo-1,2-dihydropyridin-3-yl)methyl)-5-(N-ethylcyclopentanecarboxamido)-4'-((4-ethylpiperazin-1-yl)methyl)-4-methyl-[1,1'-diphenyl]-3-carboxamide 23

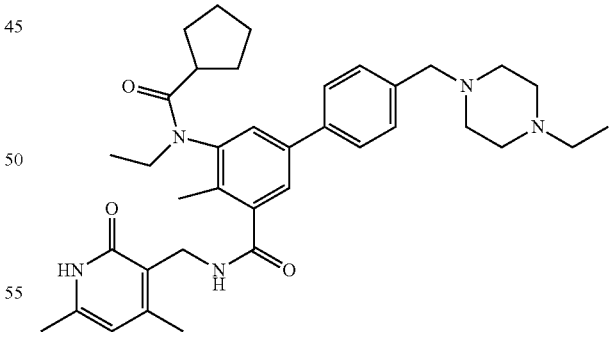

Synthesis of compound 23 was accomplished by using procedures similar to those described in Example 1.

Mass spectrometric data: LC-MS (ESI, m/z): 612.3901 [M+H]$^+$.

Example 24 tert-butyl-4-((3'-(((4,6-dimethyl-2-oxo-1,2-dihydro-pyridin-3-yl)methyl)carbamoyl)-5'-(N-ethylcyclo-pentanecarboxamido)-4'-methyl-[1,1'-diphenyl]-4-yl)methyl)piperazin-1-carboxylate 24

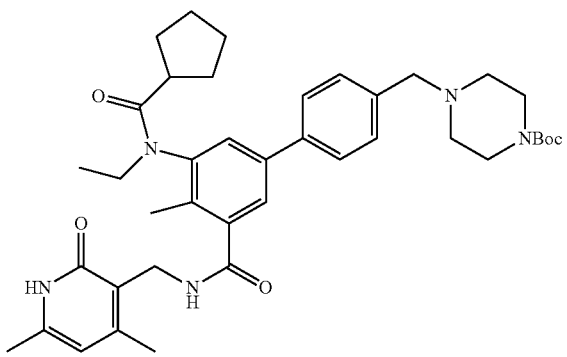 [SMILES: CCN(C(=O)C1CCCC1)c1cc(-c2ccc(CN3CCN(C(=O)OC(C)(C)C)CC3)cc2)cc(C(=O)NCc2c(C)cc(C)[nH]c2=O)c1C]

Synthesis of compound 24 was accomplished by using procedures similar to those described in Example 1.

Mass spectrometric data: LC-MS (ESI, m/z): 684.4105 [M+H]$^+$.

Example 25

N-((4,6-dimethyl-2-oxo-1,2-dihydropyridin-3-yl)methyl)-5-(N-ethylcyclopentanecarboxamido)-4-methyl-4'-((4-piperazin-1-yl)methyl)-4-methyl-[1,1'-diphenyl]-3-carboxamide 25

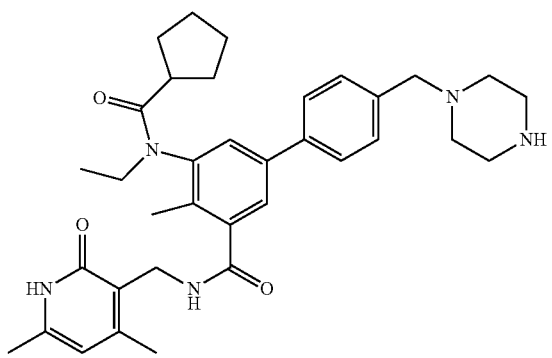 [SMILES: CCN(C(=O)C1CCCC1)c1cc(-c2ccc(CN3CCNCC3)cc2)cc(C(=O)NCc2c(C)cc(C)[nH]c2=O)c1C]

Synthesis of compound 25 was accomplished by using procedures similar to those described in Example 1.

Mass spectrometric data: LC-MS (ESI, m/z): 584.3601 [M+H]$^+$.

Example 26

N-((4,6-dimethyl-2-oxo-1,2-dihydropyridin-3-yl)methyl)-5-(N-ethylcyclopentanecarboxamido)-4-methyl-4'-(prop-2-ylsulfonamide)-[1,1'-diphenyl]-3-carboxamide 26

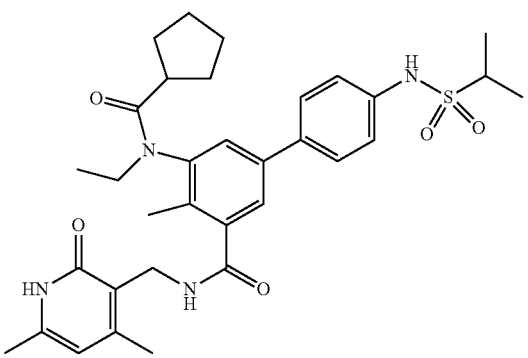 [SMILES: CCN(C(=O)C1CCCC1)c1cc(-c2ccc(NS(=O)(=O)C(C)C)cc2)cc(C(=O)NCc2c(C)cc(C)[nH]c2=O)c1C]

Synthesis of compound 26 was accomplished by using procedures similar to those described in Example 1.

Mass spectrometric data: LC-MS (ESI, m/z): 607.2960 [M+H]$^+$.

Example 27

N-((4,6-dimethyl-2-oxo-1,2-dihydropyridin-3-yl)methyl)-5-(N-ethylcyclopentanecarboxamido)-4'-(4-ethylpiperazin-1-yl)-4-methyl-[1,1'-diphenyl]-3-carboxamide 27

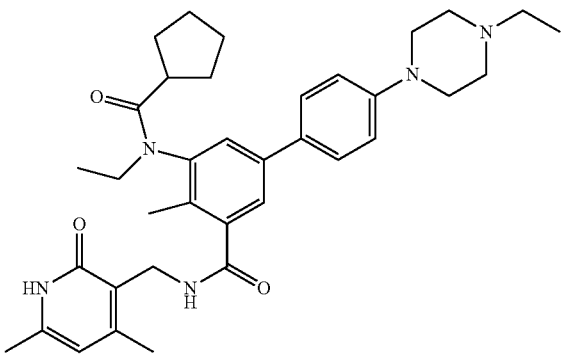 [SMILES: CCN1CCN(c2ccc(-c3cc(C(=O)NCc4c(C)cc(C)[nH]c4=O)c(C)c(N(CC)C(=O)C4CCCC4)c3)cc2)CC1]

Synthesis of compound 27 was accomplished by using procedures similar to those described in Example 1.

Mass spectrometric data: LC-MS (ESI, m/z): 598.3750 [M+H]$^+$.

Example 28

4'-(cyclopropanesulfonamide)-N-((4,6-dimethyl-2-oxo-1,2-dihydropyridin-3-yl)methyl)-5-(N-ethylcyclopentanecarboxamido)-4-methyl-[1,1'-diphenyl]-3-carboxamide 28

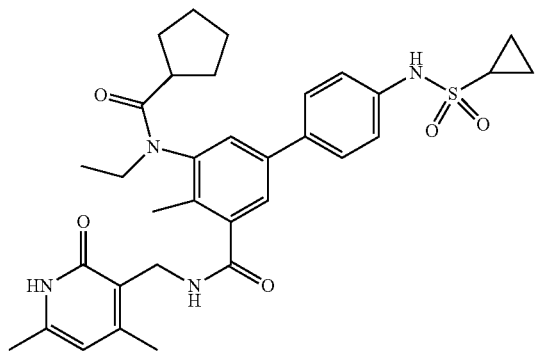 [SMILES: CCN(C(=O)C1CCCC1)c1cc(-c2ccc(NS(=O)(=O)C3CC3)cc2)cc(C(=O)NCc2c(C)cc(C)[nH]c2=O)c1C]

Synthesis of compound 28 was accomplished by using procedures similar to those described in Example 1.

Mass spectrometric data: LC-MS (ESI, m/z): 605.2801 [M+H]$^+$.

Example 29 tertbutyl-4-(5-(3-(((4,6-dimethyl-2-oxo-1,2-dihydropyridin-3-yl)methyl)carbamoyl)-5-(N-ethylcyclopentanecarboxamido)-4-methylphenyl)pyridin-2-yl)piperazin-1-carboxylate 29

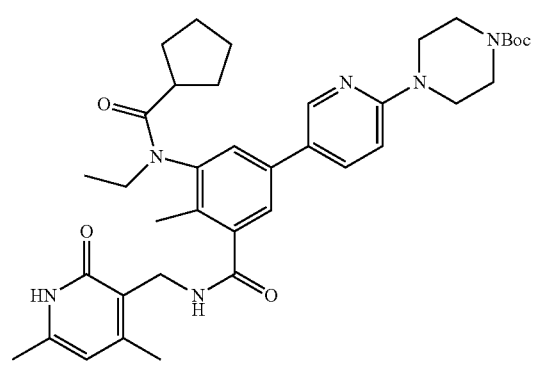 [SMILES: CCN(C(=O)C1CCCC1)c1cc(-c2ccc(N3CCN(C(=O)OC(C)(C)C)CC3)nc2)cc(C(=O)NCc2c(C)cc(C)[nH]c2=O)c1C]

Synthesis of compound 29 was accomplished by using procedures similar to those described in Example 1.

Mass spectrometric data: LC-MS (ESI, m/z): 671.3911 [M+H]$^+$.

Example 30

N-((4,6-dimethyl-2-oxo-1,2-dihydropyridin-3-yl)methyl)-5-(N-ethylcyclopentanecarboxamido)-4-methyl-4'-(3-morpholinopropoxy)-[1,1'-diphenyl]-3-carboxamide 30

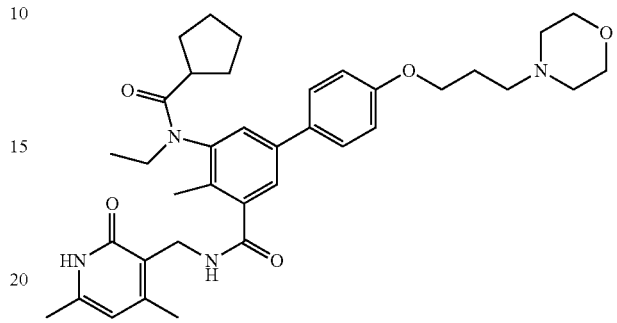

Synthesis of compound 30 was accomplished by using procedures similar to those described in Example 1.

Mass spectrometric data: LC-MS (ESI, m/z): 629.3720 [M+H]$^+$.

Example 31

N-((4,6-dimethyl-2-oxo-1,2-dihydropyridin-3-yl)methyl)-5-(N-ethylcyclopentanecarboxamido)-4-methyl-4'-(piperazin-1-yl)-[1,1'-diphenyl]-3-carboxamide 31

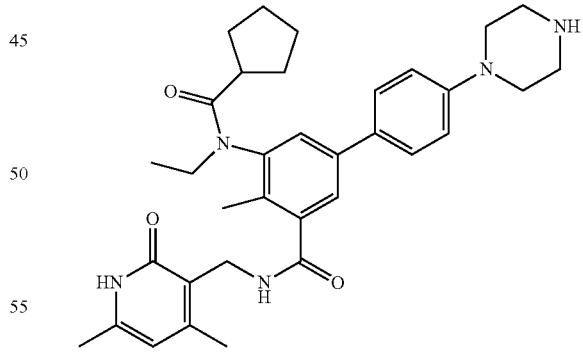

Synthesis of compound 31 was accomplished by using procedures similar to those described in Example 1.

Mass spectrometric data: LC-MS (ESI, m/z): 570.3438 [M+H]$^+$.

Example 32

N-((4,6-dimethyl-2-oxo-1,2-dihydropyridin-3-yl)methyl)-3-(N-ethylcyclopentanecarboxamido)-2-methyl-5-(6-(piperazin-1-yl)pyridin-3-yl)-benzamide 32

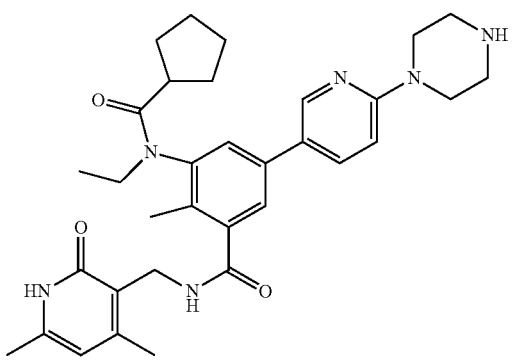 [SMILES: CCN(C(=O)C1CCCC1)c1cc(-c2ccc(N3CCNCC3)nc2)cc(C(=O)NCc2c(C)cc(C)[nH]c2=O)c1C]

Synthesis of compound 32 was accomplished by using procedures similar to those described in Example 1.

Mass spectrometric data: LC-MS (ESI, m/z): 571.3405 [M+H]$^+$.

Example 33

5-cyano-N-((4,6-dimethyl-2-oxo-1,2-dihydropyridin-3-yl)methyl)-3-(N-ethylcyclopentanecarboxamido)-2-methylbenzamide 33

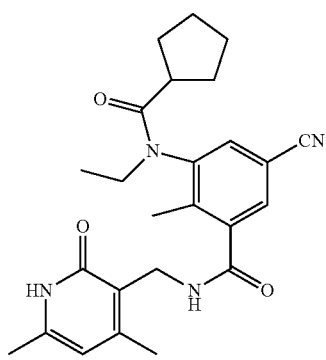 [SMILES: CCN(C(=O)C1CCCC1)c1cc(C#N)cc(C(=O)NCc2c(C)cc(C)[nH]c2=O)c1C]

Synthesis of compound 33 was accomplished by using procedures similar to those described in Example 1.

Mass spectrometric data: LC-MS (ESI, m/z): 435.2388 [M+H]$^+$.

Example 34

$N^1$-((4,6-dimethyl-2-oxo-1,2-dihydropyridin-3-yl)methyl)-5-(N-ethylcyclopentanecarboxamido)-6-methyl-isophthalamide 34

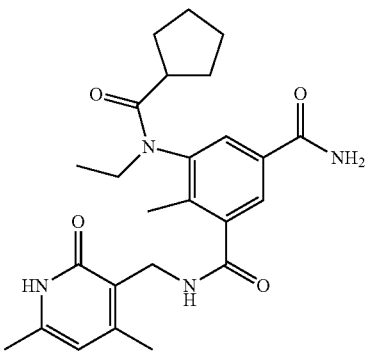 [SMILES: CCN(C(=O)C1CCCC1)c1cc(C(N)=O)cc(C(=O)NCc2c(C)cc(C)[nH]c2=O)c1C]

Synthesis of compound 34 was accomplished by using procedures similar to those described in Example 1.

Mass spectrometric data: LC-MS (ESI, m/z): 453.2511 [M+H]$^+$.

Example 35

(S)—N-((4,6-dimethyl-2-oxo-1,2-dihydropyridin-3-yl)methyl)-5-(N-ethylcyclopentanecarboxamido)-4'-((2-hydroxymethyl)piperazin-1-yl)methyl)-4-methyl-[1,1'-diphenyl]-3-carboxamide 35

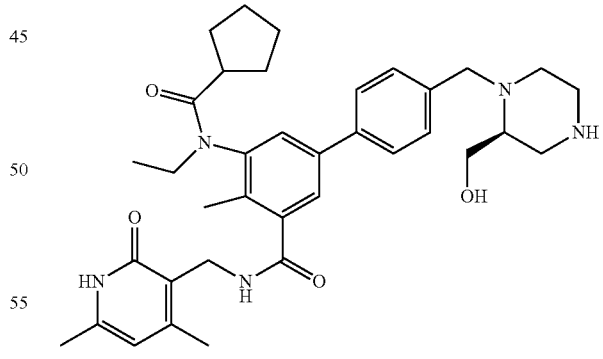

Synthesis of compound 35 was accomplished by using procedures similar to those described in Example 1.

Mass spectrometric data: LC-MS (ESI, m/z): 614.3702 [M+H]$^+$.

Example 36

N-((4,6-dimethyl-2-oxo-1,2-dihydropyridin-3-yl)methyl)-3-(N-ethylcyclopentanecarboxamido)-2-methyl-5-(6-(4-methylpiperazin-1-yl)pyridin-3-yl)benzamide 36

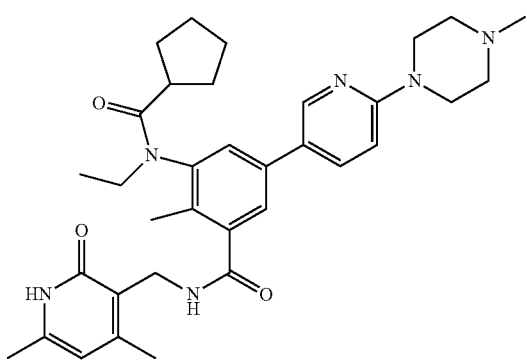

Synthesis of compound 36 was accomplished by using procedures similar to those described in Example 1.

Mass spectrometric data: LC-MS (ESI, m/z): 585.3541 [M+H]$^+$.

Example 37

5-(6-(4-aminopiperidin-1-yl)pyridin-3-yl)-N-((4,6-dimethyl-2-oxo-1,2-dihydropyridin-3-yl)methyl)-3-(N-ethylcyclopentanecarboxamido)-2-methylbenzamide 37

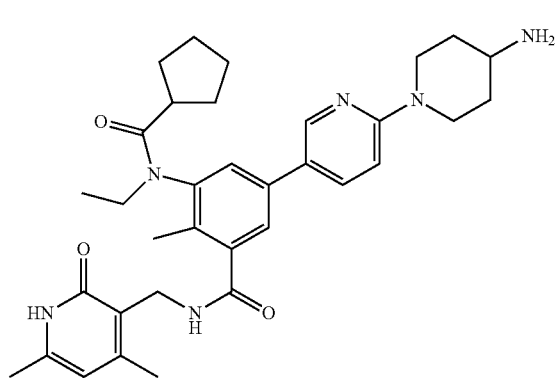 [SMILES: CCN(C(=O)C1CCCC1)c1cc(-c2ccc(N3CCC(N)CC3)nc2)cc(C(=O)NCc2c(C)cc(C)[nH]c2=O)c1C]

Synthesis of compound 37 was accomplished by using procedures similar to those described in Example 1.

Mass spectrometric data: LC-MS (ESI, m/z): 585.3540 [M+H]$^+$.

Example 38

5-(2-(4-(cyclopropylmethyl)piperazin-1-yl)pyridin-4-yl)-N-((4,6-dimethyl-2-oxo-1,2-dihydropyridin-3-yl)methyl)-3-(N-ethylcyclopentanecarboxamido)-2-methylbenzamide 38

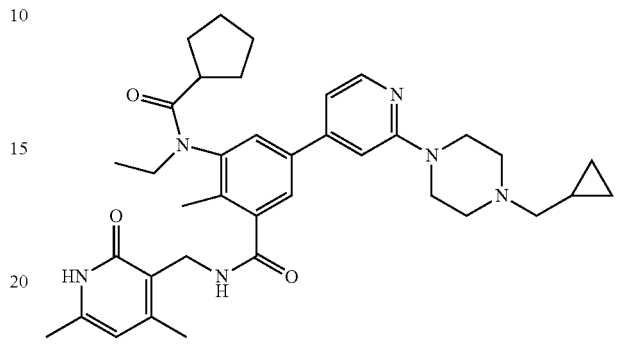

Synthesis of compound 38 was accomplished by using procedures similar to those described in Example 1.

Mass spectrometric data: LC-MS (ESI, m/z): 625.3859 [M+H]$^+$.

Example 39

5-(2-(4-(cyclopropylmethyl)piperazin-1-yl)pyridin-4-yl)-3-(N-ethylcyclopentanecarboxamido)-2-methyl-N-((6-methyl-2-oxo-4-propyl-1,2-dihydropyridin-3-yl)methyl)benzamide 39

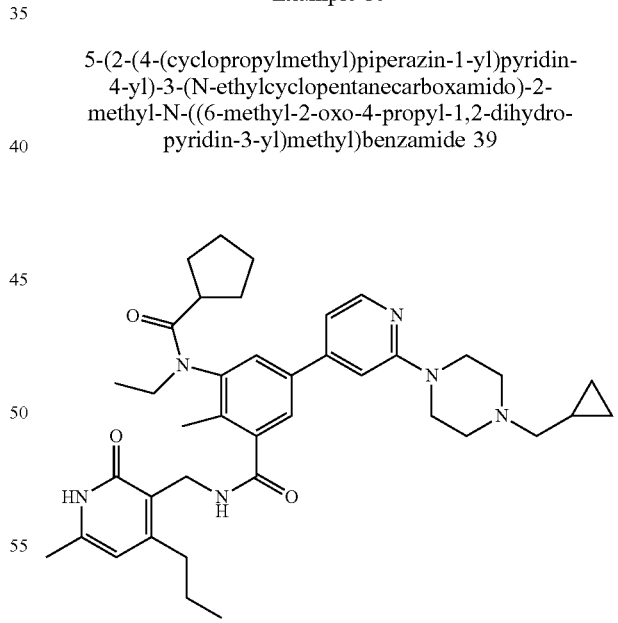

Synthesis of compound 39 was accomplished by using procedures similar to those described in Example 1.

Mass spectrometric data: LC-MS (ESI, m/z): 653.4165 [M+H]$^+$.

Example 40

N-((4,6-dimethyl-2-oxo-1,2-dihydropyridin-3-yl)methyl)-5-(N-ethylcyclopentanecarboxamido)-4-methyl-4'-(2-morpholinoethoxyl)-[1,1'-diphenyl]-3-carboxamide 40

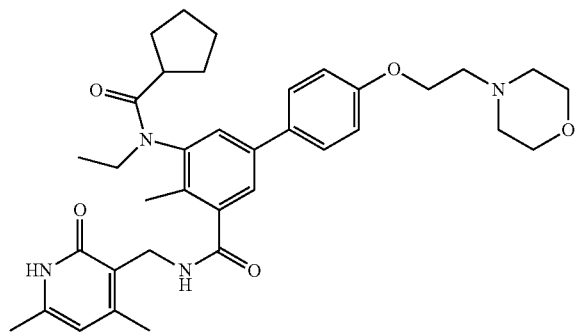 [SMILES: CCN(C(=O)C1CCCC1)c1cc(-c2ccc(OCCN3CCOCC3)cc2)cc(C(=O)NCc2c(C)cc(C)[nH]c2=O)c1C]

Synthesis of compound 40 was accomplished by using procedures similar to those described in Example 1.

Mass spectrometric data: LC-MS (ESI, m/z): 615.3550 [M+H]$^+$.

Example 41

N-((4,6-dimethyl-2-oxo-1,2-dihydropyridin-3-yl)methyl)-5-(N-ethylcyclopentanecarboxamido)-4-methyl-4'-phenoxy-[1,1'-diphenyl]-3-carboxamide 41

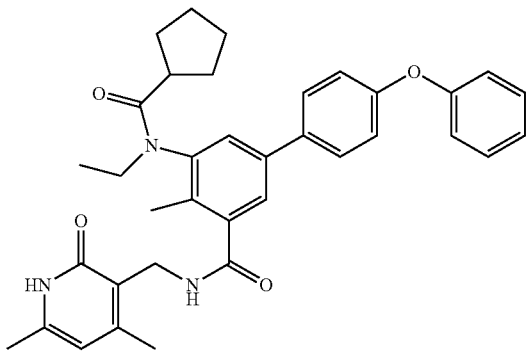 [SMILES: CCN(C(=O)C1CCCC1)c1cc(-c2ccc(Oc3ccccc3)cc2)cc(C(=O)NCc2c(C)cc(C)[nH]c2=O)c1C]

Synthesis of compound 41 was accomplished by using procedures similar to those described in Example 1.

Mass spectrometric data: LC-MS (ESI, m/z): 578.3008 [M+H]$^+$.

Example 42

N-((4,6-dimethyl-2-oxo-1,2-dihydropyridin-3-yl)methyl)-5-(N-ethylcyclopentanecarboxamido)-3'-fluoro-4-methyl-4'-(3-morpholinopropoxy)-[1,1'-diphenyl]-3-carboxamide 42

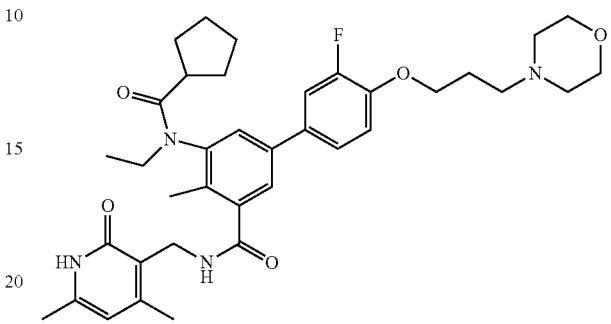

Synthesis of compound 42 was accomplished by using procedures similar to those described in Example 1.

Mass spectrometric data: LC-MS (ESI, m/z): 647.3601 [M+H]$^+$.

Example 43

5-(5-acetylthiophene-2-yl)-N-((4,6-dimethyl-2-oxo-1,2-dihydropyridin-3-yl)methyl)-3-(N-ethylcyclopentanecarboxamido)-2-methylbenzamide 43

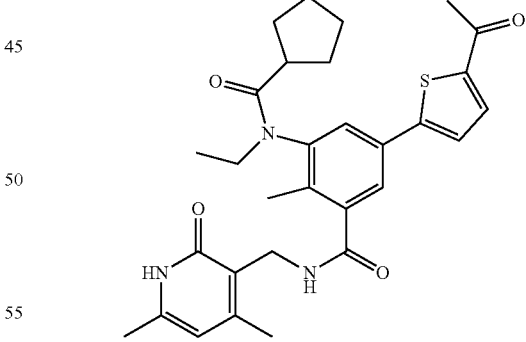

Synthesis of compound 43 was accomplished by using procedures similar to those described in Example 1.

Mass spectrometric data: LC-MS (ESI, m/z): 534.2415 [M+H]$^+$.

Example 44

N-((4,6-dimethyl-2-oxo-1,2-dihydropyridin-3-yl)methyl)-5-(N-ethylcyclopentanecarboxamido)-2'-fluoro-4-methyl-4'-(3-morpholinopropoxy)-[1,1'-diphenyl]-3-carboxamide 44

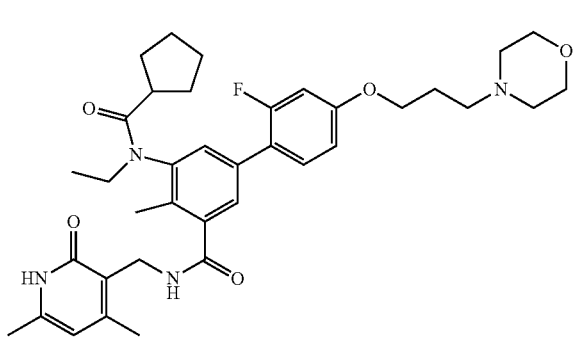 [SMILES: CCN(C(=O)C1CCCC1)c1cc(-c2ccc(OCCCN3CCOCC3)cc2F)cc(C(=O)NCc2c(C)cc(C)[nH]c2=O)c1C]

Synthesis of compound 44 was accomplished by using procedures similar to those described in Example 1.

Mass spectrometric data: LC-MS (ESI, m/z): 647.3602 [M+H]$^+$.

Example 45

N-((4,6-dimethyl-2-oxo-1,2-dihydropyridin-3-yl)methyl)-5-(N-ethylcyclopentanecarboxamido)-2',4-methyl-4'-(3-morpholinopropoxy)-[1,1'-diphenyl]-3-carboxamide 45

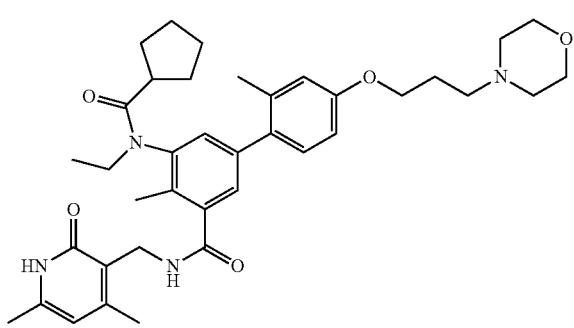 [SMILES: CCN(C(=O)C1CCCC1)c1cc(-c2ccc(OCCCN3CCOCC3)cc2C)cc(C(=O)NCc2c(C)cc(C)[nH]c2=O)c1C]

Synthesis of compound 45 was accomplished by using procedures similar to those described in Example 1.

Mass spectrometric data: LC-MS (ESI, m/z): 643.3855 [M+H]$^+$.

Example 46

N-((4,6-dimethyl-2-oxo-1,2-dihydropyridin-3-yl)methyl)-5-(N-ethylcyclopentanecarboxamido)-3',4-methyl-4'-(3-morpholinopropoxy)-[1,1'-diphenyl]-3-carboxamide 46

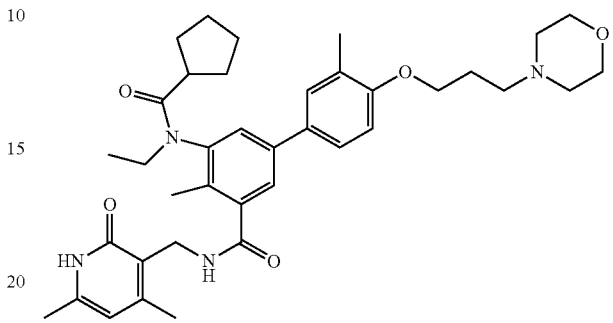

Synthesis of compound 46 was accomplished by using procedures similar to those described in Example 1.

Mass spectrometric data: LC-MS (ESI, m/z): 643.3854 [M+H]$^+$.

Example 47

3'-cyano-N-((4,6-dimethyl-2-oxo-1,2-dihydropyridin-3-yl)methyl)-5-(N-ethylcyclopentanecarboxamido)-4-methyl-4'-(2-morpholinoethoxyl)-[1,1'-diphenyl]-3-carboxamide 47

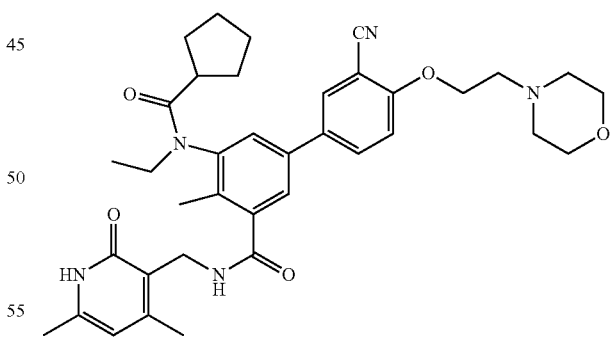

Synthesis of compound 47 was accomplished by using procedures similar to those described in Example 1.

Mass spectrometric data: LC-MS (ESI, m/z): 640.3503 [M+H]$^+$.

Example 48

2'-chloro-N-((4,6-dimethyl-2-oxo-1,2-dihydropyridin-3-yl)methyl)-5-(N-ethylcyclopentanecarboxamido)-4-methyl-4'-(2-morpholinoethoxyl)[1,1'-diphenyl]-3-carboxamide 48

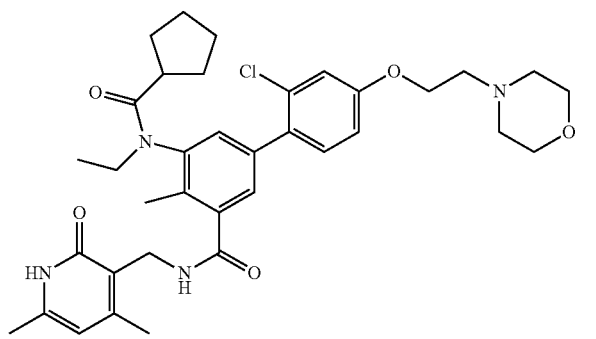 [SMILES: CCN(C(=O)C1CCCC1)c1cc(-c2ccc(OCCN3CCOCC3)cc2F)cc(C(=O)NCc2c(C)cc(C)[nH]c2=O)c1C]

Synthesis of compound 48 was accomplished by using procedures similar to those described in Example 1.

Mass spectrometric data: LC-MS (ESI, m/z): 649.3172 [M+H]$^+$.

Example 49

N-((4,6-dimethyl-2-oxo-1,2-dihydropyridin-3-yl)methyl)-5-(N-ethylcyclopentanecarboxamido)-3'-methoxy-4-methyl-4'-(2-morpholinoethoxyl)-[1,1'-diphenyl]-3-carboxamide 49

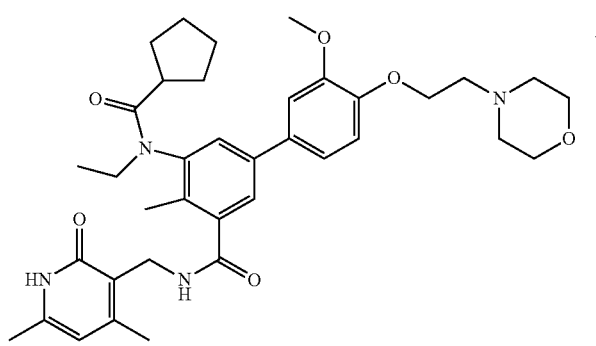

Synthesis of compound 49 was accomplished by using procedures similar to those described in Example 1.

Mass spectrometric data: LC-MS (ESI, m/z): 645.3661 [M+H]$^+$.

Example 50

3-(N-(cyclopropylmethyl)cyclopentanecarboxamido)-N-((4,6-dimethyl-2-oxo-1,2-dihydropyridin-3-yl)methyl)-5-(6-(4-(dimethylamino)piperidin-1-yl)pyridin-3-yl)-2-methylbenzamide 50

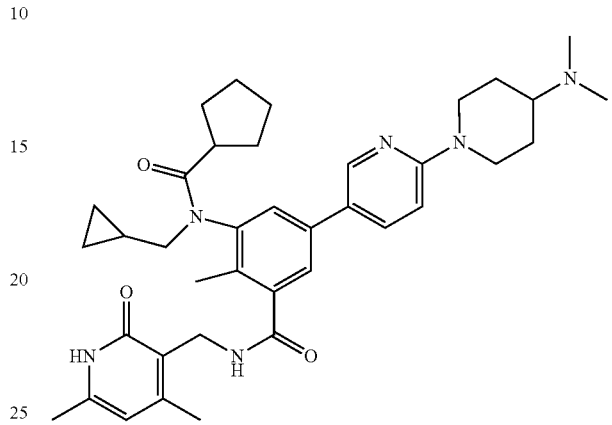

Synthesis of compound 50 was accomplished by using procedures similar to those described in Example 1.

Mass spectrometric data: LC-MS (ESI, m/z): 639.4018 [M+H]$^+$.

Example 51

N-((4,6-dimethyl-2-oxo-1,2-dihydropyridin-3-yl)methyl)-5-(N-ethylcyclopentanecarboxamido)-2'-fluoro-4-methyl-4'-(2-morpholinoethoxyl)-[1,1'-diphenyl]-3-carboxamide 51

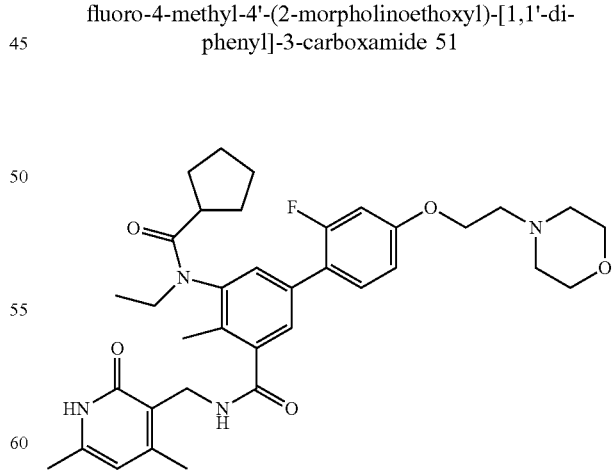

Synthesis of compound 51 was accomplished by using procedures similar to those described in Example 1.

Mass spectrometric data: LC-MS (ESI, m/z): 633.3432 [M+H]$^+$.

Example 52

N-((4,6-dimethyl-2-oxo-1,2-dihydropyridin-3-yl)methyl)-5-(N-ethylcyclopentanecarboxamido)-3'-fluoro-4-methyl-4'-(2-morpholinoethoxyl)-[1,1'-diphenyl]-3-carboxamide 52

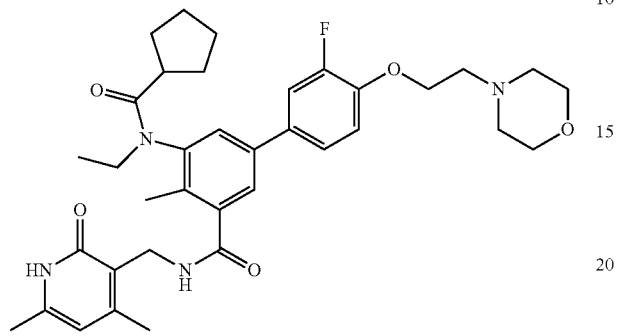

Synthesis of compound 52 was accomplished by using procedures similar to those described in Example 1.

Mass spectrometric data: LC-MS (ESI, m/z): 633.3435 [M+H]$^+$.

Example 53

N-(5-(((4,6-dimethyl-2-oxo-1,2-dihydropyridin-3-yl)methyl)carbamoyl-4-methyl-4'-(morpholinomethyl)-[1,1'-diphenyl]-N-ethyltetrahydro-2H-pyran-4-carboxamide 53

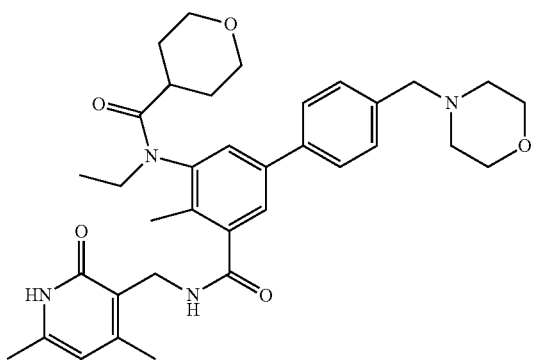 [SMILES: CCN(C(=O)C1CCOCC1)c1cc(-c2ccc(CN3CCOCC3)cc2)cc(C(=O)NCc2c(C)cc(C)[nH]c2=O)c1C]

Synthesis of compound 53 was accomplished by using procedures similar to those described in Example 1.

Mass spectrometric data: LC-MS (ESI, m/z): 601.3388 [M+H]$^+$.

Example 54

N-((4,6-dimethyl-2-oxo-1,2-dihydropyridin-3-yl)methyl)-5-(N-ethyl-3,3-dimethylbutyramido)-4-methyl-4'-(morpholinomethyl)-[1,1'-diphenyl]-3-carboxamide 54

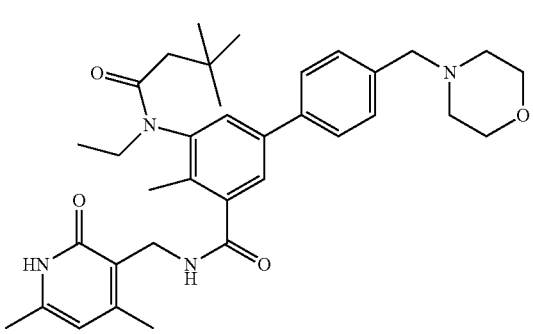 [SMILES: CCN(C(=O)CC(C)(C)C)c1cc(-c2ccc(CN3CCOCC3)cc2)cc(C(=O)NCc2c(C)cc(C)[nH]c2=O)c1C]

Synthesis of compound 54 was accomplished by using procedures similar to those described in Example 1.

Mass spectrometric data: LC-MS (ESI, m/z): 587.3601 [M+H]$^+$.

Example 55

N-(5-(((4,6-dimethyl-2-oxo-1,2-dihydropyridin-3-yl)methyl)carbamoyl-4-methyl-4'-(morpholinomethyl)-[1,1'-diphenyl]-N-ethylfuran-4-carboxamide 55

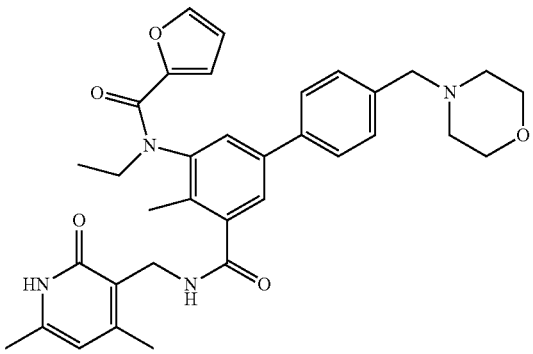 [SMILES: CCN(C(=O)c1ccco1)c1cc(-c2ccc(CN3CCOCC3)cc2)cc(C(=O)NCc2c(C)cc(C)[nH]c2=O)c1C]

Synthesis of compound 55 was accomplished by using procedures similar to those described in Example 1.

Mass spectrometric data: LC-MS (ESI, m/z): 583.2909 [M+H]$^+$.

Example 56

N-((4,6-dimethyl-2-oxo-1,2-dihydropyridin-3-yl)methyl)-5-(N-ethylcyclohexylcarboxamido)-4-methyl-4'-(morpholinomethyl)-[1,1'-diphenyl]-3-carboxamide 56

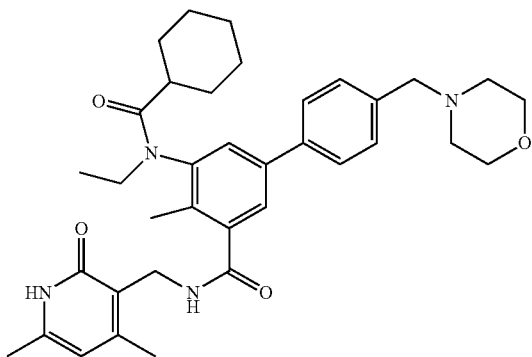 [SMILES: CCN(C(=O)C1CCCCC1)c1cc(-c2ccc(CN3CCOCC3)cc2)cc(C(=O)NCc2c(C)cc(C)[nH]c2=O)c1C]

Synthesis of compound 56 was accomplished by using procedures similar to those described in Example 1.

Mass spectrometric data: LC-MS (ESI, m/z): 599.3599 [M+H]$^+$.

Example 57

N-((4,6-dimethyl-2-oxo-1,2-dihydropyridin-3-yl)methyl)-5-(N-ethyl-4-methylbenzamido)-4-methyl-4'-(morpholinomethyl)-[1,1'-diphenyl]-3-carboxamide 57

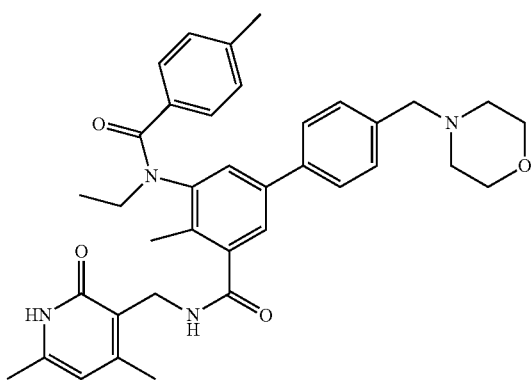 [SMILES: CCN(C(=O)c1ccc(C)cc1)c1cc(-c2ccc(CN3CCOCC3)cc2)cc(C(=O)NCc2c(C)cc(C)[nH]c2=O)c1C]

Synthesis of compound 57 was accomplished by using procedures similar to those described in Example 1.

Mass spectrometric data: LC-MS (ESI, m/z): 607.3271 [M+H]$^+$.

Example 58

N-((4,6-dimethyl-2-oxo-1,2-dihydropyridin-3-yl)methyl)-5-(N-ethyl-2,2-dimethylbutyramido)-4-methyl-4'-(morpholinomethyl)-[1,1'-diphenyl]-3-carboxamide 58

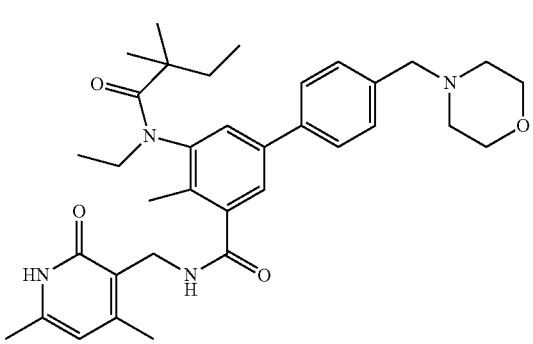 [SMILES: CCN(C(=O)C(C)(C)CC)c1cc(-c2ccc(CN3CCOCC3)cc2)cc(C(=O)NCc2c(C)cc(C)[nH]c2=O)c1C]

Synthesis of compound 58 was accomplished by using procedures similar to those described in Example 1.

Mass spectrometric data: LC-MS (ESI, m/z): 587.3597 [M+H]$^+$.

Example 59

5-(N,2-diethylbutyramido)-N-((4,6-dimethyl-2-oxo-1,2-dihydropyridin-3-yl)methyl)-4-methyl-4'-(morpholinomethyl)-[1,1'-diphenyl]-3-carboxamide 59

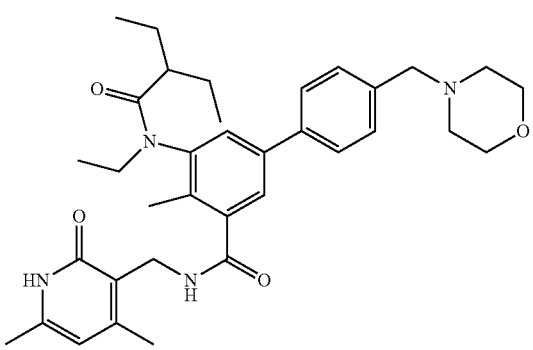 [SMILES: CCC(CC)C(=O)N(CC)c1cc(-c2ccc(CN3CCOCC3)cc2)cc(C(=O)NCc2c(C)cc(C)[nH]c2=O)c1C]

Synthesis of compound 59 was accomplished by using procedures similar to those described in Example 1.

Mass spectrometric data: LC-MS (ESI, m/z): 587.3600 [M+H]$^+$.

Example 60

(1R,4R)—N-(5-(((4,6-dimethyl-2-oxo-1,2-dihydro-pyridin-3-yl)methyl)carbamoyl-4-methyl-4'-(morpholinomethyl)-[1,1'-diphenyl]-3-yl)-N-ethylbicyclo[2.2.1]hept-5-en-2-carboxamide 60

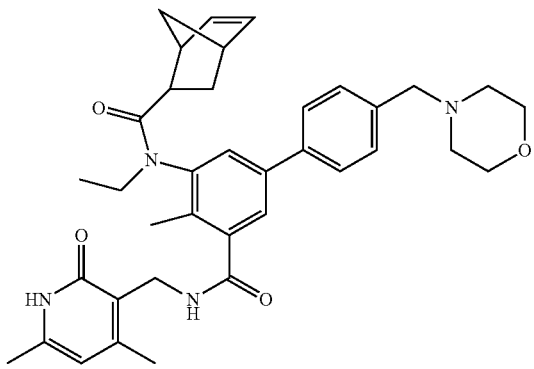 [SMILES: CCN(C(=O)C1CC2C=CC1C2)c1cc(-c2ccc(CN3CCOCC3)cc2)cc(C(=O)NCc2c(C)cc(C)[nH]c2=O)c1C]

Synthesis of compound 60 was accomplished by using procedures similar to those described in Example 1.

Mass spectrometric data: LC-MS (ESI, m/z): 609.3429 [M+H]$^+$.

Example 61

N-((4,6-dimethyl-2-oxo-1,2-dihydropyridin-3-yl)methyl)-5-(N-ethylcyclobutanecarboxamido)-4-methyl-4'-(morpholinomethyl)-[1,1'-diphenyl]-3-carboxamide 61

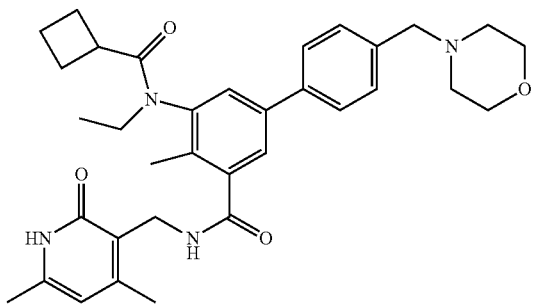 [SMILES: CCN(C(=O)C1CCC1)c1cc(-c2ccc(CN3CCOCC3)cc2)cc(C(=O)NCc2c(C)cc(C)[nH]c2=O)c1C]

Synthesis of compound 61 was accomplished by using procedures similar to those described in Example 1.

Mass spectrometric data: LC-MS (ESI, m/z): 571.3295 [M+H]$^+$.

Example 62

N-((4,6-dimethyl-2-oxo-1,2-dihydropyridin-3-yl)methyl)-5-(N-ethylisobutyramido)-4-methyl-4'-(morpholinomethyl)-[1,1'-diphenyl]-3-carboxamide 62

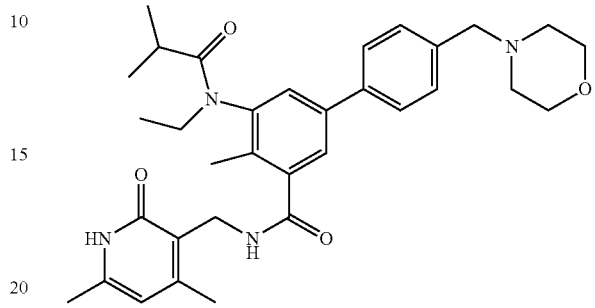

Synthesis of compound 62 was accomplished by using procedures similar to those described in Example 1.

Mass spectrometric data: LC-MS (ESI, m/z): 559.3291 [M+H]$^+$.

Example 63

N-((4,6-dimethyl-2-oxo-1,2-dihydropyridin-3-yl)methyl)-5-(N-ethylcyclopentanecarboxamido)-2',4-dimethyl-4'-(2-morpholinoethoxy)-[1,1'-diphenyl]-3-carboxamide 63

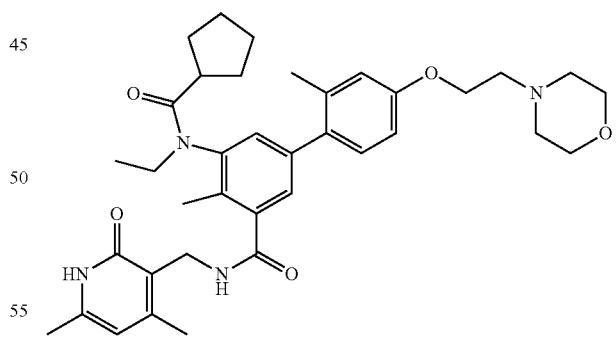

Synthesis of compound 63 was accomplished by using procedures similar to those described in Example 1.

Mass spectrometric data: LC-MS (ESI, m/z): 629.3700 [M+H]$^+$.

Example 64

N-((4,6-dimethyl-2-oxo-1,2-dihydropyridin-3-yl)methyl)-5-(N-ethylcyclopropanecarboxamido)-2',4-dimethyl-4'-(3-morpholinopropoxy)-[1,1'-diphenyl]-3-carboxamide 64

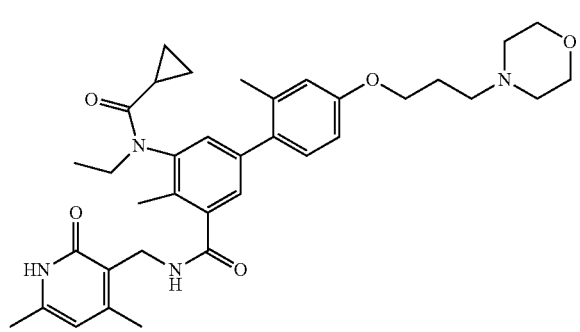 [SMILES: CCN(C(=O)C1CC1)c1cc(-c2ccc(OCCCN3CCOCC3)cc2C)cc(C(=O)NCc2c(C)cc(C)[nH]c2=O)c1C]

Synthesis of compound 64 was accomplished by using procedures similar to those described in Example 1.

Mass spectrometric data: LC-MS (ESI, m/z): 615.3441 [M+H]$^+$.

Example 65

N-((4,6-dimethyl-2-oxo-1,2-dihydropyridin-3-yl)methyl)-5-(N-ethylcyclopropanecarboxamido)-3'-fluoro-4-methyl-4'-(3-morpholinopropoxy)-[1,1'-diphenyl]-3-carboxamide 65

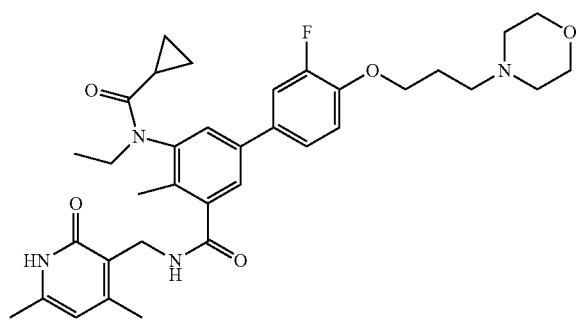 [SMILES: CCN(C(=O)C1CC1)c1cc(-c2ccc(OCCCN3CCOCC3)c(F)c2)cc(C(=O)NCc2c(C)cc(C)[nH]c2=O)c1C]

Synthesis of compound 65 was accomplished by using procedures similar to those described in Example 1.

Mass spectrometric data: LC-MS (ESI, m/z): 619.3301 [M+H]+

Example 66

3-(cyclopropanecarboxamido)-N-((4,6-dimethyl-2-oxo-1,2-dihydropyridin-3-yl)methyl)-5-(6-(4-(dimethylamino)piperidin-1-yl)pyridin-3-yl)-2-methylbenzamide 66

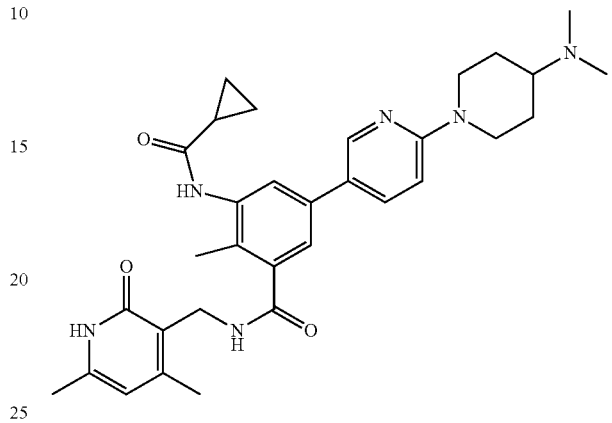

Synthesis of compound 66 was accomplished by using procedures similar to those described in Example 1.

Mass spectrometric data: LC-MS (ESI, m/z): 557.3236 [M+H]$^+$.

Example 67

N-((4,6-dimethyl-2-oxo-1,2-dihydropyridin-3-yl)methyl)-5-(6-(2-(dimethylamino)ethylamino)pyridin-3-yl)-3-(N-ethylcyclopropanecarboxamido)-2-methylbenzamide 67

Synthesis of compound 67 was accomplished by using procedures similar to those described in Example 1.

Mass spectrometric data: LC-MS (ESI, m/z): 545.3245 [M+H]$^+$.

Example 68

N-((4,6-dimethyl-2-oxo-1,2-dihydropyridin-3-yl)methyl)-3-(N-ethylcyclopropanecarboxamido)-2-methyl-5-(6-(4-(pyrrol-1-yl)piperidin-1-yl)pyridin-3-yl)benzamide 68

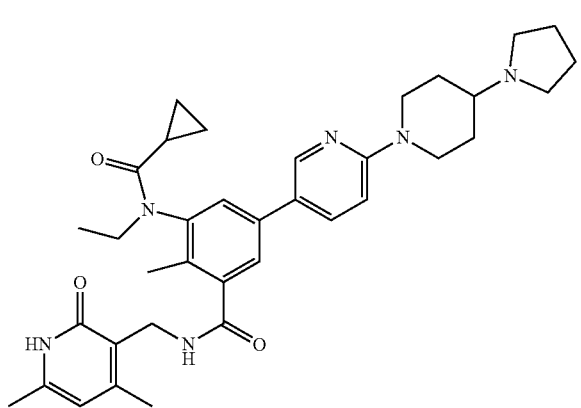 [SMILES: CCN(C(=O)C1CC1)c1cc(-c2ccc(N3CCC(N4CCCC4)CC3)nc2)cc(C(=O)NCc2c(C)cc(C)[nH]c2=O)c1C]

Synthesis of compound 68 was accomplished by using procedures similar to those described in Example 1.

Mass spectrometric data: LC-MS (ESI, m/z): 611.3712 [M+H]$^+$.

Example 69

5-(6-(4-(cyclopropylmethyl)piperazin-1-yl)-2-methylpyridin-3-yl)-N-((4,6-dimethyl-2-oxo-1,2-dihydropyridin-3-yl)methyl)-3-(N-ethylcyclopropanecarboxamido)-2-methylbenzamide 69

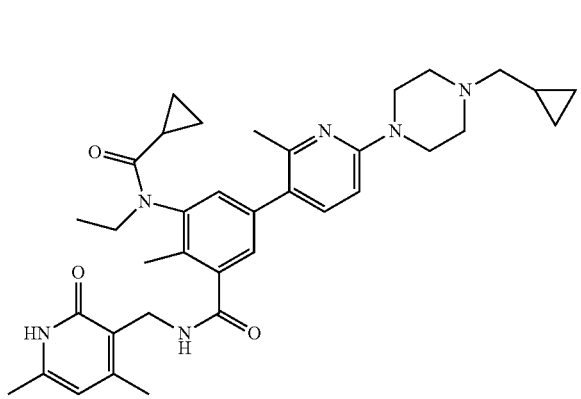 [SMILES: CCN(C(=O)C1CC1)c1cc(-c2ccc(N3CCN(CC4CC4)CC3)nc2C)cc(C(=O)NCc2c(C)cc(C)[nH]c2=O)c1C]

Synthesis of compound 69 was accomplished by using procedures similar to those described in Example 1.

Mass spectrometric data: LC-MS (ESI, m/z): 611.3709 [M+H]$^+$.

Example 70

5-(6-(4-(cyclopropylmethyl)piperazin-1-yl)-5-methylpyridin-3-yl)-N-((4,6-dimethyl-2-oxo-1,2-dihydropyridin-3-yl)methyl)-3-(N-ethylcyclopropanecarboxamido)-2-methylbenzamide 70

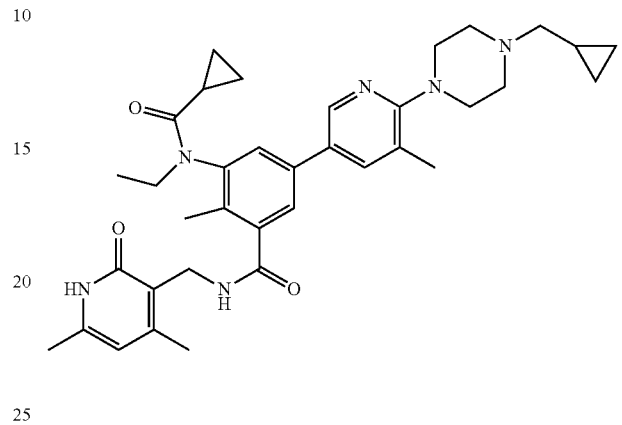

Synthesis of compound 70 was accomplished by using procedures similar to those described in Example 1.

Mass spectrometric data: LC-MS (ESI, m/z): 611.3711 [M+H]$^+$.

Example 71

5-(6-(4-(cyclopropylmethyl)piperazin-1-yl)-4-methylpyridin-3-yl)-N-((4,6-dimethyl-2-oxo-1,2-dihydropyridin-3-yl)methyl)-3-(N-ethylcyclopropanecarboxamido)-2-methylbenzamide 71

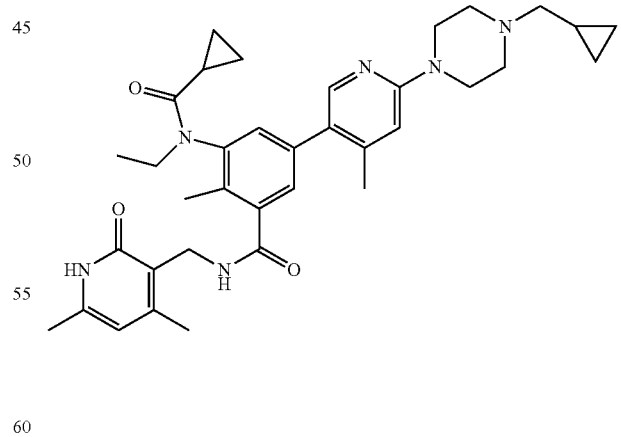

Synthesis of compound 71 was accomplished by using procedures similar to those described in Example 1.

Mass spectrometric data: LC-MS (ESI, m/z): 611.3710 [M+H]$^+$.

Example 72

N-((4,6-dimethyl-2-oxo-1,2-dihydropyridin-3-yl)methyl)-5-(N-ethylcyclopropanecarboxamido)-3',4-dimethyl-4'-(3-morpholinopropoxy)-[1,1'-diphenyl]-3-carboxamide 72

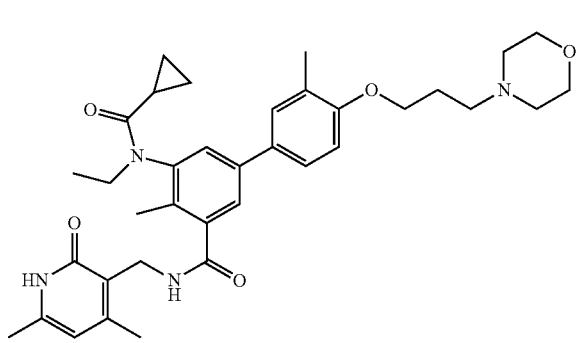 [SMILES: CCN(C(=O)C1CC1)c1cc(-c2ccc(OCCCN3CCOCC3)c(C)c2)cc(C(=O)NCc2c(C)cc(C)[nH]c2=O)c1C]

Synthesis of compound 72 was accomplished by using procedures similar to those described in Example 1.

Mass spectrometric data: LC-MS (ESI, m/z): 615.3440 [M+H]$^+$.

Example 73

N-((4,6-dimethyl-2-oxo-1,2-dihydropyridin-3-yl)methyl)-5-(N-ethylcyclopropanecarboxamido)-2'-chloro-4-methyl-4'-(2-morpholinoethoxyl)-[1,1'-diphenyl]-3-carboxamide 73

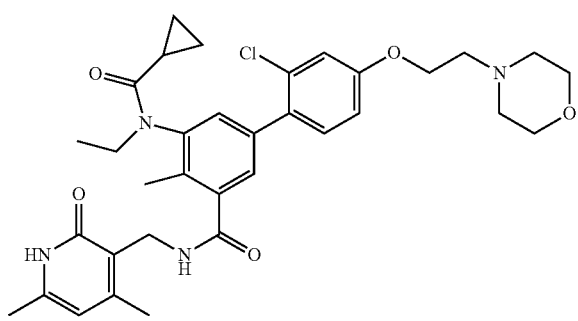 [SMILES: CCN(C(=O)C1CC1)c1cc(-c2ccc(OCCN3CCOCC3)cc2Cl)cc(C(=O)NCc2c(C)cc(C)[nH]c2=O)c1C]

Synthesis of compound 73 was accomplished by using procedures similar to those described in Example 1.

Mass spectrometric data: LC-MS (ESI, m/z): 621.2806 [M+H]+.

Example 74

N-((4,6-dimethyl-2-oxo-1,2-dihydropyridin-3-yl)methyl)-5-(N-ethylcyclopropanecarboxamido)-3'-fluoro-4-methyl-4'-(2-morpholinoethoxyl)-[1,1'-diphenyl]-3-carboxamide 74

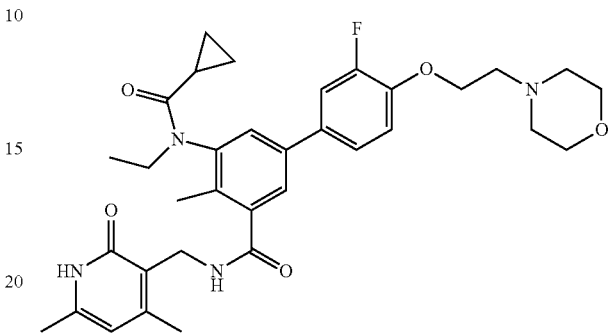

Synthesis of compound 74 was accomplished by using procedures similar to those described in Example 1.

Mass spectrometric data: LC-MS (ESI, m/z): 605.3050 [M+H]$^+$.

Example 75

N-((4,6-dimethyl-2-oxo-1,2-dihydropyridin-3-yl)methyl)-5-(N-ethylcyclopropanecarboxamido)-2',4-dimethyl-4'-(2-morpholinoethoxyl)-[1,1'-diphenyl]-3-carboxamide 75

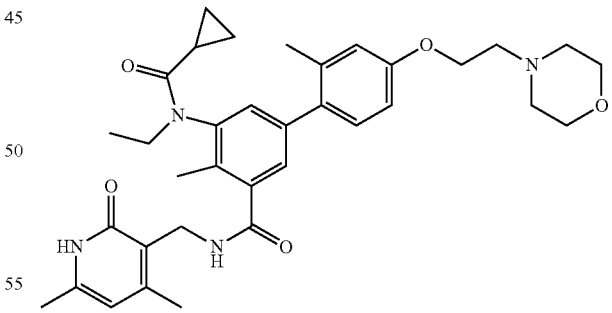

Synthesis of compound 75 was accomplished by using procedures similar to those described in Example 1.

Mass spectrometric data: LC-MS (ESI, m/z): 601.3333 [M+H]$^+$.

Example 76

5-(6-(4-(cyclopropylpiperazin-1-yl)pyridin-3-yl)-N-((4,6-dimethyl-2-oxo-1,2-dihydropyridin-3-yl)methyl)-3-(N-ethylcyclopropanecarboxamido)-2-methylbenzamide 76

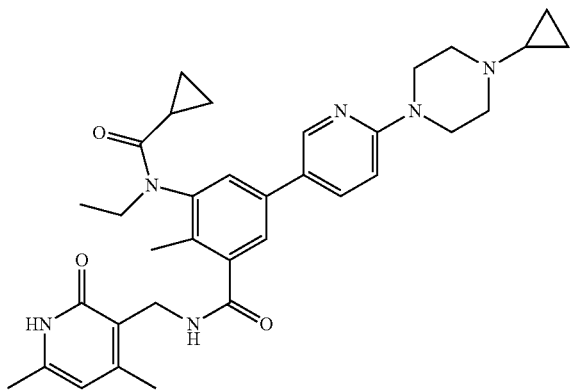 [SMILES: CCN(C(=O)C1CC1)c1cc(-c2ccc(N3CCN(C4CC4)CC3)nc2)cc(C(=O)NCc2c(C)cc(C)[nH]c2=O)c1C]

Synthesis of compound 76 was accomplished by using procedures similar to those described in Example 1.

Mass spectrometric data: LC-MS (ESI, m/z): 583.3323 [M+H]$^+$.

Example 77

N-((4,6-dimethyl-2-oxo-1,2-dihydropyridin-3-yl)methyl)-3-(N-ethylcyclopropanecarboxamido)-2-methyl-5-(6-(4-methylhomopiperazin-1-yl)pyridin-3-yl)benzamide 77

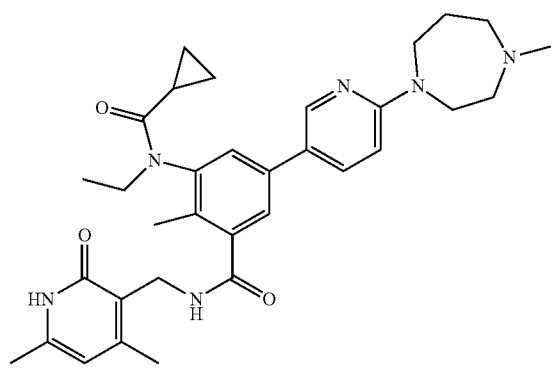

Synthesis of compound 77 was accomplished by using procedures similar to those described in Example 1.

Mass spectrometric data: LC-MS (ESI, m/z): 571.3347 [M+H]$^+$.

Example 78

5-(6-(4-acetylpiperazin-1-yl)pyridin-3-yl)-N-((4,6-dimethyl-2-oxo-1,2-dihydropyridin-3-yl)methyl)-3-(N-ethylcyclopropanecarboxamido)-2-methylbenzamide 78

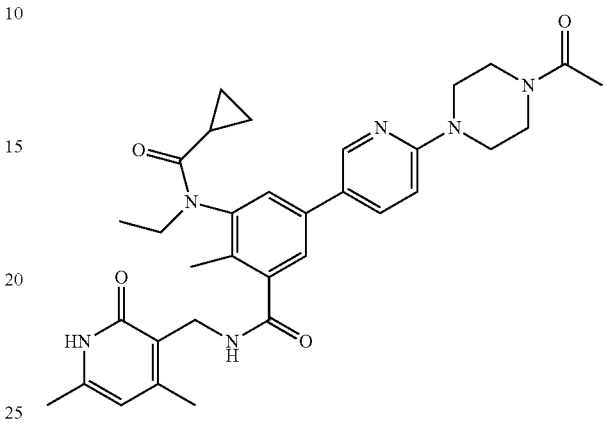

Synthesis of compound 78 was accomplished by using procedures similar to those described in Example 1.

Mass spectrometric data: LC-MS (ESI, m/z): 585.3123 [M+H]$^+$.

Example 79

N-((4,6-dimethyl-2-oxo-1,2-dihydropyridin-3-yl)methyl)-3-(N-ethylcyclopropanecarboxamido)-2-methyl-5-(3-morpholinylpropylamino)benzamide 79

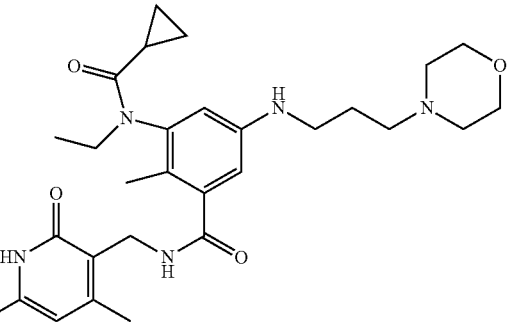

Synthesis of compound 79 was accomplished by using procedures similar to those described in Example 1.

Mass spectrometric data: LC-MS (ESI, m/z): 524.3173 [M+H]$^+$.

Example 80

N-((4,6-dimethyl-2-oxo-1,2-dihydropyridin-3-yl)methyl)-5-((2-(dimethylamino)ethyl)(methyl)amino)-3-(N-ethylcyclopropanecarboxamido)-2-methylbenzamide 80

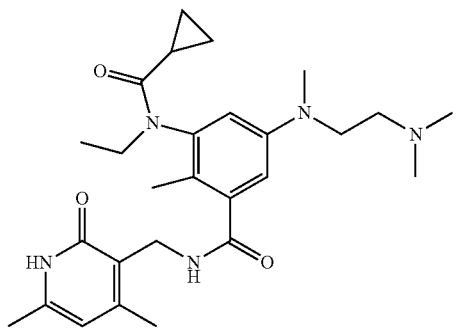

Synthesis of compound 80 was accomplished by using procedures similar to those described in Example 1.

Mass spectrometric data: LC-MS (ESI, m/z): 482.3061 [M+H]+.

Example 81

3'-chloro-N-((4,6-dimethyl-2-oxo-1,2-dihydropyridin-3-yl)methyl)-5-(N-ethylcyclopentanecarboxamido)-4-methyl-4'-(2-morpholinoethoxyl)-[1,1'-biphenyl]-3-carboxamide

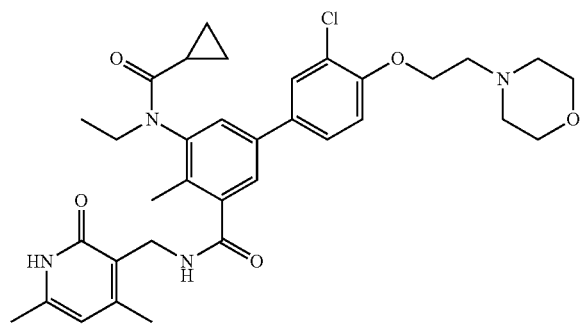 [SMILES: CCN(C(=O)C1CC1)c1cc(-c2ccc(OCCN3CCOCC3)c(Cl)c2)cc(C(=O)NCc2c(C)cc(C)[nH]c2=O)c1C]

Synthesis of compound 81 was accomplished by using procedures similar to those described in Example 1.

Mass spectrometric data: LC-MS (ESI, m/z): 621.2765 [M+H]+.

Example 82

N-((4,6-dimethyl-2-oxo-1,2-dihydropyridin-3-yl)methyl)-5-(N-ethylcyclopentanecarboxamido)-3',4-dimethyl-4'-(2-morpholinoethyl)-[1,1'-biphenyl]-3-carboxamide

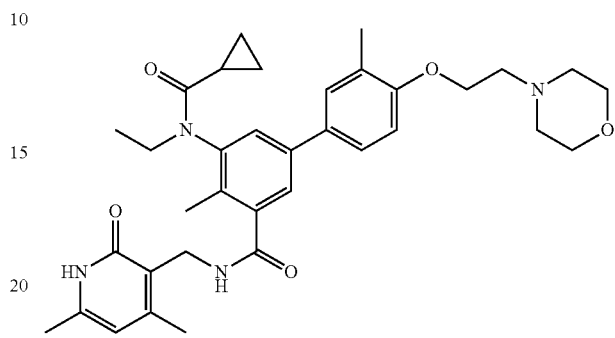

Synthesis of compound 82 was accomplished by using procedures similar to those described in Example 1.

Mass spectrometric data: LC-MS (ESI, m/z): 601.3312 [M+H]+.

Example 83

N-((4,6-dimethyl-2-oxo-1,2-dihydropyridin-3-yl)methyl)-5-(N-ethylcyclopentanecarboxamido)-3'-methoxy-4-methyl-4'-(2-morpholinoethoxyl)-[1,1'-biphenyl]-3-carboxamide

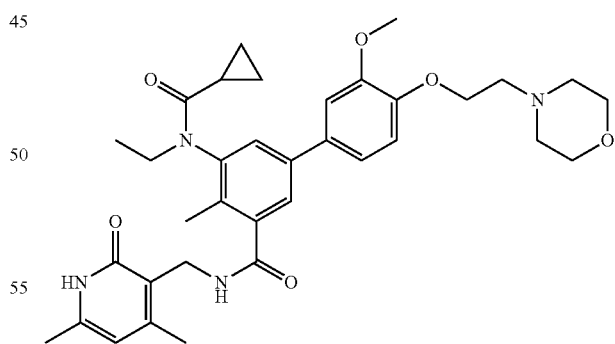

Synthesis of compound 83 was accomplished by using procedures similar to those described in Example 1.

Mass spectrometric data: LC-MS (ESI, m/z): 617.3261 [M+H]+.

Example 84

N-((4,6-dimethyl-2-oxo-1,2-dihydropyridin-3-yl)methyl)-3-(N-ethylcyclopropanecarboxamido)-2-methyl-5-(2-methylpyridin-3-yl)benzamide

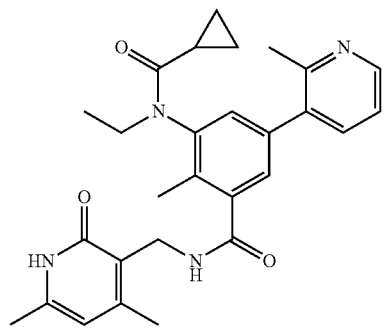 [SMILES: CCN(C(=O)C1CC1)c1cc(-c2cccnc2C)cc(C(=O)NCc2c(C)cc(C)[nH]c2=O)c1C]

Synthesis of compound 84 was accomplished by using procedures similar to those described in Example 1.

Mass spectrometric data: LC-MS (ESI, m/z): 473.2474 [M+H]+.

Example 85

N-((4,6-dimethyl-2-oxo-1,2-dihydropyridin-3-yl)methyl)-3-(N-ethylcyclopentanecarboxamido)-2-methyl-5-(2-methyl-6-morpholinopyridin-3-yl)benzamide

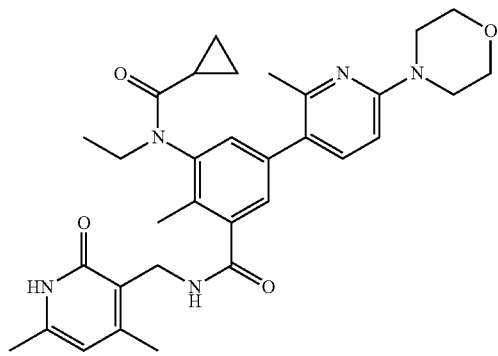 [SMILES: CCN(C(=O)C1CC1)c1cc(-c2ccc(N3CCOCC3)nc2C)cc(C(=O)NCc2c(C)cc(C)[nH]c2=O)c1C]

Synthesis of compound 85 was accomplished by using procedures similar to those described in Example 1.

Mass spectrometric data: LC-MS (ESI, m/z): 473.2474 [M+H]+.

Example 86 tert-butyl(5-(3-(((4,6-dimethyl-2-oxo-1,2-dihydropyridin-3-yl)methyl)carbamoyl)-5-(N-ethylcyclopropanecarboxamido)-4-methylphenyl)-6-methylpyridin-2-yl)piperazin-1-carboxamide

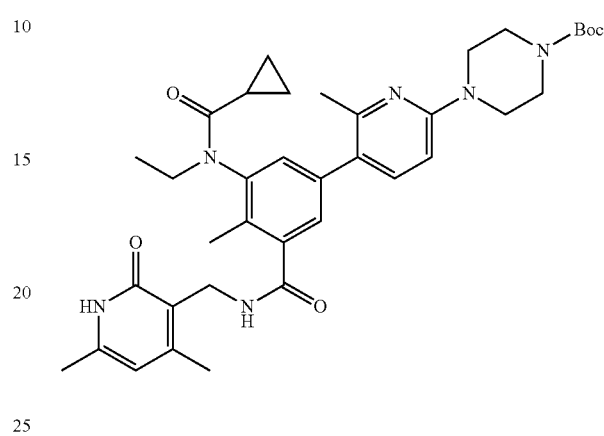

Synthesis of compound 86 was accomplished by using procedures similar to those described in Example 1.

Mass spectrometric data: LC-MS (ESI, m/z): 657.3686 [M+H]+.

Example 87

N-((4,6-dimethyl-2-oxo-1,2-dihydropyridin-3-yl)methyl)-3-(N-ethylcyclopentanecarboxamido)-2-methyl-5-(2-methyl-6-(piperazin-1-yl)pyridin-3-yl)benzamide

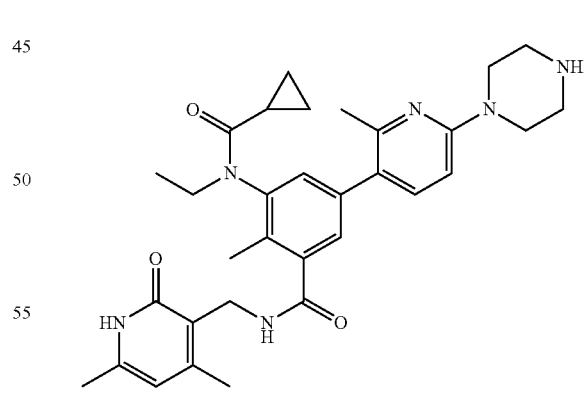

Synthesis of compound 87 was accomplished by using procedures similar to those described in Example 1.

Mass spectrometric data: LC-MS (ESI, m/z): 557.3162 [M+H]+.

Example 88

(6-amino-2-methylpyridin-3-yl)-N-((4,6-dimethyl-2-oxo-1,2-dihydropyridin-3-yl)methyl)-3-(N-ethylcyclopentanecarboxamido)-2-methylbenzamide

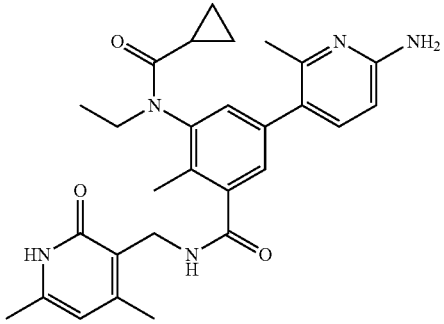

Synthesis of compound 88 was accomplished by using procedures similar to those described in Example 1.

Mass spectrometric data: LC-MS (ESI, m/z): 488.2583 [M+H]+.

Example 89

N-((4,6-dimethyl-2-oxo-1,2-dihydropyridin-3-yl)methyl)-5-(6-(dimethylamino)-2-methylpyridin-3-yl)-3-(N-ethylcyclopropanecarboxamido)-2-methylbenzamide

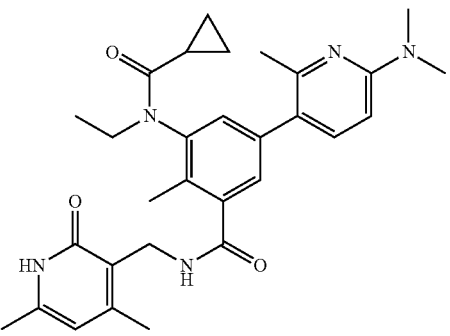

Synthesis of compound 89 was accomplished by using procedures similar to those described in Example 1.

Mass spectrometric data: LC-MS (ESI, m/z): 516.2896 [M+H]+.

Example 90

N-((4,6-dimethyl-2-oxo-1,2-dihydropyridin-3-yl)methyl)-3-(N-ethylcyclopropanecarboxamido)-2-methyl-5-(2-methyl-6-methylamino)pyridin-3-yl)benzamide

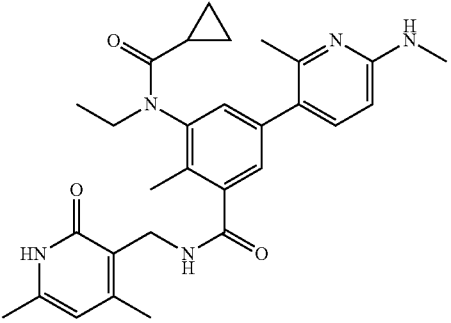

Synthesis of compound 90 was accomplished by using procedures similar to those described in Example 1.

Mass spectrometric data: LC-MS (ESI, m/z): 502.2740 [M+H]+.

Example 91

5-(2-(4-(cyclopropylmethyl)piperazin-1-yl)pyridin-4-yl)-N-((4,6-dimethyl-2-oxo-1,2-dihydropyridin-3-yl)methyl)-3-(N-ethylcyclopropanecarboxamido)-2-methylbenzamide Synthesis of compound 91 was accomplished by using procedures similar to those described in Example 1.

Mass spectrometric data: LC-MS (ESI, m/z): 597.3475 [M+H]+.

Example 92

3-(cyclopropanecarboxamido)-5-(6-(4-(cyclopropyl-methyl)piperazin-1-yl)-2-methylpyridin-3-yl)-N-((4,6-dimethyl-2-oxo-1,2-dihydro-2-dihydropyridin-3-yl)methyl)-2-methylbenzamide

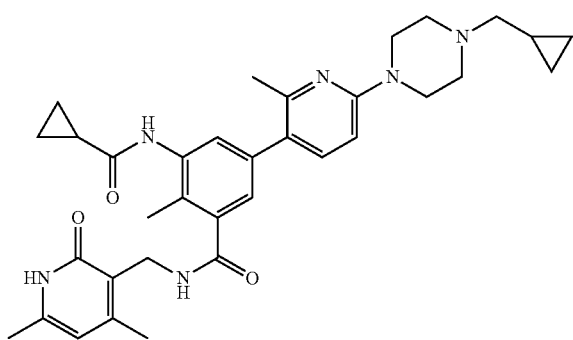

Synthesis of compound 92 was accomplished by using procedures similar to those described in Example 1.

Mass spectrometric data: LC-MS (ESI, m/z): 583.3318 [M+H]+.

Example 93

System for Screening Small Molecules of EZH2

EZH2 suppresses the expression of downstream E-cadherin, and upon EZH2 suppression, expression of E-cadherin will increase. Based on such principle, a reporter gene expression vector was constructed using luciferase.

Method for Constructing Reporter Gene

Genome DNA was extracted using DNeasy Blood & Tissue Kit (purchased from Qiagen, USA) as the extraction kit from 293T cells (purchased from ATCC, USA), the cell number of which is about $10^6$, and the extracted genome DNA was used a template for amplifying the promoter sequence of E-cadherin, using primers having sequences as shown below. The amplified fragments after PCR and the PGL4.1 vector (purchased from TAKARA, Japan) were respectively subjected to enzyme digestion with SacI and BglII (purchased from TAKARA, Japan), and then purified with PCR cleanup kit (Axygen PCR cleanup kit). Subsequently, the purified and enzyme-digested PCR products was ligated to the purified and enzyme-digested PGL4.1 vector using ligase solution I (DNA Ligation Kit Ver.2.1, purchased from TAKARA, Japan), and subjected to transformation. Single clones were then screened out and subjected to sequencing, and the obtained positive plasmid containing promoter fragments of Ecadherin was named E-cadherin RE-PGL4.1.

Primer Sequences for Amplifying Promoters of E-Cadherin:

```
                                           (SEQ ID NO:1)
GGCGAGCTCCTGATCATTATTCCCATTAGGAGGGTG
```

```
                                           (SEQ ID NO:2)
GGCAGATCTGGCTGGCCGGGGACGCCGAGCGAG
```

Meanwhile, a Renilla fluorescent vector was constructed using PCDNA4.1 (purchased from Thermofisher, USA) as the template to amplify the fragment of CMV promoter. After enzymatic digestion of the amplified CMV sequences and pGL4.70 vector (purchased from Promega, USA) with KpnI and XhoI (purchased from Promega, USA), purification was conducted with PCR cleanup kit (Axygen PCR cleanup kit). Then the enzyme-digested PCR product was ligated to the enzyme-digested PGL4.70 vector using ligase solution I (DNA Ligation Kit Ver.2.1, purchased from TAKARA, Japan) and the resultant was subjected to transformation. Subsequently single clones were screened and subjected to sequencing, and the obtained plasmid that contained CMV sequence was named as Plasmid Renilla luciferase-pGL4.70. Said plasmid utilized CMV promoter to achieve high expression of Renilla luciferase, which served as the control fluorescence for the primary screening system.

Sequences of primers used for amplifying CMV promoters are shown below:

```
                                           (SEQ ID NO:3)
GGCGGTACCGTTGACATTGATTATTGACTAGTTATTAATA
```

```
                                           (SEQ ID NO:4)
GGCCTCGAGGAGCTCTGCTTATATAGACCTCCCA
```

Inhibitors of EZH2 are capable of inhibiting EZH2 activity, leading to increased transcription and translation level of E-cadherin, which is reflected as increased chemiluminescence value in this system. In this experiment, 293T cells (purchased from ATCC, USA) were plated to a 96-well empty plate (purchased from CORNING) at room temperature, with about $1.5 \times 10^4$ cells per well. 12 hours after plating, 50 ng of purified E-cadherin RE-PGL4.0 and 1 ng of purified Renilla luciferase-pGL4.70 plasmid as well as 0.15 μl of transfection agent TransEL (purchased from Transgen, China) were mixed and were allowed to stand still for 20 minutes such that the plasmid was transiently transfected into 293T cells. After 6 hours, cells were treated for 24 hours by adding compounds of the invention to be tested as well as GSK126 (purchased from Shanghai Haoyuan Chemexpress Co., Ltd.), and detected with Dual-Glo® Luciferase Assay System (purchased from promega, USA) assay kit. The cells were firstly added with 20 μL Dual-Glo® Luciferase Assay Reagent, then incubated under room temperature for 10 minutes, and read on microplate reader Spectramax i3 (Molecular Devices, USA) to obtain the data of primary screening, which is shown in Table 1. Compounds that exhibited comparable with or stronger effects than GSK126 and compounds with similar structures were subjected to further screening.

TABLE 1

|  | 1 μM relative fluorescence intensity | 3 μM relative fluorescence intensity | 10 μM relative fluorescence intensity |
| --- | --- | --- | --- |
| GSK126 | 160.79 |  | 212.57 |
| Compound 14 | 171.64 |  | 289.08 |
| Compound 15 | 262.61 |  | 335.61 |
| Compound 16 | 200.36 | 252.26 | 226.24 |
| Compound 17 | 172 | 223 | 303 |
| Compound 18 | 289 | 356 | 423 |
| Compound 19 | 189 | 228 | 310 |
| Compound 20 | 193 | 213 | 227 |
| Compound 21 | 170 | 225 | 339 |
| Compound 22 | 171 | 194 | 242 |
| Compound 23 | 290 | 346 | 343 |
| Compound 25 | 116.28 |  | 228.14 |
| Compound 27 | 204.86 |  | 335.96 |
| Compound 28 | 163.93 |  | 345.23 |
| Compound 29 | 176.86 |  | 364.77 |

TABLE 1-continued

|  | 1 µM relative fluorescence intensity | 3 µM relative fluorescence intensity | 10 µM relative fluorescence intensity |
|---|---|---|---|
| Compound 30 | 253.44 |  | 231.21 |
| Compound 33 | 123.27 |  | 224.69 |
| Compound 34 | 98.36 |  | 109.72 |
| Compound 35 | 83.82 |  | 123.19 |
| Compound 36 | 211.26 |  | 312.36 |
| Compound 37 | 163.93 |  | 345.23 |
| Compound 41 | 156.04 |  | 183.38 |
| Compound 42 | 179.84 |  | 234.50 |
| Compound 43 | 147.30 |  | 235.05 |
| Compound 44 | 181.04 |  | 217.02 |
| Compound 45 | 189.05 |  | 218.76 |
| Compound 53 | 115.15 | 134.49 | 167 |
| Compound 54 | 119.48 | 139.11 | 187.44 |
| Compound 55 | 132.74 | 127.10 | 174.04 |
| Compound 56 | 130 | 156 | 160 |
| Compound 57 | 101 | 110 | 109 |
| Compound 59 | 153 | 152 | 150 |
| Compound 60 | 143 | 140 | 171 |

Example 94

EZH2 Enzymatic Activity Assay System

Enzymatic activity assay was conducted using EZH2 (Y641F) TR-FRET assay KIT from Cisbio company on compounds that were shown to be active in primary screening, wherein GSK126 (purchased from Shanghai Haoyuan Chemexpress Co., Ltd.) and EPZ6438 (CAS No. 1403254-99-8, purchased from Shanghai Haoyuan Chemexpress Co., Ltd.) were used as control.

2 µL of PRC2 protein complex that contained 14 ng protein (comprising EZH2(Y641F), EED protein, SUZ12 protein, RbAp48 protein and AEBP2 protein, purchased from BPS Bioscience, USA, catalog #51017) and 4 µL of 10 mM of 3-fold gradient diluted compounds of the invention were mixed respectively, and incubated for 5 minutes in a 384-well shallow plate at room temperature. Then the reaction substrates, 2 µL of 2.5 µM Histone3K27ME1 (purchased from AnaSpec, USA, catalog #65366) and 2 µL 75 µM adenosylmethionine (SAM) (purchased from sigma, USA, catalog # A7007), were mixed and incubated at room temperature for 4 hours. Subsequently 5 µL of the assay antibody, H3K27me3-Eu(K)Ab (purchased from cisbio bioassays, USA, #61 KC3KAE) and 5 µL Streptavidin-XL665 (purchased from cisbio bioassays, USA, #610SAXLA), were added and incubated for 1 hour at room temperature. The resultant was read on Spectramax i3 (Molecular Devices, USA) which was set in a TR-FRET reading mode, to obtain absorption data at wavelength 665 nm and 620 nm. The ratio between the data at wavelength 665 nm and the data at wavelength 620 nm was calculated and then the data was analyzed using graphpad to obtain a fitted inhibition curve of small molecules, yielding the data of Table 2.

Meanwhile, the inventors further conducted Western Blot with Pfeiffer cells (purchased from ATCC, USA) for verification. Specific steps comprise treating EZH2 gene-harboring Pfeiffer cell strains with different concentrations of (0 µM, 0.01 µM, 0.1 µM, 0.3 µM, 1.11 µM, 3.33 µM, 10 µM in DMSO) of compounds of the present invention and EZH2 inhibitors (GSK126 and EPZ6438, serving as control) for 72 hours, respectively and then samples were collected. Effect of compounds on H3K27m3 methylation in cells was assessed.

It was shown in the experiments that Compounds 64 and 65 exhibited superior effects than control compounds EPZ6438 and GSK126, no matter in Western Blot verification on cells or in TR-FRET enzymatic activity kit. Compounds 5, 24, 25, 63, 64, 65, 69, 71 and 74 exhibited superior activity than control compounds GSK126 and EPZ6438 in the assay using a TR-FRET kit.

TABLE 2

| Test compound | $IC_{50}$ (µM) pfeiffer | TR-FRET $IC_{50}$ (nM) |
|---|---|---|
| GSK126 | 1.4 | 121.1 |
| EPZ6438 | 0.037 | 219.3 |
| Compound 5 | 0.086 | 75 |
| Compound 16 | 0.126 |  |
| Compound 24 | 0.073 | 80.6 |
| Compound 25 | 0.063 | 58.6 |
| Compound 29 | 2.6 |  |
| Compound 31 | 0.087 | 444.3 |
| Compound 32 | 0.95 |  |
| Compound 33 | 0.67 |  |
| Compound 38 | 0.23 | 515.2 |
| Compound 39 | 0.83 |  |
| Compound 40 | 0.24 | 219.6 |
| Compound 63 | 0.43 | 103 |
| Compound 64 | 0.03 | 103 |
| Compound 65 | 0.024 | 29 |
| Compound 69 | 0.064 | 20 |
| Compound 71 | 0.041 | 16 |
| Compound 74 | 0.093 | 23 |

INDUSTRIAL APPLICABILITY

The present invention provides an inhibitor, having the structure of formula (I), of wild-type and Y641F mutant human histone methyltransferase EZH2, and the present invention further provides a method for treating a cancer or a cancerous condition associated with EZH2 activity using said inhibitor, as well as uses of the inhibitor. Thus, the above inhibitor can be prepared into a corresponding medicament and therefore has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:

1. A compound of formula (I), or a pharmaceutically acceptable salt, solvate, ester, acid, metabolite or prodrug thereof:

(I)

wherein,

Y is selected from a group consisting of cyano, aminoacyl, alkylamino optionally substituted with one $R_4$, aryl optionally substituted with 1-3 independent $R_4$, heteroaryl optionally substituted with 1-3 independent $R_4$, and heterocycloalkylalkylamino optionally substituted with 1-3 independent $R_4$;

$R_1$ is alkyl;

$R_2$ is selected from a group consisting of hydrogen, alkyl and cycloalkylalkyl;

$R_3$ is selected from a group consisting of alkyl (excluding alkenyl), cycloalkyl, heterocycloalkyl, heteroaryl, alkylaryl, and bicyclo[2.2.1]hept-2-enyl;

$R_4$ is independently selected from a group consisting of hydrogen, halo, amino, cyano, alkyl, alkoxy, alkanoyl, alkylamino optionally substituted with one $R_5$, alkylsulfonamide optionally substituted with one $R_5$, cycloalkylsulfonamide optionally substituted with one $R_5$, heterocycloalkyl optionally substituted with 1-3 independent $R_5$, heterocycloalkylcarbonyl optionally substituted with 1-3 independent $R_5$, heterocycloalkylalkyl optionally substituted with 1-3 independent $R_5$, heterocycloalkylalkoxy optionally substituted with 1-3 independent $R_5$, heterocycloalkylcarbonylalkyl optionally substituted with 1-3 independent $R_5$, and aryloxy optionally substituted with 1-3 independent $R_5$; and $R_5$ is independently selected from a group consisting of amino, alkyl, alkanoyl, alkylamino, hydroxyalkyl, cycloalkyl, cycloalkylalkyl, heterocycloalkyl, and amino protecting group.

2. The compound or a pharmaceutically acceptable salt, solvate, ester, acid, metabolite or prodrug thereof according to claim 1:

wherein Y is selected from a group consisting of cyano, aminoacyl, (2-(dimethylamino)ethyl)(methyl)amino, phenyl, pyridyl, thienyl, (2-morpholinoethyl)amino, and (3-morpholinopropyl)amino, wherein phenyl, pyridyl, thienyl, (2-morpholinoethyl)amino, and (3-morpholinopropyl)amino are optionally substituted with 1-3 independent $R_4$; and wherein R₄ is independently selected from a group consisting of fluoro, chloro, amino, cyano, methyl, methoxy, acetyl, (2-(dimethylamino)ethyl)amino, (2-(dimethylamino)ethyl)(methyl)amino, isopropylsulfonamide, cyclopropylsulfonamide, piperidyl, piperazinyl, morpholinyl, homopiperazinyl, morpholin-4-carbonyl, morpholinomethyl, piperidylmethyl, piperazinylmethyl, morpholinoethoxyl, morpholinopropoxy, morpholin-4-carbonylmethyl, and phenoxy, wherein piperidyl, piperazinyl, morpholinyl, homopiperazinyl, morpholin-4-carbonyl, morpholinomethyl, piperidylmethyl, piperazinylmethyl, morpholinoethoxyl, morpholinopropoxy, morpholin-4-carbonylmethyl, and phenoxy are optionally substituted with 1-3 independent R₅; and wherein R₅ is independently selected from a group consisting of amino, methyl, ethyl, isopropyl, acetyl, dimethylamino, hydroxymethyl, cyclopropyl, cyclopropylmethyl, pyrrolyl, and t-butyloxycarbonyl.

3. The compound or a pharmaceutically acceptable salt, solvate, ester, acid, metabolite or prodrug thereof according to claim 1, wherein R₁ is selected from a group consisting of methyl, ethyl, and propyl; R₂ is selected from a group consisting of methyl, ethyl, propyl, and cyclopropylmethyl; R₃ is selected from a group consisting of isopropyl, neopentyl, tert-pentyl, pent-3-yl, cyclopropyl, cyclobutyl, cyclopentyl, cyclohexyl, tetrahydropyranyl, furyl, methylphenyl, and bicyclo[2.2.1]hept-2-enyl.

4. The compound or a pharmaceutically acceptable salt, solvate, ester, acid, metabolite or prodrug thereof according to claim 1, wherein Y is phenyl, pyridin-3-yl, or pyridin-4-yl substituted with R₄; and wherein R₄ is selected from a group consisting of fluoro, methyl, 4-(cyclopropylmethyl)piperazin-1-yl, morpholinoethoxyl, morpholinopropoxy, morpholinomethyl, or piperazinylmethyl with its N atom optionally substituted with an amino protecting group;

R₁ is methyl;

R₂ is ethyl;

R₃ is cyclopropyl or cyclopentyl.

5. The compound or a pharmaceutically acceptable salt, solvate, ester, acid, metabolite or prodrug thereof according to claim 1, wherein the compound is of the structure formula (II):

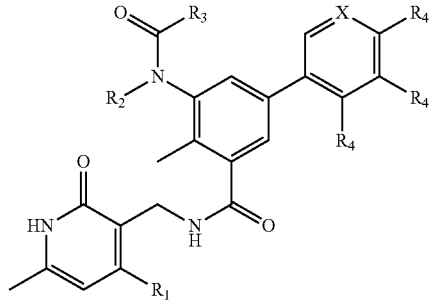

(II)

wherein, X is selected from a group consisting of CH and N, and R₁, R₂, R₃ and R₄ are as defined in claim 1.

6. The compound or a pharmaceutically acceptable salt, solvate, ester, acid, metabolite or prodrug thereof according to claim 5, wherein X is CH;

R₁ is methyl;

R₂ is ethyl;

R₃ is selected from a group consisting of isopropyl, neopentyl, tert-pentyl, pent-3-yl, cyclopropyl, cyclobutyl, cyclopentyl, cyclohexyl, tetrahydropyran-4-yl, furan-2-yl, p-methylphenyl, and bicyclo[2.2.1]hept-2-enyl;

each of R₄ is independently selected from a group consisting of hydrogen, fluoro, methyl, isopropylsulfonamide optionally substituted with one R₅, cyclopropylsulfonamide optionally substituted with one R₅, piperidyl optionally substituted with 1-3 independent R₅, piperazinyl optionally substituted with 1-3 independent R₅, morpholinyl optionally substituted with 1-3 independent R₅, morpholin-4-carbonyl optionally substituted with 1-3 independent R₅, morpholinomethyl optionally substituted with 1-3 independent R₅, piperidylmethyl optionally substituted with 1-3 independent R₅, piperazinylmethyl optionally substituted with 1-3 independent R₅, morpholinoethoxyl optionally substituted with 1-3 independent R₅, morpholinopropoxy optionally substituted with 1-3 independent R₅, morpholin-4-carbonylmethyl optionally substituted with 1-3 independent R₅, and phenoxy optionally substituted with 1-3 independent R₅;

R₅ is independently selected from a group consisting of ethyl, cyclopropylmethyl, dimethylamino, hydroxymethyl, and t-butyloxycarbonyl.

7. The compound or a pharmaceutically acceptable salt, solvate, ester, acid, metabolite or prodrug thereof according to claim 1, which is selected from a group consisting of:

Compound 1

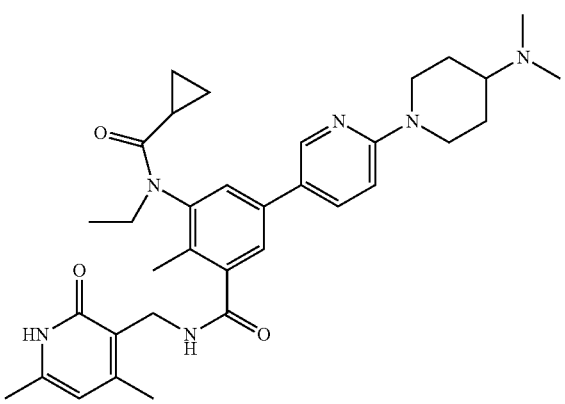

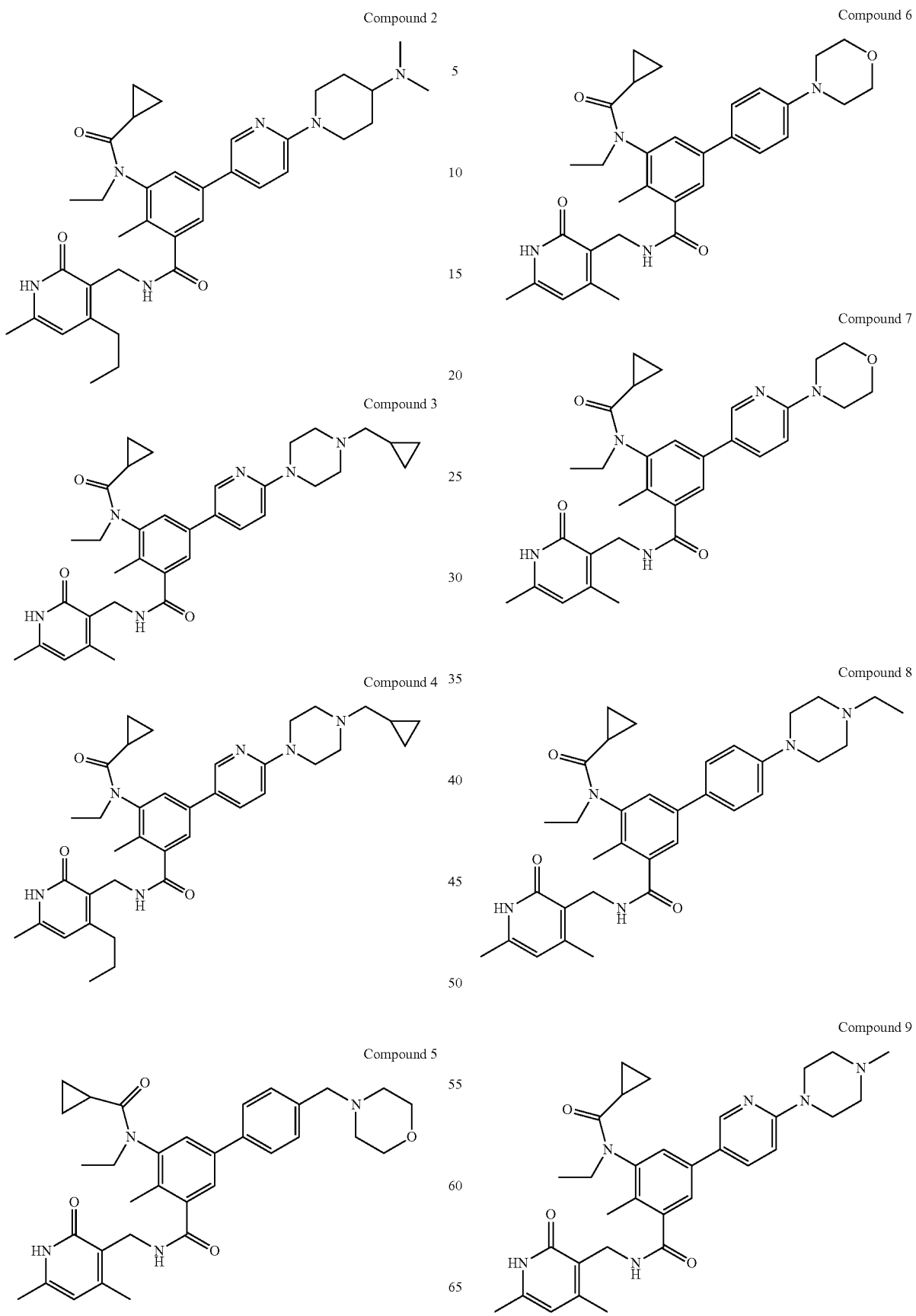

Compound 10
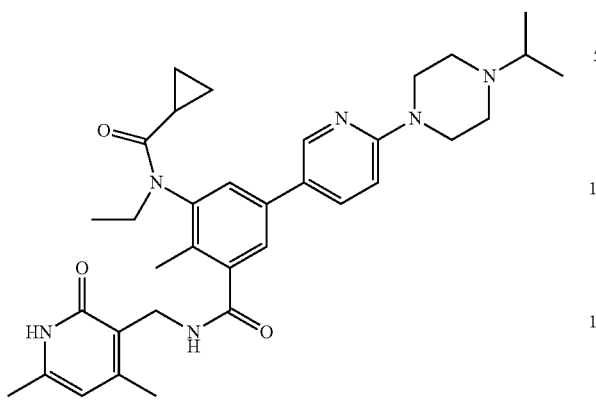
Compound 11
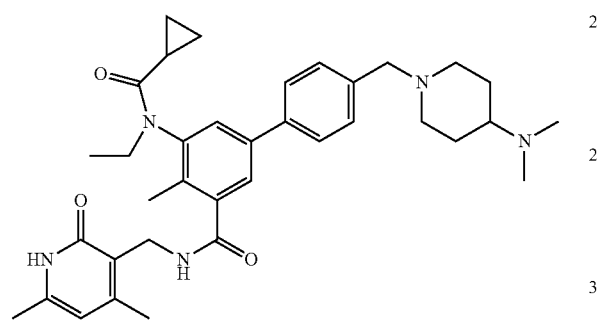
Compound 12
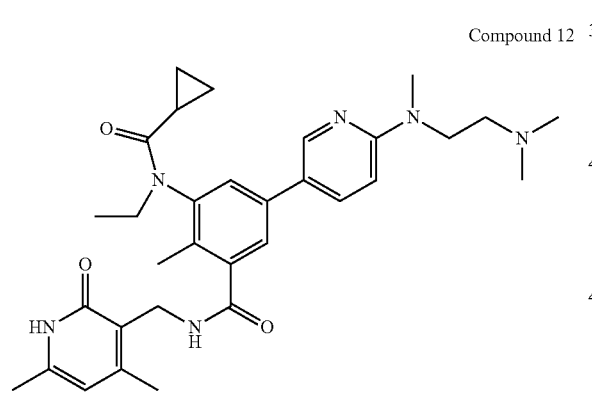
Compound 13
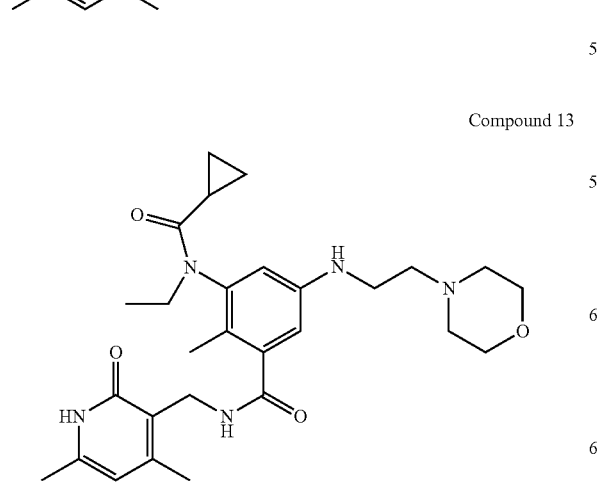
Compound 14
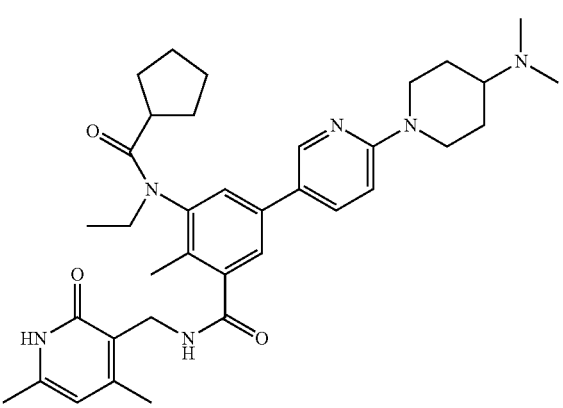
Compound 15
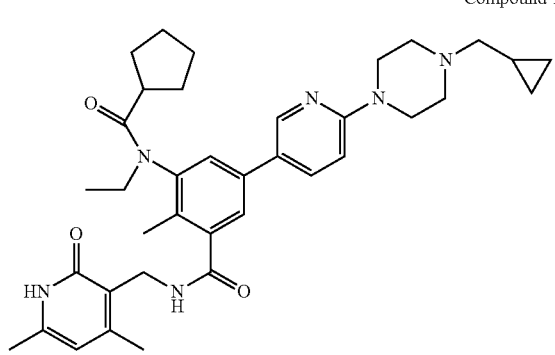
Compound 16
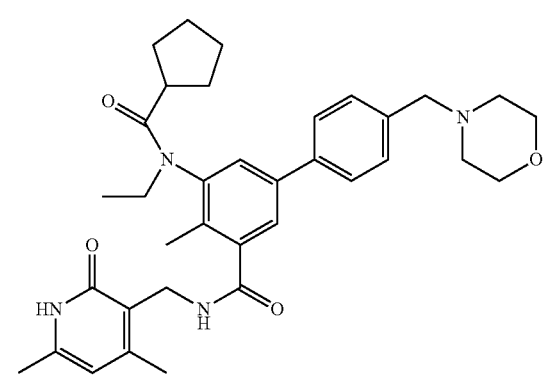
Compound 17
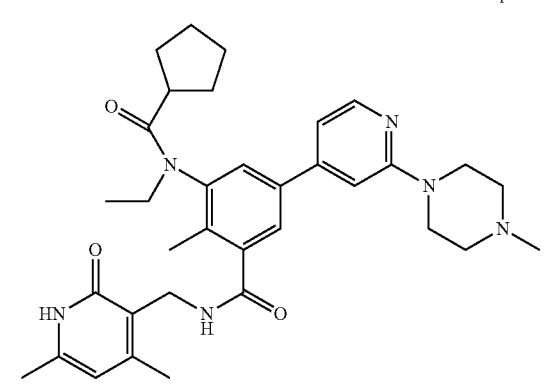

Compound 18
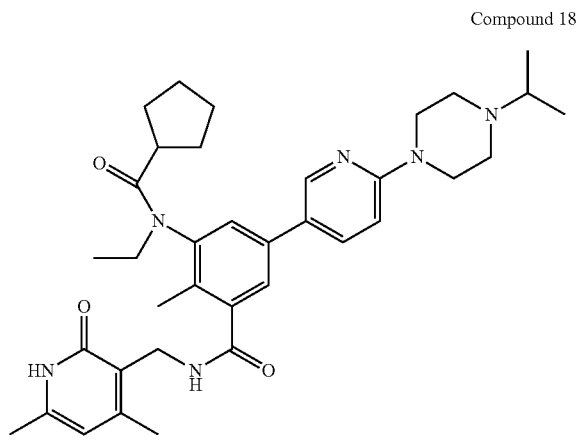
Compound 19
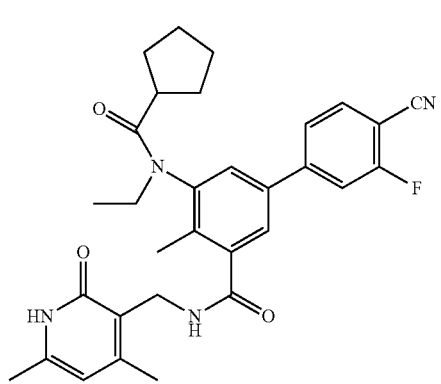
Compound 20
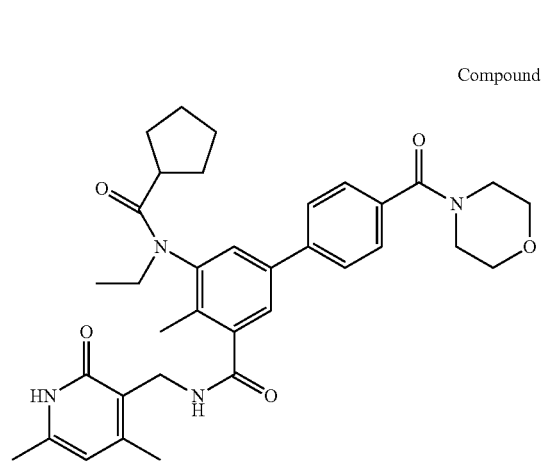
Compound 21
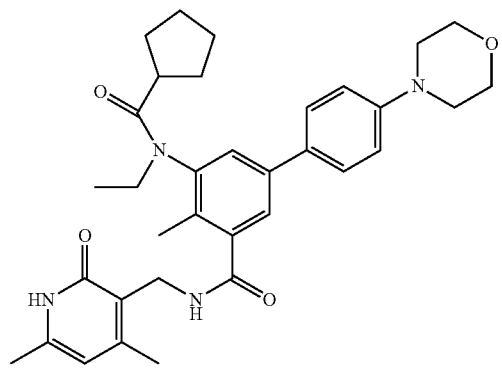
Compound 22
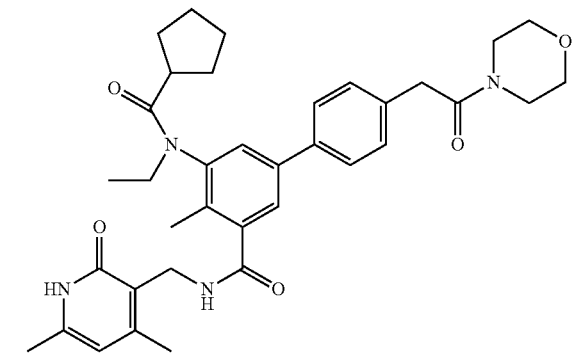
Compound 23
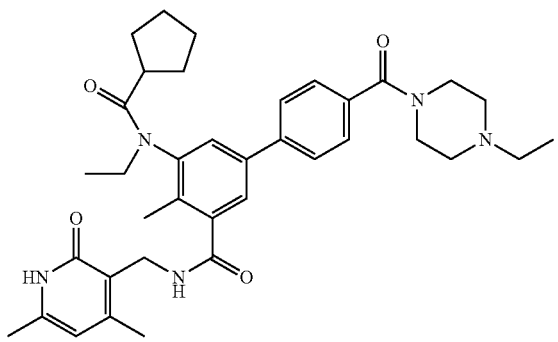
Compound 24
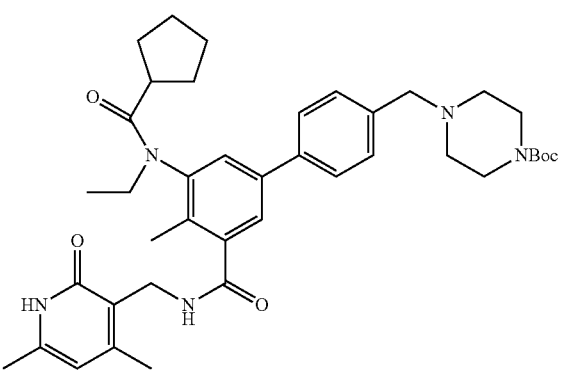
Compound 25
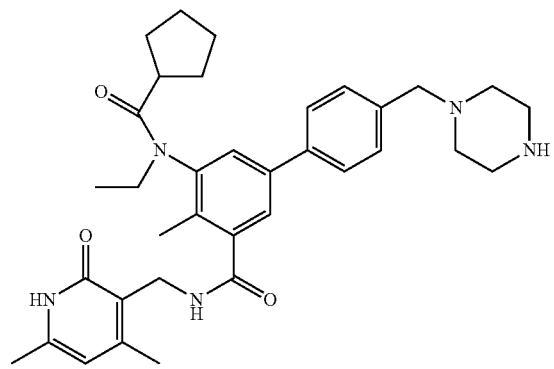

Compound 26
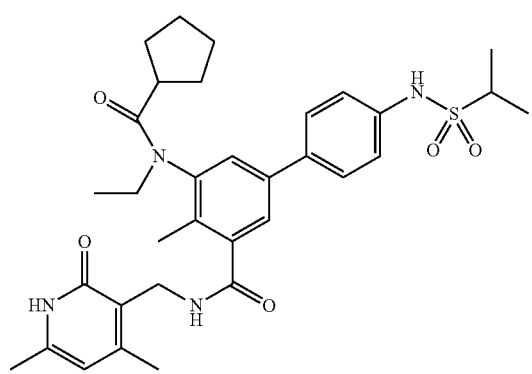
Compound 27
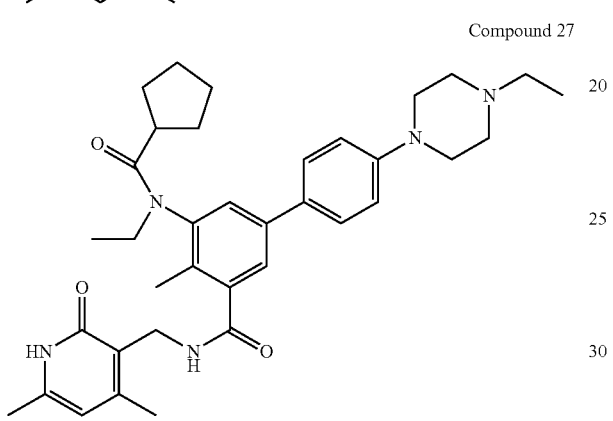
Compound 28
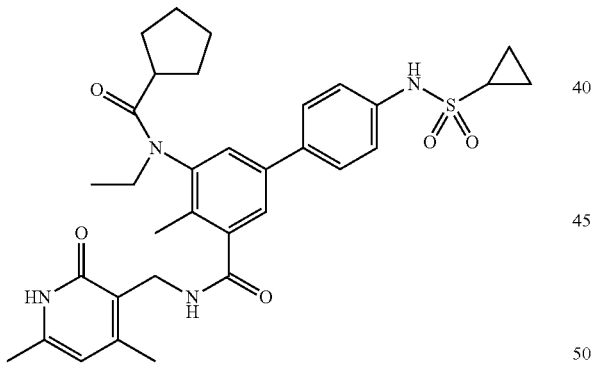
Compound 29
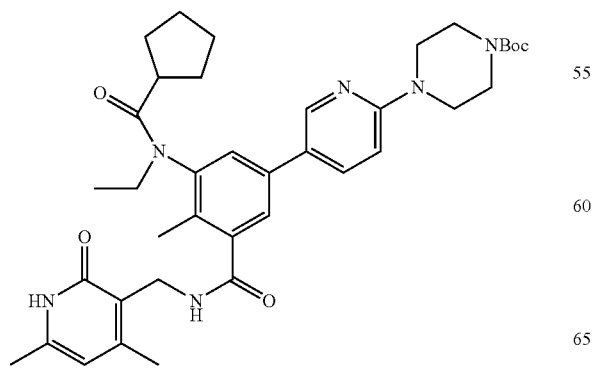
Compound 30
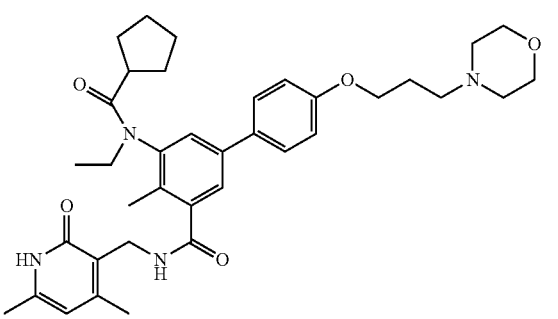
Compound 31
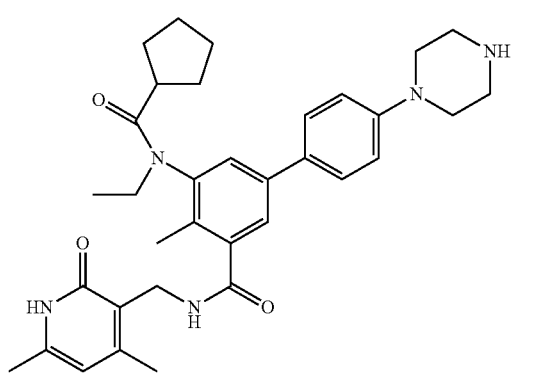
Compound 32
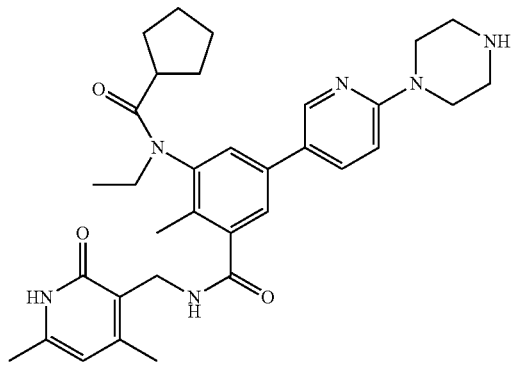
Compound 33
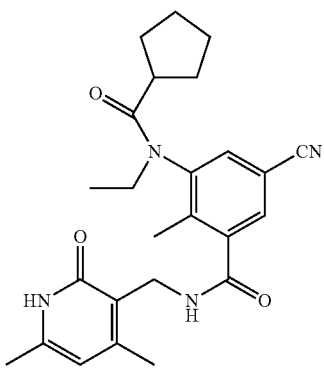

Compound 34
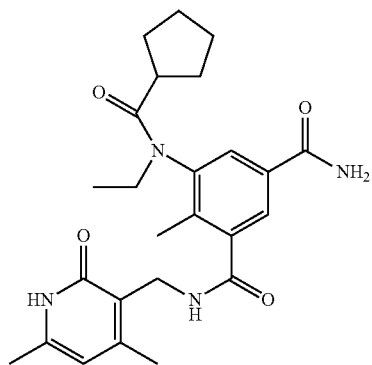
Compound 35
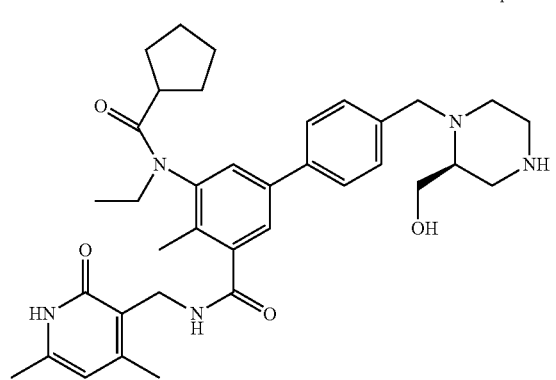
Compound 36
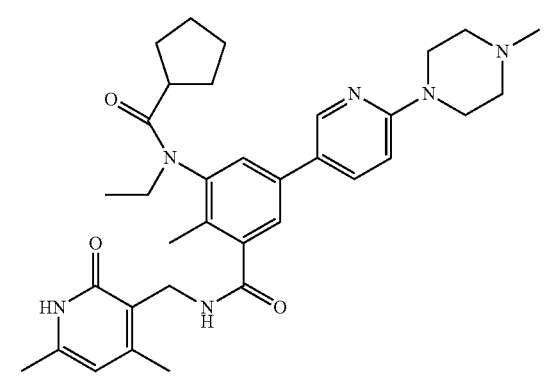
Compound 37
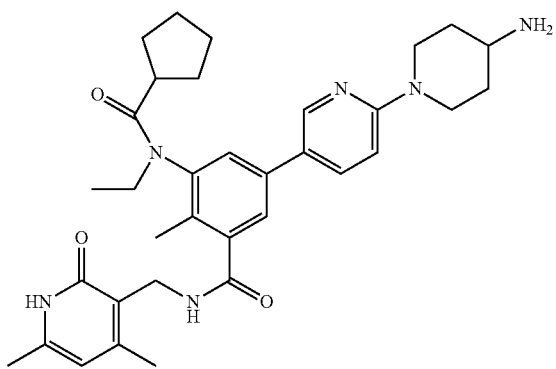
Compound 38
Compound 39
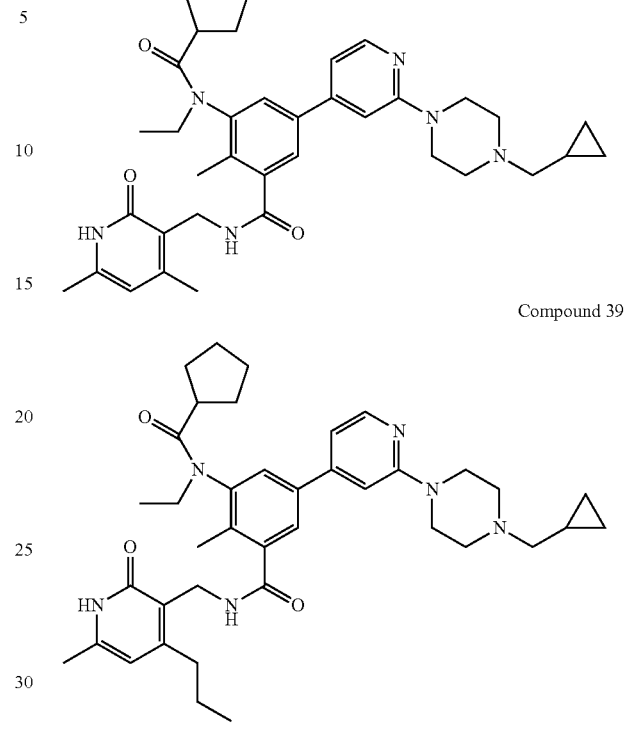
Compound 40
Compound 41
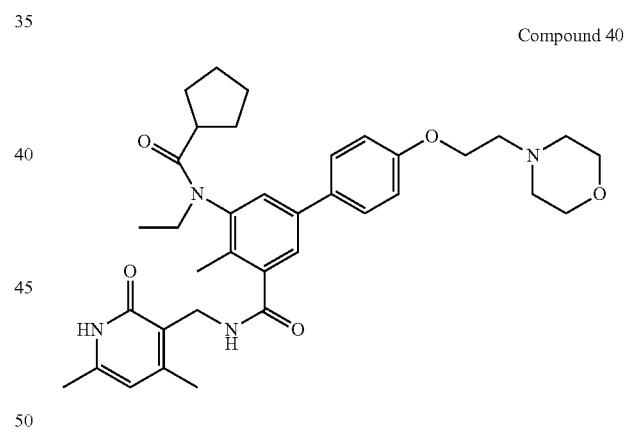
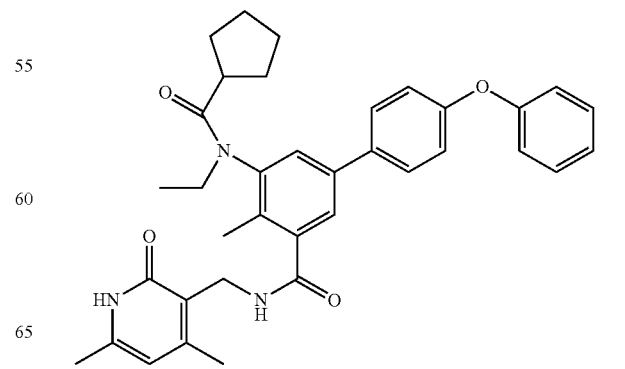

Compound 42
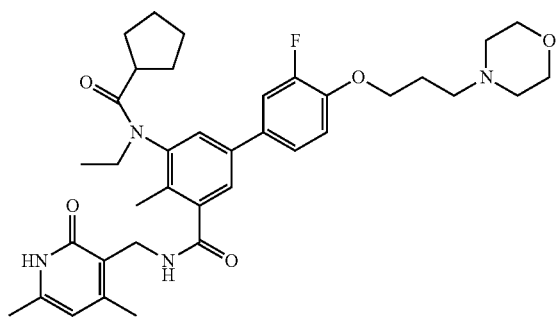
Compound 46
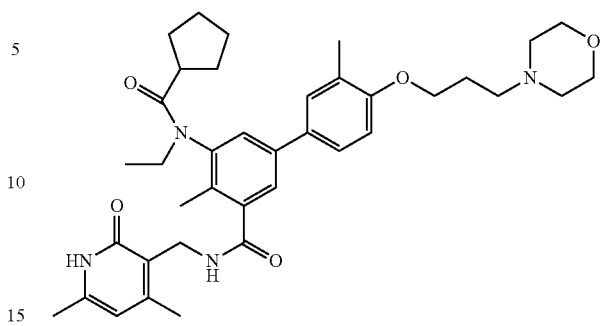
Compound 43
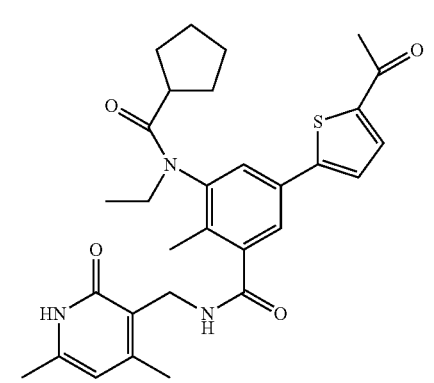
Compound 47
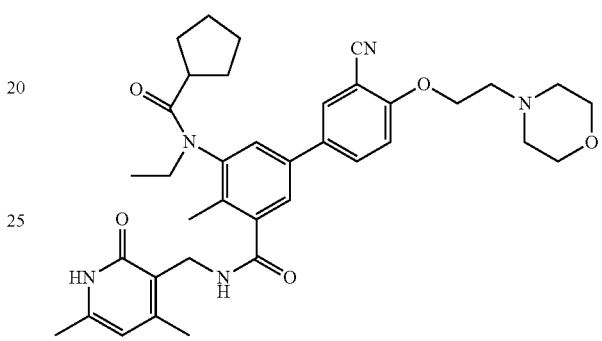
Compound 44
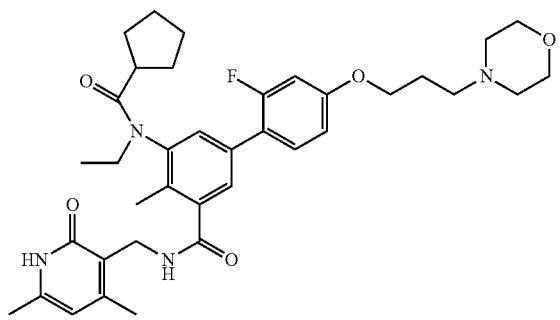
Compound 48
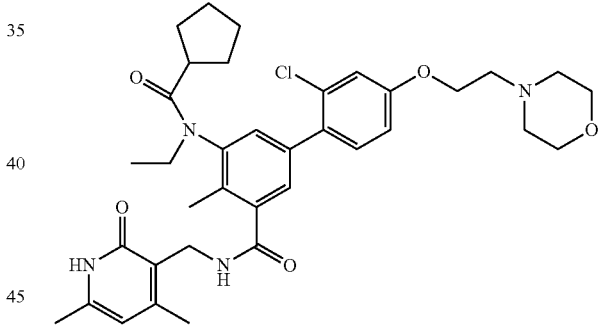
Compound 45
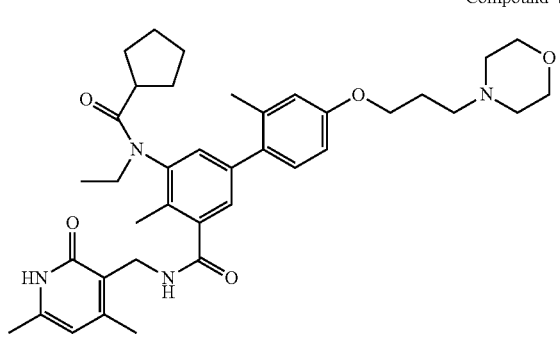
Compound 49
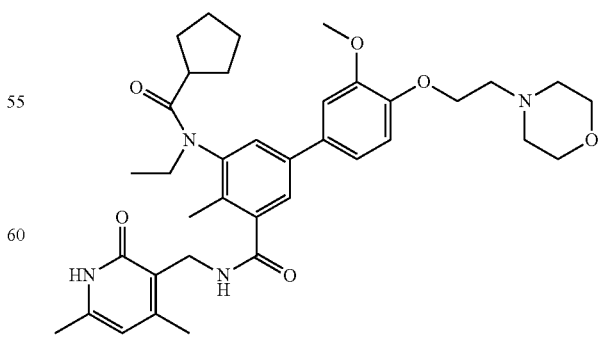

Compound 50
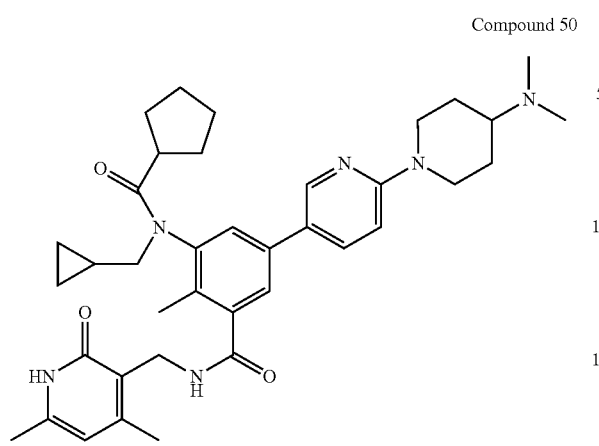
Compound 51
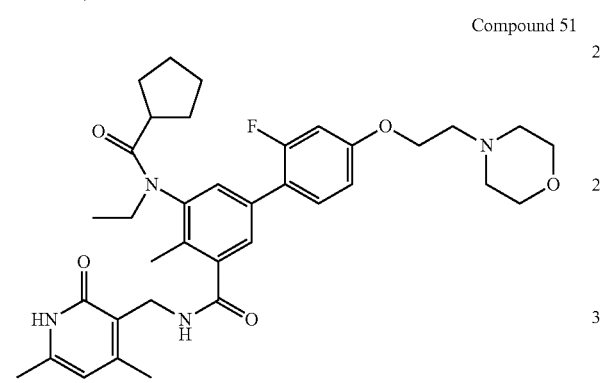
Compound 52
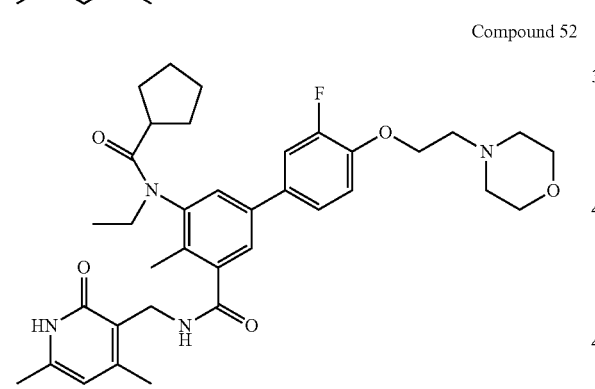
Compound 53
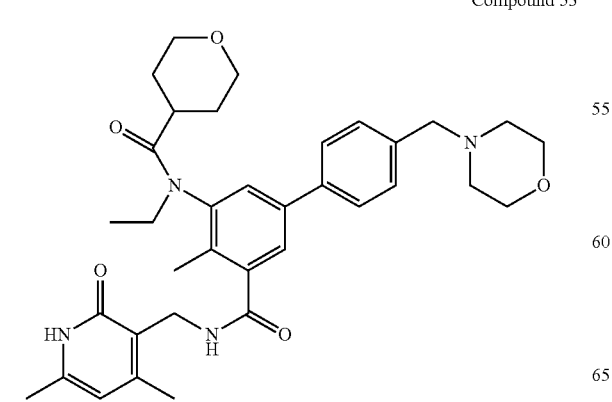
Compound 54
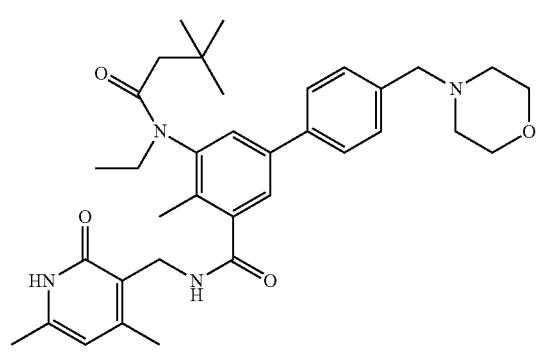
Compound 55
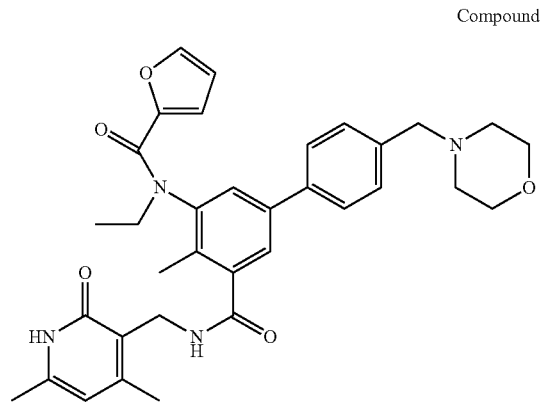
Compound 56
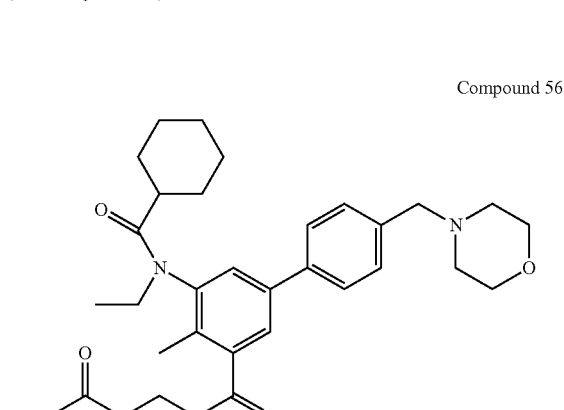
Compound 57
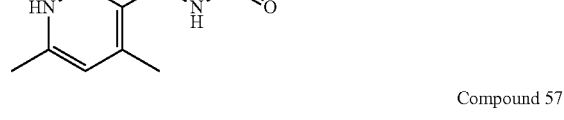

Compound 58
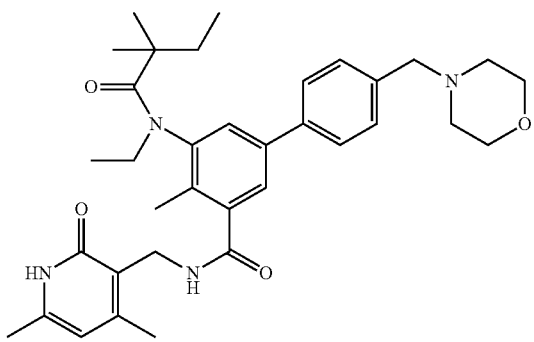
Compound 59
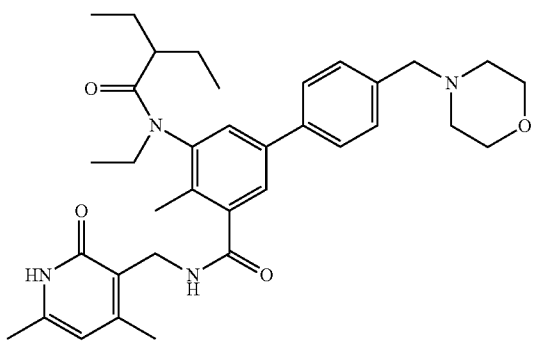
Compound 60
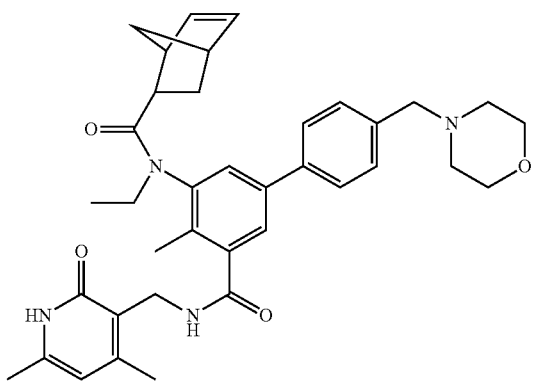
Compound 61
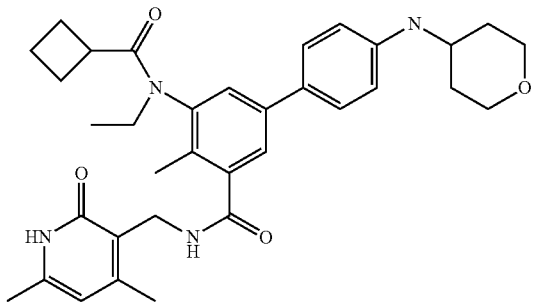
Compound 62
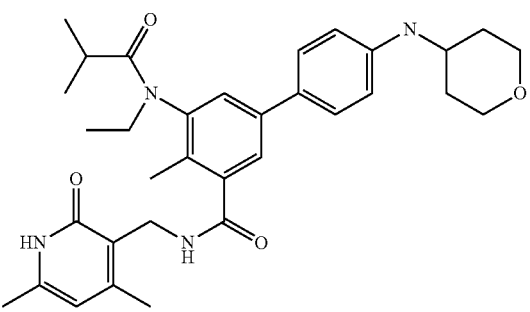
Compound 63
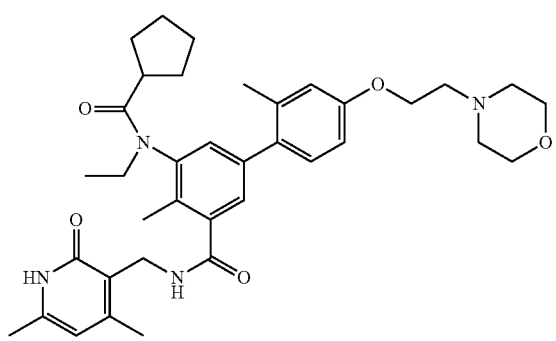
Compound 64
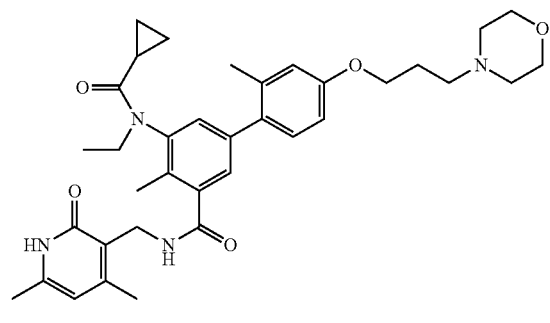
Compound 65
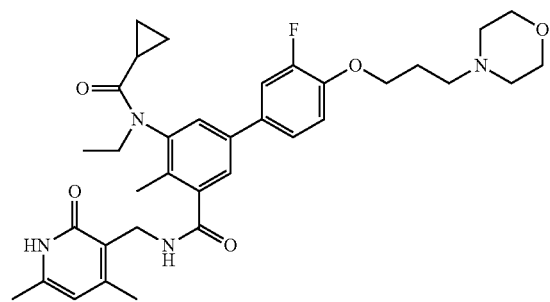

Compound 66
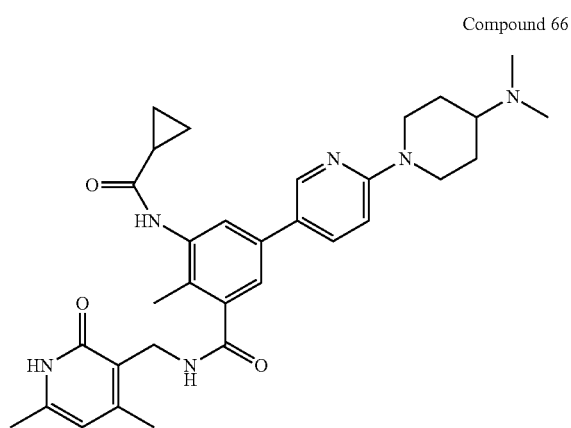
Compound 70
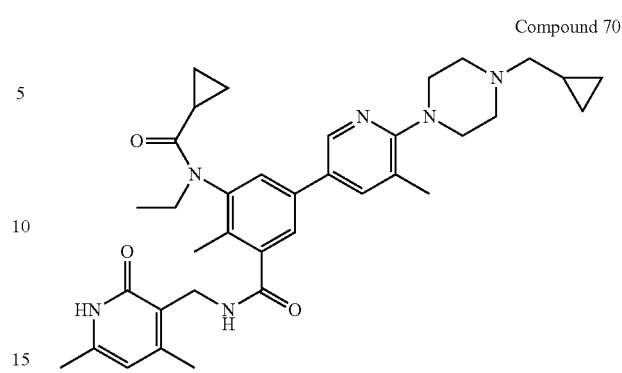
Compound 67
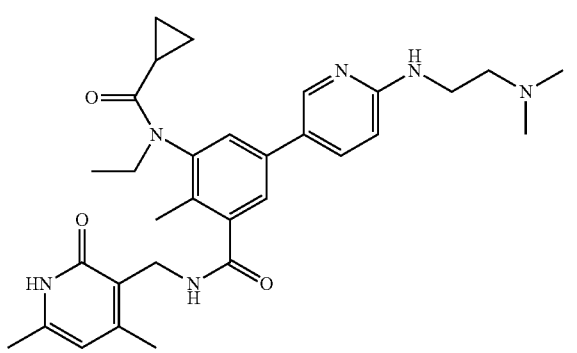
Compound 71
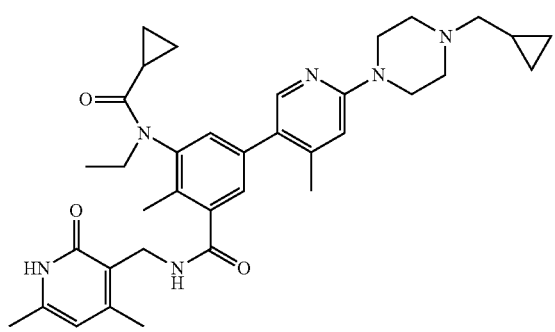
Compound 68
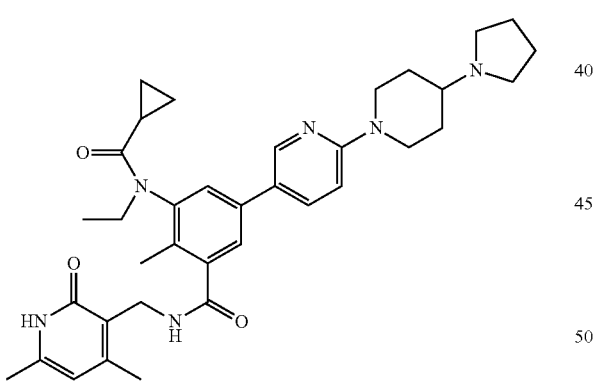
Compound 72
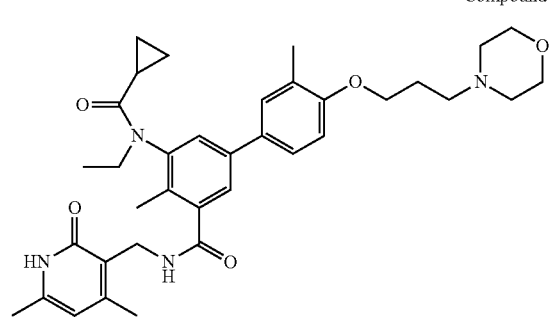
Compound 69
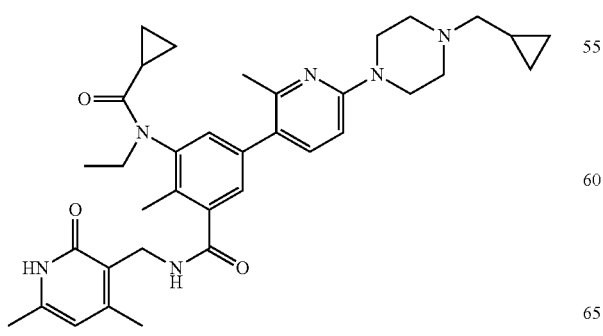
Compound 73
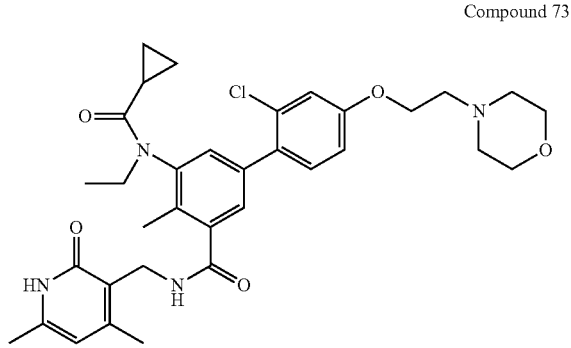

Compound 74
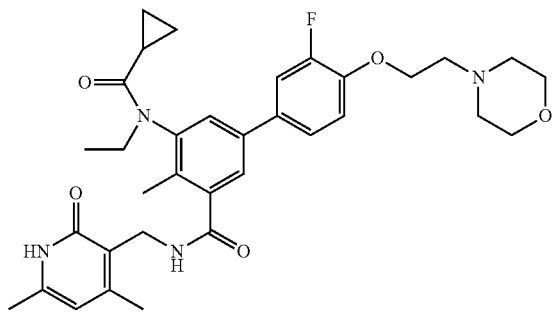
Compound 75
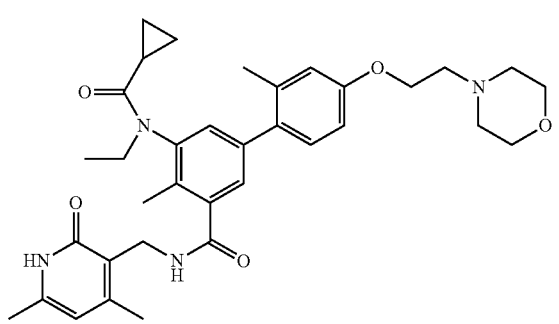
Compound 76
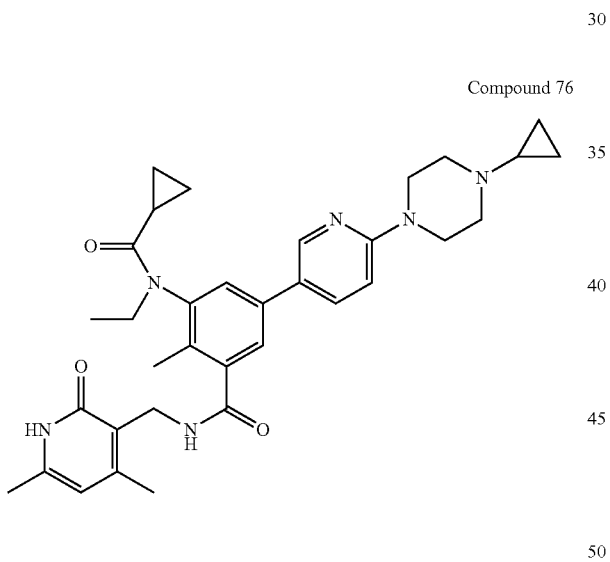
Compound 77
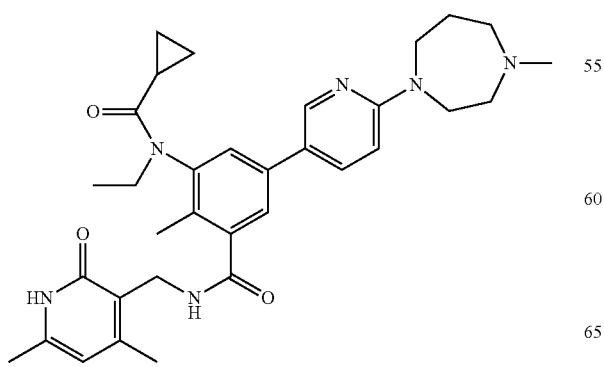
Compound 78
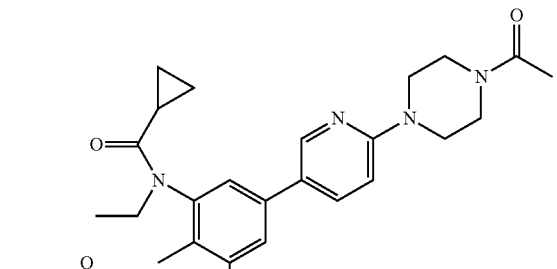
Compound 79
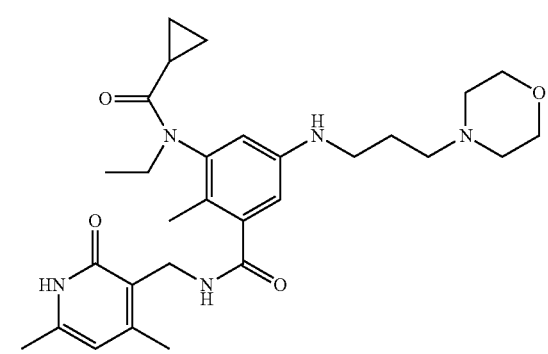
Compound 80
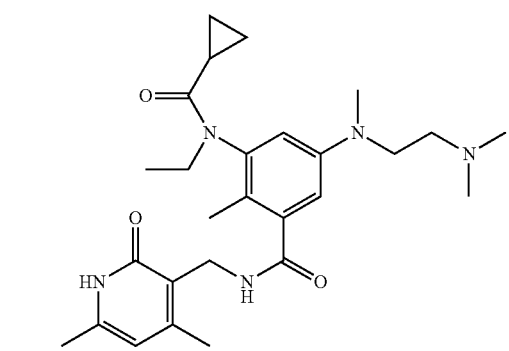
Compound 81
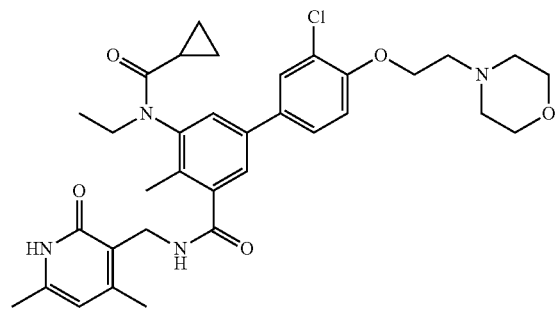

Compound 82
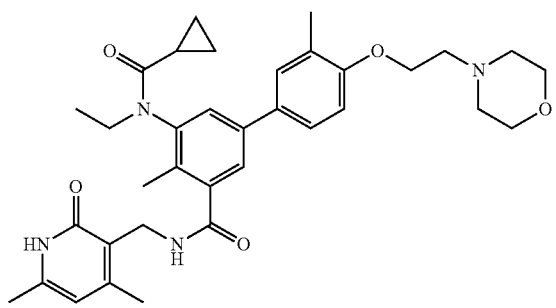
Compound 86
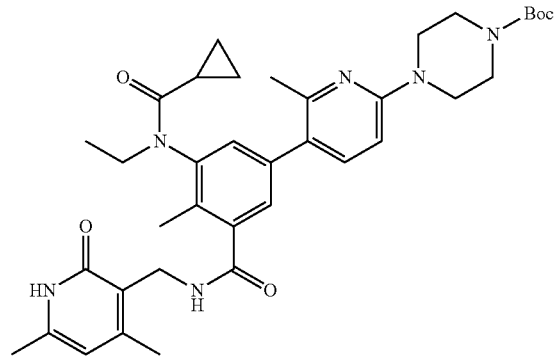 [SMILES: CCN(C(=O)C1CC1)c1cc(-c2ccc(N3CCN(C(=O)OC(C)(C)C)CC3)nc2C)cc(C(=O)NCc2c(C)cc(C)[nH]c2=O)c1C]
Compound 83
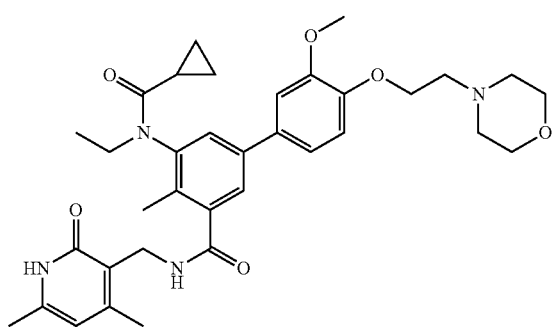
Compound 87
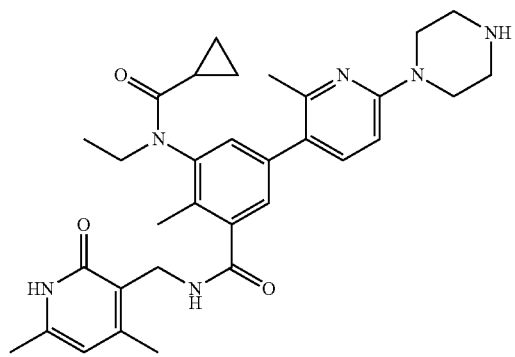 [SMILES: CCN(C(=O)C1CC1)c1cc(-c2ccc(N3CCNCC3)nc2C)cc(C(=O)NCc2c(C)cc(C)[nH]c2=O)c1C]
Compound 84
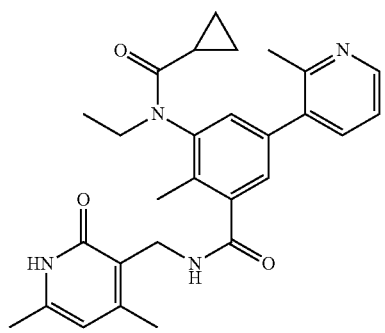
Compound 88
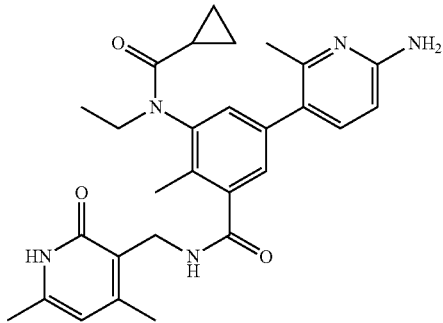 [SMILES: CCN(C(=O)C1CC1)c1cc(-c2ccc(N)nc2C)cc(C(=O)NCc2c(C)cc(C)[nH]c2=O)c1C]
Compound 85
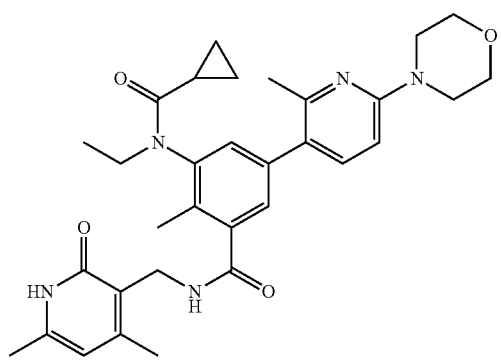
Compound 89
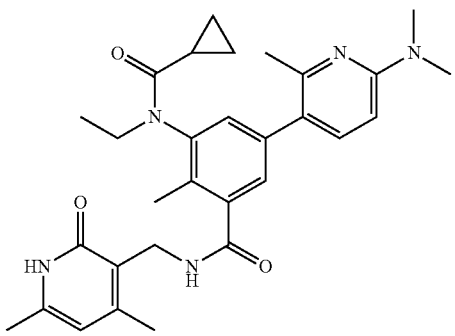

Compound 90

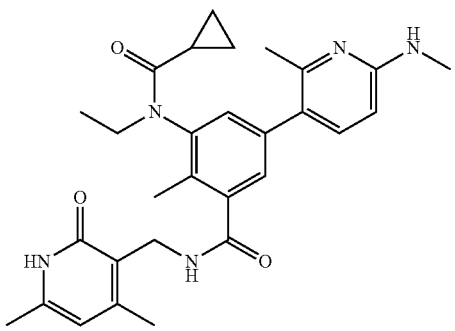

Compound 91

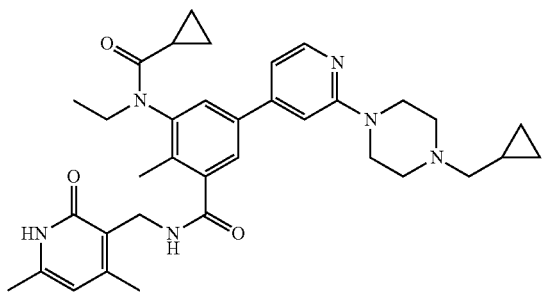 [SMILES: CCN(C(=O)C1CC1)c1cc(-c2ccnc(N3CCN(CC4CC4)CC3)c2)cc(C(=O)NCc2c(C)cc(C)[nH]c2=O)c1C]

Compound 92

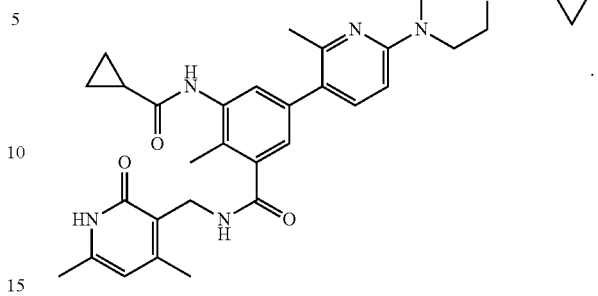

8. A pharmaceutical composition, comprising the compound or a pharmaceutically acceptable salt, solvate, ester, acid, metabolite or prodrug thereof according to claim 1 and a pharmaceutically acceptable carrier or excipient, as well as optionally other therapeutic agents.

9. A method of inhibiting activity of EZH2 in a subject, wherein the method comprises administering the compound or a pharmaceutically acceptable salt, solvate, ester, acid, metabolite or prodrug thereof according to claim 1 to the subject.

10. The method according to claim 9, wherein the EZH2 is wild-type EZH2 and/or Y641F mutant EZH2.

11. A method for treating a cancer or a precancerous condition associated with EZH2 activity in a subject, wherein the method comprises administering the compound or a pharmaceutically acceptable salt, solvate, ester, acid, metabolite or prodrug thereof according to claim 1 to the subject.

12. The method according to claim 11, wherein the cancer is selected from a group consisting of lymphoma, leukemia and melanoma.

13. The method according to claim 12, wherein the lymphoma is selected from a group consisting of a non-Hodgkin's lymphoma, a follicular lymphoma and a diffuse large B-cell lymphoma.

14. The method according to claim 12, wherein the leukemia is a chronic myelogenous leukemia.

15. The method according to claim 11, wherein the precancerous condition is a myelodysplastic syndrome.

* * * * *